(12) United States Patent
Mirica et al.

(10) Patent No.: US 11,092,562 B2
(45) Date of Patent: Aug. 17, 2021

(54) CONDUCTIVE TEXTILES AND USES THEREOF IN FUNCTIONAL DEVICES

(71) Applicant: Dartmouth College, Hanover, NH (US)

(72) Inventors: Katherine A. Mirica, Hanover, NH (US); Merry K. Smith, Lyme, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 465 days.

(21) Appl. No.: 15/962,156

(22) Filed: Apr. 25, 2018

(65) Prior Publication Data
US 2018/0306740 A1 Oct. 25, 2018

Related U.S. Application Data

(60) Provisional application No. 62/489,851, filed on Apr. 25, 2017.

(51) Int. Cl.
*G01N 27/12* (2006.01)
*D06M 13/503* (2006.01)
(Continued)

(52) U.S. Cl.
CPC .......... *G01N 27/125* (2013.01); *D06M 13/07* (2013.01); *D06M 13/148* (2013.01);
(Continued)

(58) Field of Classification Search
None
See application file for complete search history.

(56) References Cited

U.S. PATENT DOCUMENTS

| | | | |
|---|---|---|---|
| 2012/0028846 A1* | 2/2012 | Yaghi | B01J 20/226 506/39 |
| 2012/0115961 A1* | 5/2012 | Hafizovic | B01J 31/1691 514/772 |

(Continued)

OTHER PUBLICATIONS

Neufeld et al., Immobilization of Metal-Organic Framework Copper(II) Benzene-1,3,5-tricarboxylate (CuBTC) onto Cotton Fabric as a Nitric Oxide Release Catalyst, ACS Applied Materials & Interfaces 2015 7 (48), 26742-26750.
(Continued)

*Primary Examiner* — Lore R Jarrett
(74) *Attorney, Agent, or Firm* — Winstead PC

(57) ABSTRACT

Embodiments of the present disclosure pertain to conductive textiles that include a textile component with a plurality of fibers; and metal-organic frameworks associated with the fibers of the textile component in the form of a conductive network. Metal-organic frameworks may have a two-dimensional structure and a crystalline form. Metal-organic frameworks may be conformally coated on the fibers of the textile component. Additional embodiments of the present disclosure pertain to methods of sensing an analyte in a sample by exposing the sample to a conductive textile; and detecting the presence or absence of the analyte by detecting a change in a property of the conductive textile, and correlating the change in the property to the presence or absence of the analyte. The analyte in the sample may reversibly associate with the conductive textile. The association may also result in filtration, pre-concentration, and capture of the analyte by the conductive textile.

14 Claims, 42 Drawing Sheets

(51) Int. Cl.
| | |
|---|---|
| D06M 15/687 | (2006.01) |
| D06M 13/07 | (2006.01) |
| D06M 13/332 | (2006.01) |
| D06M 13/335 | (2006.01) |
| D06M 13/148 | (2006.01) |
| D06M 13/152 | (2006.01) |
| D06M 101/32 | (2006.01) |
| G01N 33/00 | (2006.01) |
| D06M 101/06 | (2006.01) |

(52) U.S. Cl.
CPC ........ *D06M 13/152* (2013.01); *D06M 13/332* (2013.01); *D06M 13/335* (2013.01); *D06M 13/503* (2013.01); *D06M 15/687* (2013.01); *G01N 27/128* (2013.01); *D06M 2101/06* (2013.01); *D06M 2101/32* (2013.01); *D06M 2200/00* (2013.01); *G01N 27/126* (2013.01); *G01N 33/0037* (2013.01); *G01N 33/0044* (2013.01); *G01N 33/0054* (2013.01); *Y02A 50/20* (2018.01)

(56) References Cited

U.S. PATENT DOCUMENTS

| | | | | |
|---|---|---|---|---|
| 2013/0274087 | A1* | 10/2013 | da Silva Pinto | B01D 15/00 502/4 |
| 2013/0313193 | A1* | 11/2013 | Nair | B01D 53/228 210/650 |
| 2014/0015548 | A1* | 1/2014 | Naughton | G01N 27/3278 324/658 |
| 2017/0028390 | A1* | 2/2017 | Reynolds | B01J 23/72 |

OTHER PUBLICATIONS

Küsgens et al., Crystal Growth of the Metal-Organic Framework Cu3(BTC)2 on the Surface of Pulp Fibers. Adv. Eng. Mater. 2009, 11, 93-95.

Smith et al., Direct Self-Assembly of Conductive Nanorods of Metal-Organic Frameworks into Chemiresistive Devices on Shrinkable Polymer Films, Chemistry of Materials 2016 28 (15), 5264-5268.

Da Silva et al., In Situ Synthesis of a Cu-BTC Metal-Organic Framework (MOF 199) onto Cellulosic Fibrous Substrates: Cotton. Cellulose, 2012, 19, 1771-1779.

Meilikhov et al., Stepwise Deposition of Metal Organic Frameworks on Flexible Synthetic Polymer Surfaces, Dalton Trans. 2011, 40, 4838-4841.

Ozer et al., One-Step Growth of Isoreticular Luminescent Metal-Organic Frameworks on Cotton Fibers, RSC Adv. 2015, 5, 15198-15204.

Stoppa et al., Wearable Electronics and Smart Textiles: A Critical Review, Sensors 2014, 14, 11957-11992.

Abouraddy et al., Towards Multimaterial Multifunctional Fibres that See, Hear, Sense and Communicate, Nat. Mater. 2007, 6, 336-347.

Custodio et al., A Review on Architectures and Communications Technologies for Wearable Health-Monitoring Systems. Sensors 2012, 12, 13907-13946.

Coosemans et al., Integrating Wireless ECG Monitoring in Textiles, Sens. Actuators A Phys. 2006, 130-131, 48-53.

Yamada et al., A Stretchable Carbon Nanotube Strain Sensor for Human-Motion Detection, Nat. Nanotechnol. 2011, 6, 296-301.

Cai et al., Flexible Planar/Fiber-Architectured Supercapacitors for Wearable Energy Storage, J. Mater. Chem. C 2014, 2, 1184-1200.

Coyle et al. Smart Nanotextiles: A Review of Materials and Applications. MRS Bull. 2007, 32, 434-443.

Cherenack et al., Woven Electronic Fibers with Sensing and Display Functions for Smart Textiles, Adv. Mater. 2010, 22, 5178-5182.

Brozena et al., Atomic Layer Deposition on Polymer Fibers and Fabrics for Multifunctional and Electronic Textiles. J. Vac. Sci. Technol. A 2016, 34, 010801.

Zeng et al., Fiber-Based Wearable Electronics: A Review of Materials, Fabrication, Devices, and Applications, Adv. Mater. 2014, 26, 5310-5336.

Bedeloglu et al., A Photovoltaic Fiber Design for Smart Textiles, Text. Res. J. 2009, 80, 1065-1074.

Zhang et al., All-Textile Triboelectric Generator Compatible with Traditional Textile Process. Adv. Mater. Technol. 2016, 1, doi: 10.1002/admt.201600147.

* cited by examiner

FIG. 2A  textile swatch + metal salt + hexatropic ligand

FIG. 2B  SOFT swatch  Δ ↓ $H_2O$  MOF structure

| FIG. 2C | X | fabric | MOF | R (1 cm) |
|---|---|---|---|---|
| | O | cotton | $Ni_3HHTP_2$ | 2.8 ± 0.5 MΩ/cm² |
| | NH | cotton | $Ni_3HITP_2$ | 5.6 ± 2 MΩ/cm² |

FIG. 16A
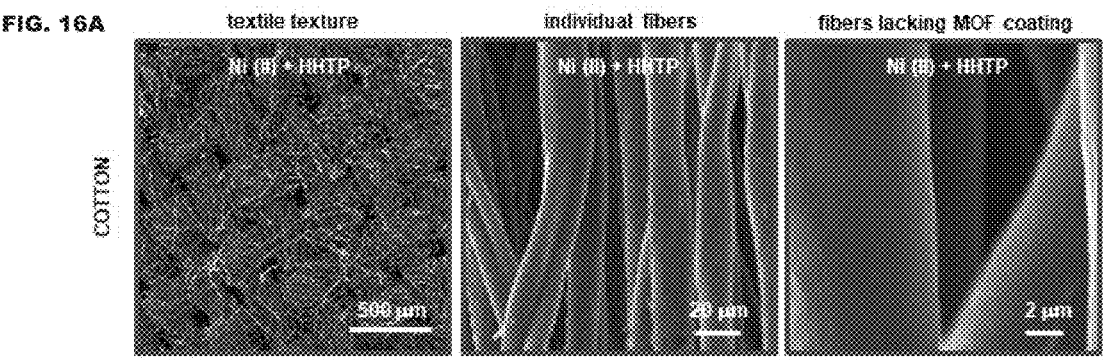
FIG. 16B
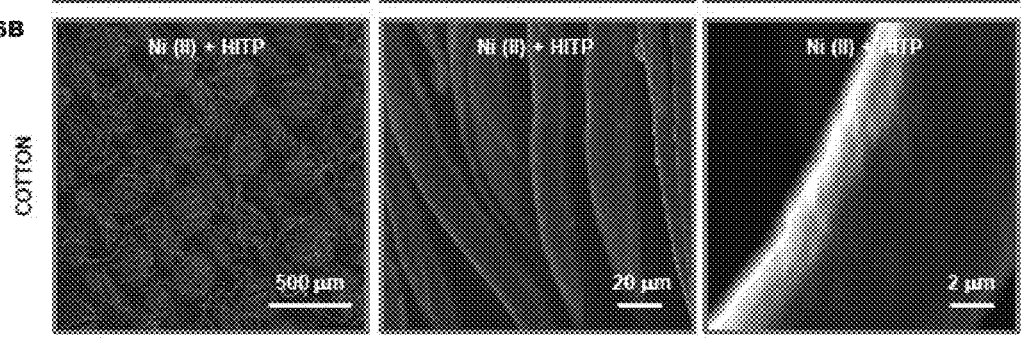
FIGURE 16

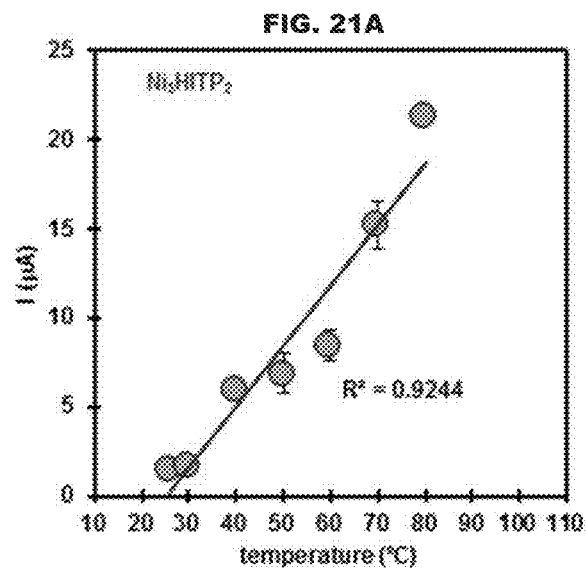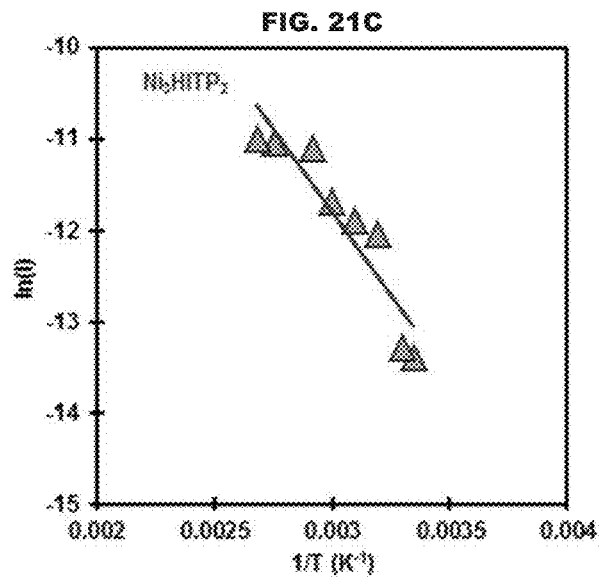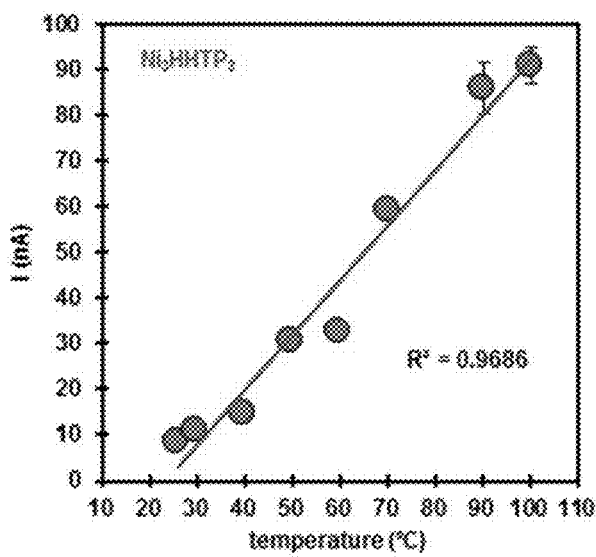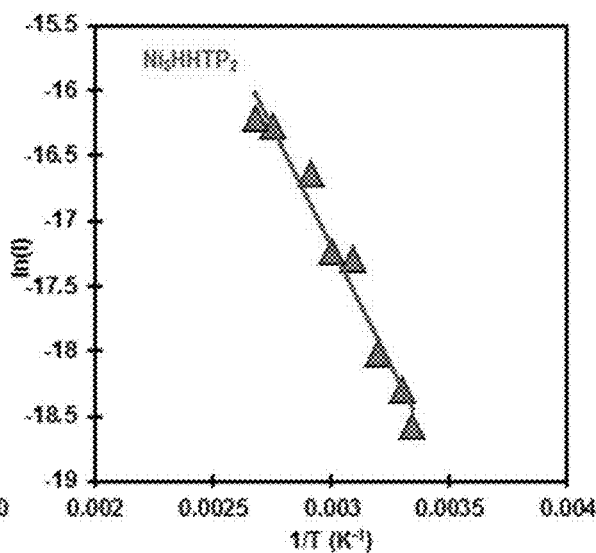
FIG. 21A
FIG. 21B
FIG. 21C
FIG. 21D

FIG. 22A
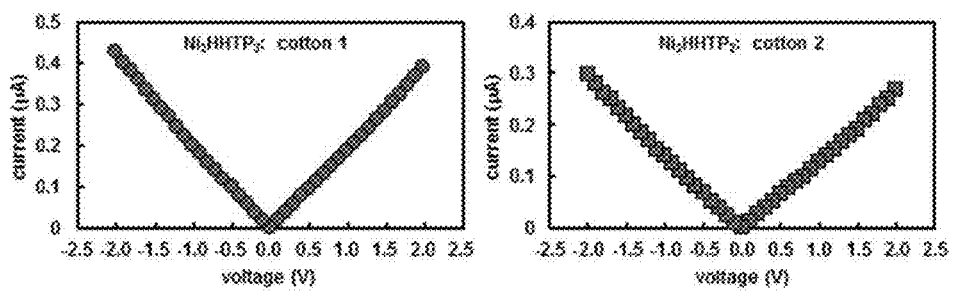
FIG. 22B
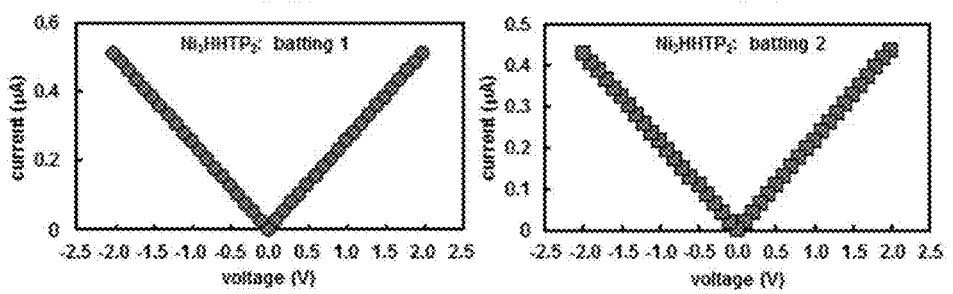
FIG. 22C
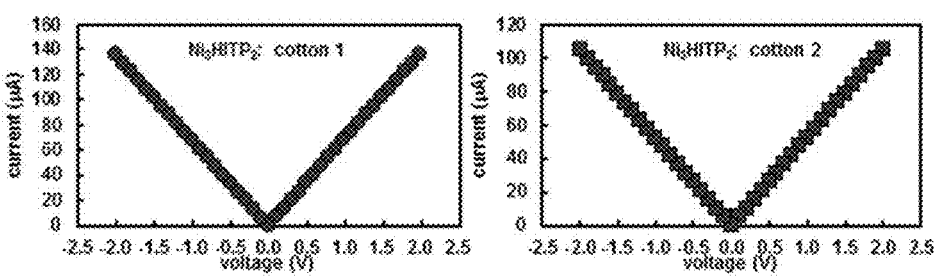
FIGURE 22

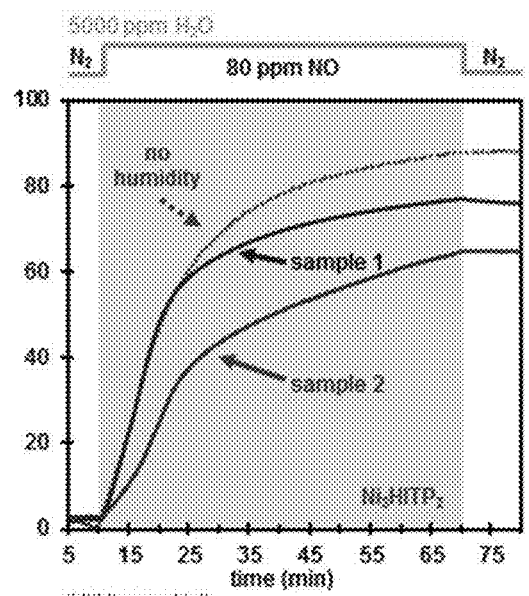
FIG. 32A
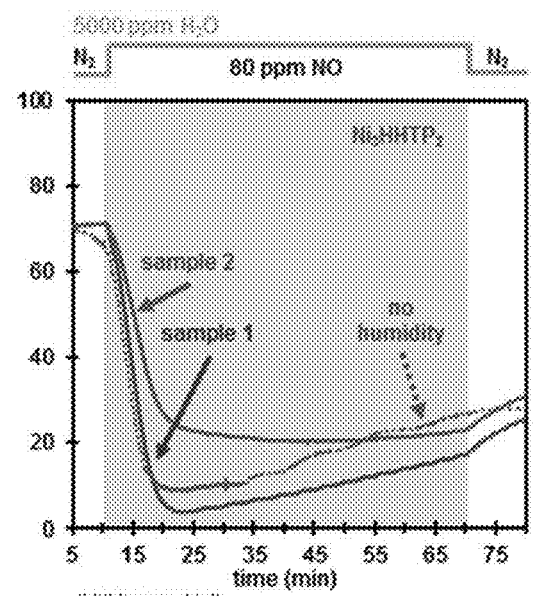
FIG. 32B
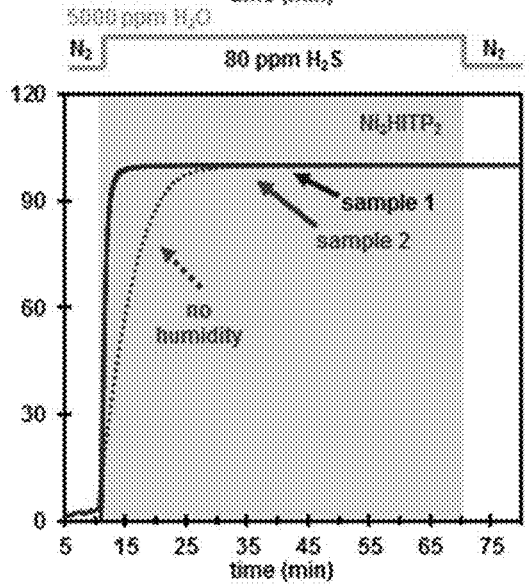
FIG. 32C
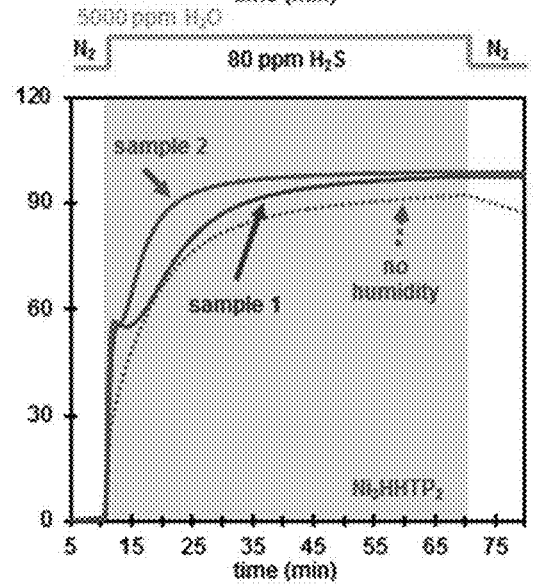
FIG. 32D
FIGURE 32

CONDUCTIVE TEXTILES AND USES THEREOF IN FUNCTIONAL DEVICES

CROSS-REFERENCE TO RELATED APPLICATIONS

This application claims priority to U.S. Provisional Patent Application No. 62/489,851, filed on Apr. 25, 2017. The entirety of the aforementioned application is incorporated herein by reference.

STATEMENT REGARDING FEDERALLY SPONSORED RESEARCH

This invention was made with government support under W911NF-17-1-0398 awarded by the Department of Defense. The government has certain rights in the invention.

BACKGROUND

Current electronic textiles (e-textiles) and smart fabric sensors (SFSs) have numerous limitations in terms of flexibility, tunability, conductivity, functional integrity, and efficient fabrication. Various embodiments of the present disclosure address the aforementioned limitations.

SUMMARY

In some embodiments, the present disclosure pertains to conductive textiles that include: a textile component with a plurality of fibers; and metal-organic frameworks associated with the fibers of the textile component in the form of a conductive network.

In some embodiments, the textile component includes a plurality of mesopores while the metal-organic frameworks include a plurality of micropores. In some embodiments, the metal-organic frameworks have a two-dimensional structure. In some embodiments, the metal-organic frameworks are in crystalline form.

In some embodiments, the metal-organic frameworks are conformally coated on the fibers of the textile component. In some embodiments, the metal-organic frameworks are in ohmic contact with the textile component. In some embodiments, the metal-organic frameworks constitute from about 5 wt % to about 50 wt % of the combined mass of the textile component and the metal-organic frameworks.

In some embodiments, the formed conductive network is in the form of a conductive pathway on the fibers of the textile component. In some embodiments, the conductive network includes a conductive surface area of at least 1 cm$^2$. In some embodiments, the conductive textile has a conductivity ranging from about 0.0001 S/cm to about 2.0 S/cm.

Additional embodiments of the present disclosure pertain to methods of sensing an analyte in a sample. In some embodiments, the methods of the present disclosure include the following steps: exposing the sample to a conductive textile of the present disclosure; and detecting the presence or absence of the analyte from the sample by detecting a change in a property of the conductive textile, and correlating the change in the property to the presence or absence of the analyte.

In some embodiments, the change in the property of the conductive textile includes a change in normalized conductance over time ($\Delta G/Go$). In some embodiments, the analyte to be detected includes one or more gases. In some embodiments, the one or more gases include, without limitation, NO, CO, $H_2S$, $NH_3$, $H_2O$, and combinations thereof.

In some embodiments, the sample is derived from a gaseous environment. In some embodiments, the exposure of the sample to the conductive textile occurs by flowing the sample through the conductive textile.

In some embodiments, the exposure of the sample to the conductive textile results in the reversible association of any analyte in the sample with the conductive textile. In some embodiments, the association also results in filtration, pre-concentration, and capture of the analyte.

In some embodiments, the methods of the present disclosure can be utilized to detect analytes at very low concentrations, such as concentrations of less than about 100 ppm. In some embodiments, the methods of the present disclosure can be utilized to detect a plurality of analytes. In some embodiments, the methods of the present disclosure can be utilized to detect analytes in a humid environment, such as an environment that has a relative humidity of 15% or higher.

In some embodiments, the methods of the present disclosure also include a step of releasing the analyte from the conductive textile. In some embodiments, the releasing occurs by washing the conductive textile. The conductive textile may then be used to sense additional analytes in a sample.

DESCRIPTION OF THE DRAWINGS

FIG. 2A shows the starting materials for SOFT-sensors from organic triphenylene-based ligand (HHTP or HITP), metallic node ($Ni(OAc)_2$ or $NiCl_2$), and fabric swatch (cotton shows no conductivity). Photograph of cotton swatch is shown. FIG. 2B shows that the solvothermal condensation of the aforementioned reagents in water produces conductive SOFT-devices: textiles coated with nanoporous MOF. Macroscopic through molecular level detail is shown, from a photograph of cotton SOFT-sensor post-reaction (top left), to scanning electron micrographs detailing MOF coating on fibers (bottom left) and characteristic MOF nanorod texture (bottom right), to space-filling model of MOF (top right). FIG. 2C summarizes sheet resistance measurements for SOFT-swatches.

FIG. 3A shows photographs of mechanical manipulation of as-synthesized SOFT-devices (4×1 cm cotton swatch shown for clarity). SOFT-devices are capable of withstanding twisting, bending, and wrapping around objects without significant changes in conductance, as demonstrated in the plots in FIGS. 3B and 3C. FIGS. 3B and 3C show the sheet resistance values of cotton SOFT-swatch (2×1 cm) upon mechanical manipulation for $Ni_3HHTP_2$ (FIG. 3B) and $Ni_3HITP_2$ (FIG. 3C), illustrating their consistent electronic performance under physical stress.

FIG. 4A shows custom enclosure for dosing SOFT-sensors with analytes. FIG. 4B shows a representative response for $Ni_3HITP_2$ (blue) and $Ni_3HITP_2$ (red) SOFT-sensors when exposed to (from left to right) NO or $H_2S$.

FIG. 4C shows a slope of first five minutes of sensor response versus concentration of analyte, in response to NO (left) and $H_2S$ (right).

FIG. 5A shows principle component analysis for arrays of (one each) $Ni_3HHTP_2$ and $Ni_3HITP_2$SOFT-sensors (triangle and diamond each represent single array) at saturation, showing capability for differentiating NO, $H_2S$, and $H_2O$. FIG. 5B summarizes saturation sensor response for $Ni_3HHTP_2$ (red) and $Ni_3HITP_2$ (blue) exposed to analytes (80 ppm NO and $H_2S$, left to right) in dry nitrogen (solid bars) and in the presence of 5000 ppm water (with water droplet), demonstrating consistent function between dry and humid (18% RH) environments.

FIG. 6A shows a custom Teflon enclosure used to determine membrane breakthrough for SOFT-devices. Two devices are loaded such that the diameter of the inner bore for gas flow is completely covered by SOFT-devices. Spring loaded gold pins immobilize the sensors and serve as electrodes. The enclosure is then completely sealed for leak-free flow. FIG. 6B shows representative breakthrough sensing traces for SOFT-devices. The first device exposed to analyte is represented by a solid line, the second device by a dashed line. The delayed response of the second device reflects gas capture by the first device.

FIG. 7A shows a TGA curve of $Ni_3HHTP_2$MOF filtered and dried from solution-phase synthesis. FIG. 7B shows a TGA curve of $Ni_3HHTP_2$MOF filtered and dried from solution of templated textile synthesis.

FIG. 8A shows a TGA curve of $Ni_3HITP_2$SOFT-device (solid blue trace) compared to plain cotton swatch (dashed black trace). FIG. 8B shows a TGA curve of $Ni_3HHTP_2$ SOFT-device (solid red trace) compared to plain cotton swatch (dashed black trace). Under nitrogen, both SOFT-devices are stable up to ~350° C., consistent with plain cotton.

FIG. 10A shows a TGA curve of $Ni_3HITP_2$ MOF filtered and dried from solution-phase synthesis. FIG. 10B shows a TGA curve of $Ni_3HITP_2$ MOF filtered and dried from solution of templated textile synthesis. The increased percent decomposition as compared to the bulk likely reflects small fibers that remained in the powder from the textile templation.

FIG. 11A shows powder X-ray diffraction (PXRD) traces for (top to bottom) cotton (black), incomplete SOFT-device based on cotton saturated with starting materials (brown), $Ni_3HHTP_2$ assembled on cotton (red), and bulk $Ni_3HHTP_2$ MOF (orange). FIG. 11B shows PXRD traces for (top to bottom) batting (black), $Ni_3HHTP_2$ assembled on batting (green), and bulk $Ni_3HHTP_2$ MOF (orange). FIG. 11C shows major Bragg planes present in each trace and their corresponding structural correlations. Note that the (100) major plane—perpendicular to the plane of the MOF sheet—is present in both completed SOFT-samples (see black arrow), but absent in the incomplete sample (shown in Part A) and in the substrate. This observation suggests long range crystalline order introduced by the MOF as it directly assembles onto the substrate fibers.

FIG. 13A shows PXRD traces for (top to bottom) cotton (black), incomplete SOFT-device based on cotton saturated with starting materials (gray), $Ni_3HITP_2$ assembled on cotton (blue) and bulk $Ni_3HITP_2$ MOF (pink). Relevant Bragg planes are highlighted in gray. FIG. 13B shows major Bragg planes present in each trace and their corresponding structural correlations. There is significant peak overlap between the cotton substrate, SOFT-control, and SOFT-device. The most noteworthy change is shown in attenuation of the cotton peak at 23° with respect to sharper peaks.

FIG. 14A shows the SEMs of bulk $Ni_3HHTP_2$ MOF synthesized using the conditions described in Example 1 without fabric swatches present in the synthesis at multiple locations within the sample, illustrating representative observed crystallite formations and morphology. FIG. 14B shows the SEMs of $Ni_3HHTP_2$ MOF solid filtered from textile synthesis (both cotton and batting combined) imaged at multiple locations within the sample, illustrating the consistency between bulk MOF and MOF prepared with textile present in the synthesis.

FIG. 15A shows the SEMs of bulk $Ni_3HITP_2$ MOF synthesized using the conditions described in Example 1 without fabric swatches present in the synthesis at multiple locations within the sample, illustrating representative observed crystallite formations and morphology. FIG. 15B shows the SEMs of $Ni_3HITP_2$ MOF solid filtered from textile synthesis imaged at multiple locations within the sample, illustrating the consistency between bulk MOF and MOF prepared with textile present in the synthesis.

FIG. 16 shows SEMs of incomplete SOFT-devices, prepared as described in Example 1. FIG. 16A shows the SEMs of a fabric swatch saturated with a mixture of nickel (II) salt and HHTP organic ligand, following the procedure for direct self-assembly of MOFs on textiles, except sonicating for only 1 minute, then removing the swatches after holding the reaction at ambient temperature for 5 minutes, to ensure that MOF crystallization was minimal. FIG. 16B shows the SEMs of fabric swatches saturated with a mixture of nickel (II) salt and HITP organic ligand, with minimal MOF crystallization. Both samples were non-conductive, and showing no observable MOF crystallites, implying that direct self-assembly and conformal crystallization is essential for producing SOFT-devices. Lack of sample conductivity led to sample charging, accounting for the difficulties in focusing at high magnifications.

FIG. 20A shows an isotherm and BET surface area (SA) for unadulterated cotton (gray). Since cotton has such a low surface area, the required adsorptive (krypton) limited the BET analysis to surface area assessment. Degas=120° C. under vacuum ($3\times10^{-5}$ 1/Torr), 24 h. FIG. 20B shows summarized BET surface areas for all samples.

FIGS. 21A and 21B show current versus temperature plots, best fit lines, and $R^2$ values for $Ni_3HITP_2$ SOFT-device (FIG. 21A) and $Ni_3HHTP_2$ device (FIG. 21B), illustrating the semiconductive character of SOFT-devices (as temperature increases, resistance decreases).

FIGS. 21C and 21D show a natural log of current versus inverse temperature plots for $Ni_3HITP_2$ SOFT-device and $Ni_3HHTP_2$. Linear regression of the plots provides thermal band gap, as calculated using Eq. 2 in Example 1.

FIG. 22 shows various IV plots. FIG. 22A shows IV plots for two representative swatches (1 and 2) demonstrating Ohmic nature of contacts for $Ni_3HHTP_2$ on cotton. FIG. 22B shows IV plots for two representative swatches (1 and 2) demonstrating Ohmic nature of contacts for $Ni_3HHTP_2$ on batting. FIG. 22C shows IV plots for two representative swatches (1 and 2) demonstrating Ohmic nature of contacts for $Ni_3HITP_2$ on cotton.

FIG. 23A shows a photo of large (5×5 cm) SOFT-sensor swatch post-synthesis. This swatch is cotton with $Ni_3HHTP_2$ MOF. FIG. 23B shows cartoon of point-to-point resistance measurements and resistance values in mega-ohms. The resistance is indistinguishable on both faces of the swatch.

FIG. 24A shows a cartoon procedure for custom device architecture by painting with conductive silver paint. Using this method, Applicants produced SOFT-sensors equipped with metal electrodes that are confined to one side of the SOFT-sensor. FIG. 24B shows cartoon procedure for custom device architecture by sewing electrodes using conductive (steel-impregnated) threads, producing SOFT-sensors equipped with flexible electrodes that are fully reversible (back-to-front).

FIG. 25A shows that the areas where MOF growth was not desired were patterned with petroleum jelly from a syringe. The jelly was then melted into the fabric (cotton is pictured) at 40° C. FIG. 25B shows that electrodes were added (sewn conductive threads are pictured), which was followed by MOF assembly ($Ni_3HHTP_2$ is pictured). FIG. 25C shows that the resulting SOFT-array was washed thoroughly with water, acetone, and petroleum ether. FIG. 25D shows point-to-point resistance measurements for each device within the array. Resistance measurements were taken from thread to thread for devices ii-vi. The resistance was infinite for point-to-point measurement along the full array (i), demonstrating that the patterning prevented bridging across devices. The measurements shown are for pictured array.

FIG. 31A shows a saturation curve for exposure of $Ni_3HHTP_2$ (red) and $Ni_3HITP_2$ (blue) to water vapor (5000 ppm). FIG. 31B shows representative dosing/recovery sensing traces (4×1000 ppm $H_2O$) for $Ni_3HITP_2$ (blue) and $Ni_3HHTP_2$ (red). Vapor is diluted in dry nitrogen. FIG. 31C shows the overall percent responses (4×1000 ppm) for two separate batches of SOFT-sensors, demonstrating the device: device reproducibility. Error bars represent the standard deviation from the average (4 exposures).

FIG. 32 shows chemiresistive response of SOFT-devices equilibrated in water vapor (5000 ppm) and dosed with analyte diluted in humid $N_2$ (5000 ppm $H_2O$). Shown are saturation curves for two $Ni_3HITP_2$ devices (blue, solid) (FIG. 32A) and two $Ni_3HHTP_2$ devices (red) to NO (80 ppm) (FIG. 32B), with humid nitrogen serving as a carrier gas (5000 ppm $H_2O$). These traces are compared to standard curves collected in dry nitrogen (dashed lines). Also shown are saturation curves for two $Ni_3HITP_2$ devices (blue, solid) (FIG. 32C) and two $Ni_3HHTP_2$ devices (red) to $H_2S$ (80 ppm) (FIG. 32D), with humid nitrogen serving as a carrier gas (5000 ppm $H_2O$). These traces are compared to standard curves collected in dry nitrogen (dashed lines). SOFT-devices are capable of sensing these analytes in humid environments with no significant differences from dry environments.

Figure 33:
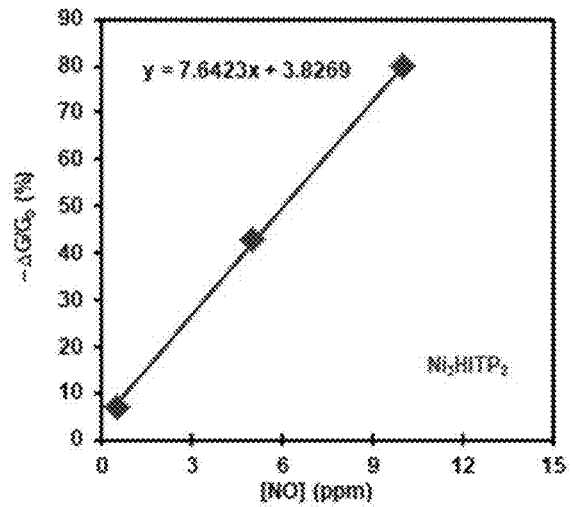
Figure 33:
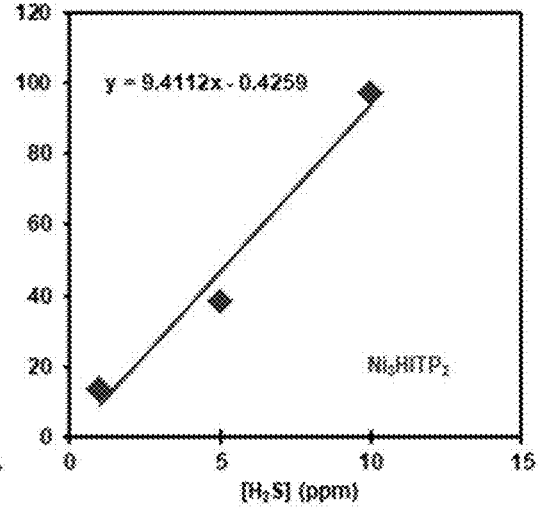
Figure 33:
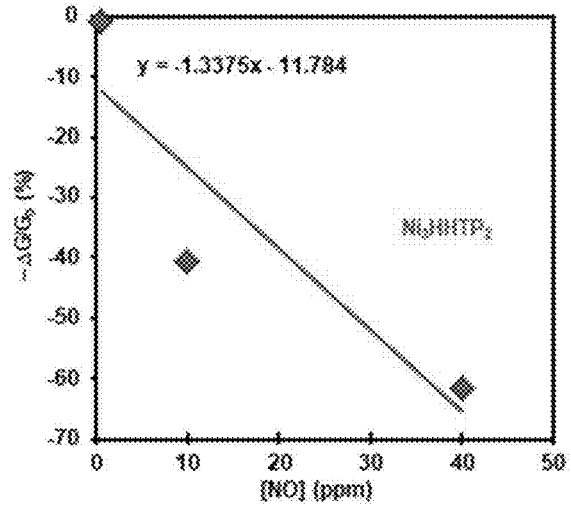
Figure 33:
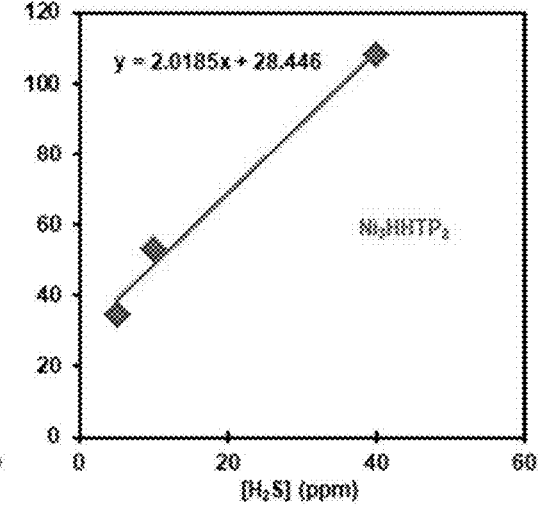

FIG. 33 shows linear range of maximum change in normalized conductance ($-\Delta G/G_o$) versus analyte concentration for $Ni_3HITP_2$ exposed to NO (FIG. 33A), $Ni_3HITP_2$ exposed to $H_2S$ (FIG. 33B), $Ni_3HHTP_2$ exposed to NO (FIG. 33C), and $Ni_3HHTP_2$ exposed to $H_2S$ (FIG. 33D).

Figure 34:
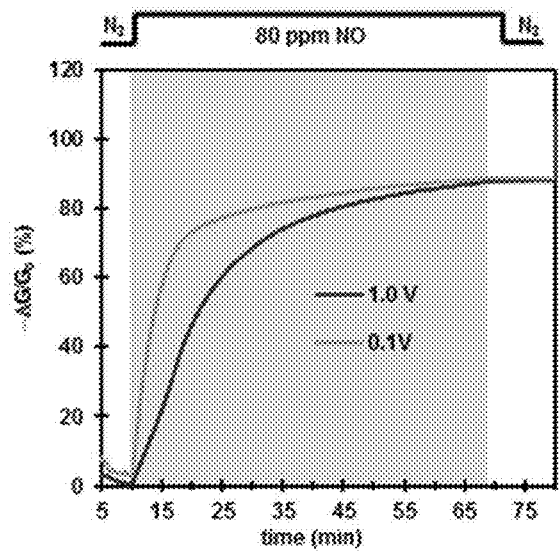
Figure 34:
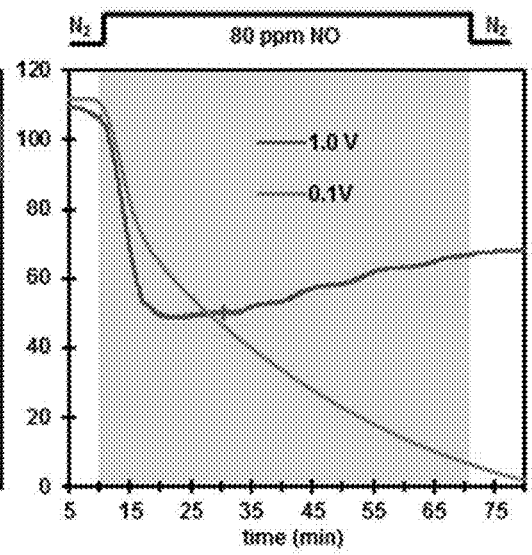
Figure 34:
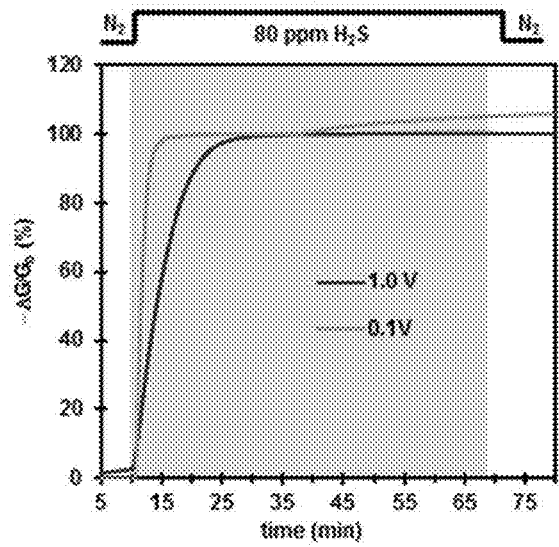
Figure 34:
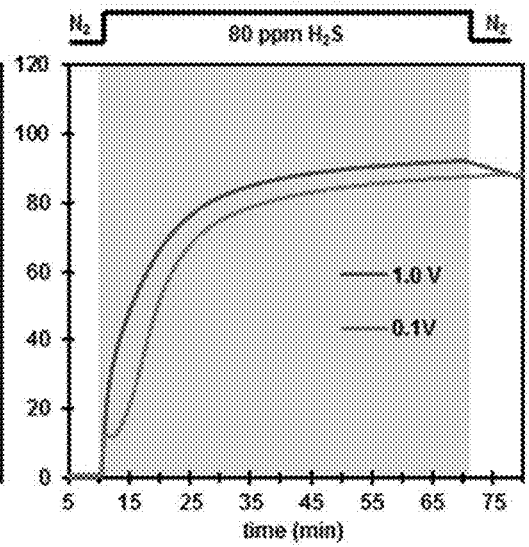

FIG. 34 shows representative saturation traces for SOFT-devices at differing applied voltages. Shown are saturation curves at 1.0 V and 0.1 V for $Ni_3HITP_2$ devices (blue, I=0.5-2.0 nA) (FIG. 34A) and $Ni_3HHTP_2$ devices (red, I=0.2-1.5 µA) (FIG. 34B) to NO (80 ppm). Also shown are saturation curves at 1.0 V and 0.1 V for $Ni_3HITP_2$ devices (blue, I=0.5-1.5 nA) (FIG. 34C) and $Ni_3HHTP_2$ devices (red, I=0.05-0.2 µA) (FIG. 34D) to $H_2S$ (80 ppm).

Figure 35:
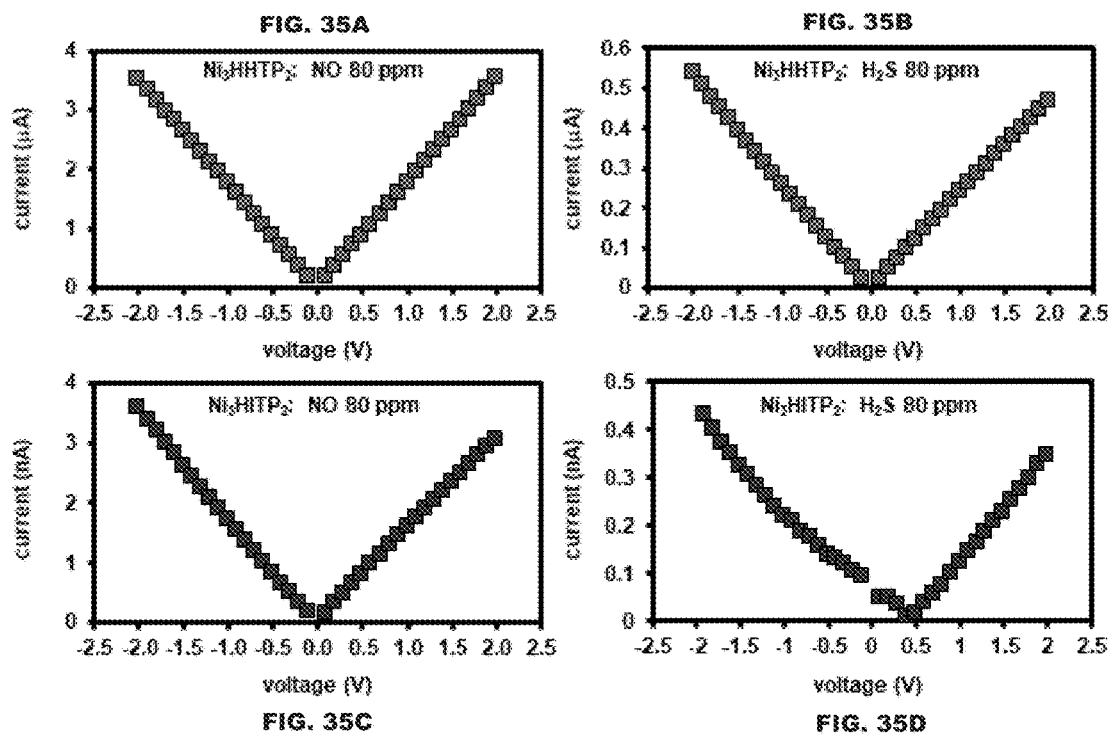

FIG. 35 shows IV plots for a representative SOFT-devices demonstrating Ohmic nature of contacts (in the range of −2:2 V) of $Ni_3HHTP_2$ during exposure to NO (80 ppm) (FIG. 35A) and $H_2S$ (80 ppm) (FIG. 35B), and of $Ni_3HITP_2$ during exposure to NO (80 ppm) (FIG. 35C) and $H_2S$ (80 ppm) (FIG. 35D). For these experiments, devices were allowed to saturate in analyte vapors, then changes in voltage were applied.

Figure 36:
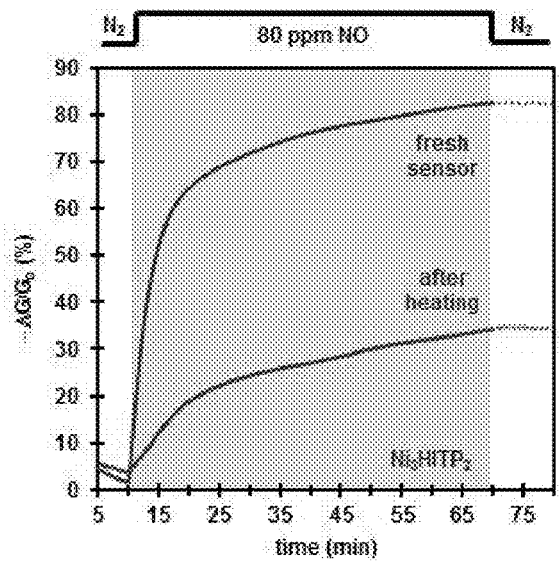
Figure 36:
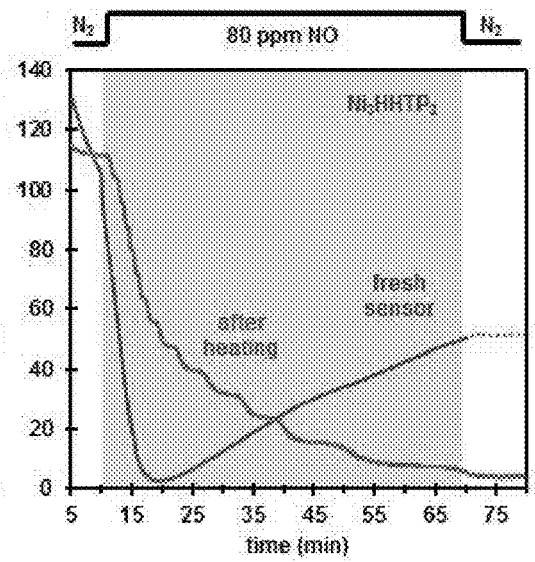
Figure 36:
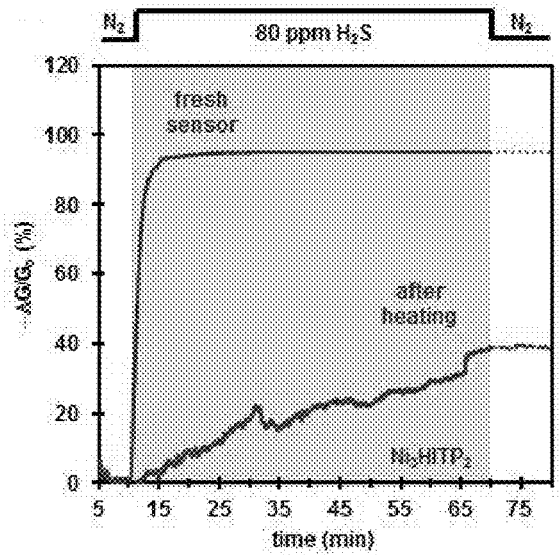
Figure 36:
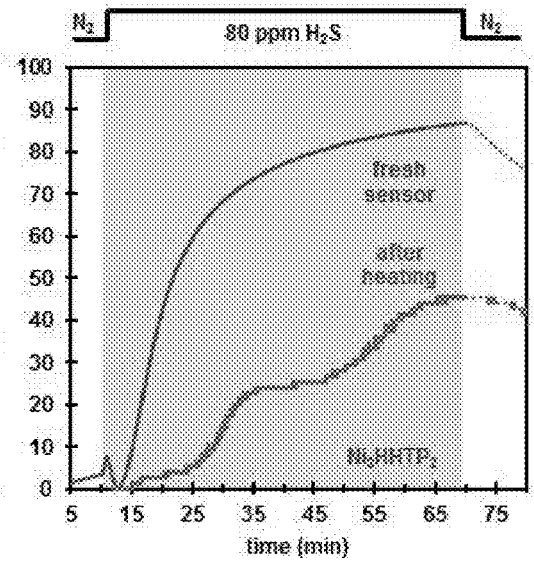

FIG. 36 shows sensor performance before and after heating (60° C.) overnight under high vacuum for $Ni_3HITP_2$ saturated with NO (80 ppm) (FIG. 36A), $Ni_3HHTP_2$ saturated with NO (80 ppm) (FIG. 36B), $Ni_3HITP_2$ saturated with $H_2S$ (80 ppm) (FIG. 36C), and $Ni_3HHTP_2$ saturated with $H_2S$ (80 ppm) (FIG. 36D).

Figure 37:
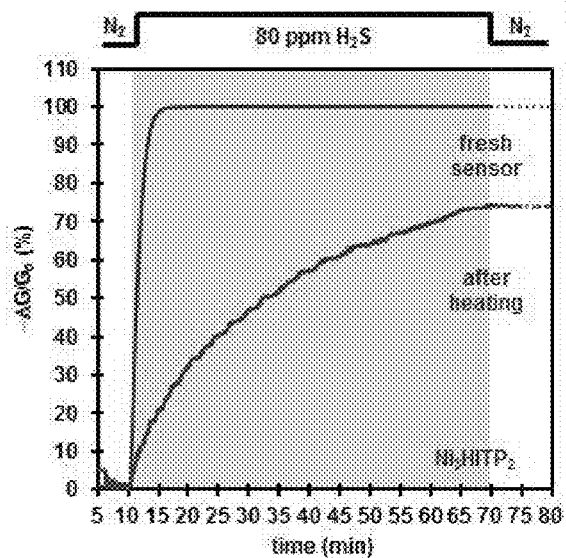
Figure 37:
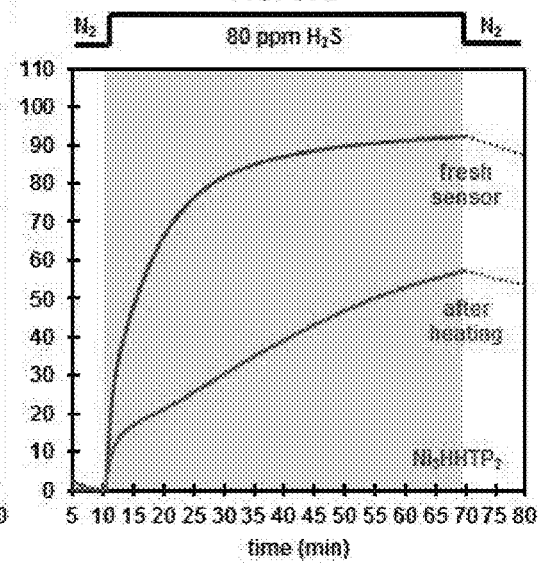

FIG. 37 shows sensing traces displaying limited thermal recovery for cotton SOFT-sensors. FIG. 37A shows $Ni_3HITP_2$ saturated with $H_2S$ (80 ppm). After heating the same device (80° C., 1 h), the SOFT-sensor responds to a second saturation exposure with >70% performance with respect to fresh devices. FIG. 37B shows $Ni_3HHTP_2$ saturated with $H_2S$ (80 ppm). After heating the same device (80° C., 1 h), the SOFT-sensor responds to a second saturation exposure with >60% performance with respect to fresh devices.

Figure 38:
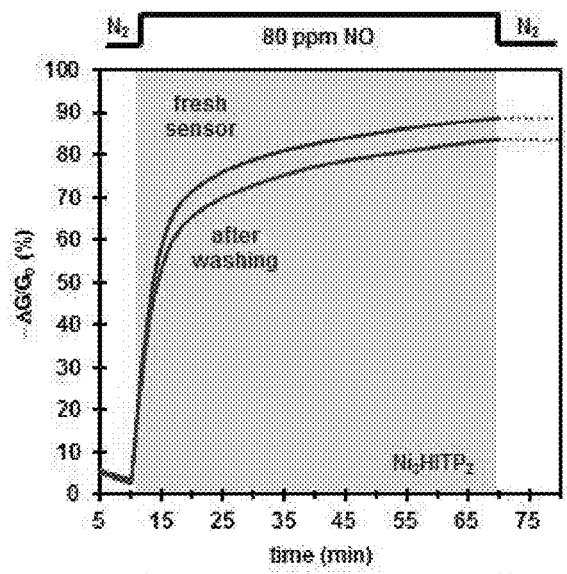
Figure 38:
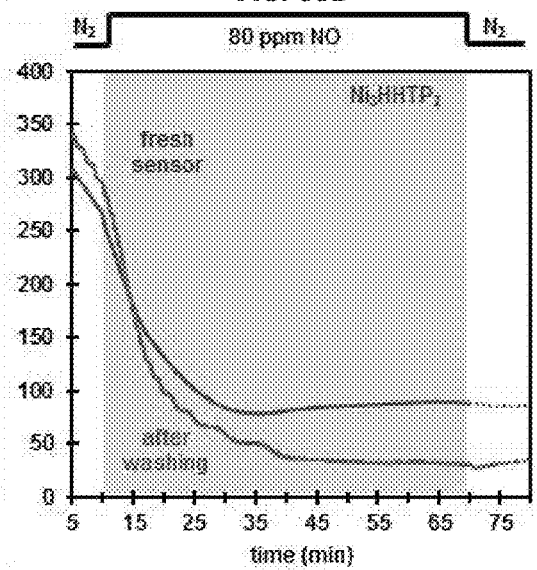
Figure 38:
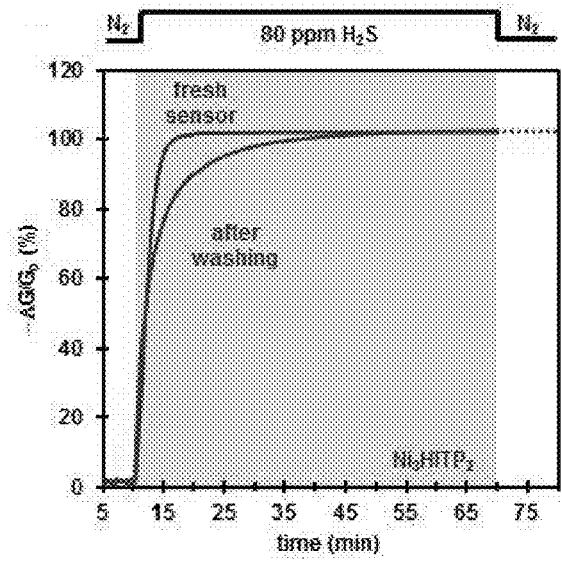
Figure 38:
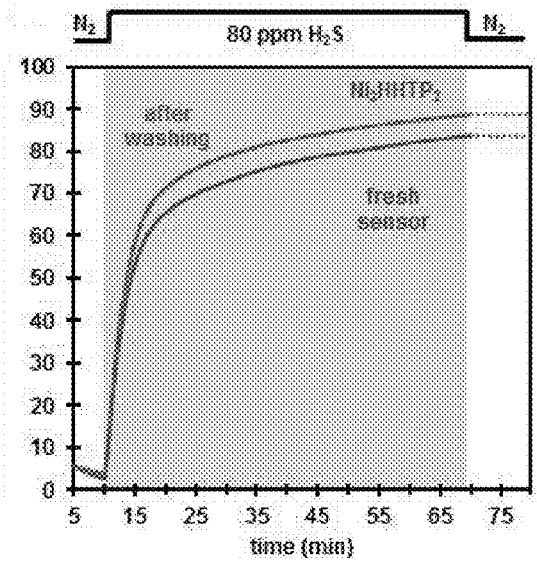

FIG. 38 shows sensor performance before and after washing in $H_2O$ and drying in atmospheric air. Used devices were soaked in water for 5 minutes, then allowed to drip dry overnight. FIG. 38A shows $Ni_3HITP_2$ saturated with NO (80 ppm). FIG. 38B shows $Ni_3HHTP_2$ saturated with NO (80 ppm). FIG. 38C shows $Ni_3HITP_2$ saturated with $H_2S$ (80 ppm). FIG. 38D shows $Ni_3HHTP_2$ saturated with $H_2S$ (80 ppm). In each case, devices exhibited a full recovery (within error).

Figure 39:
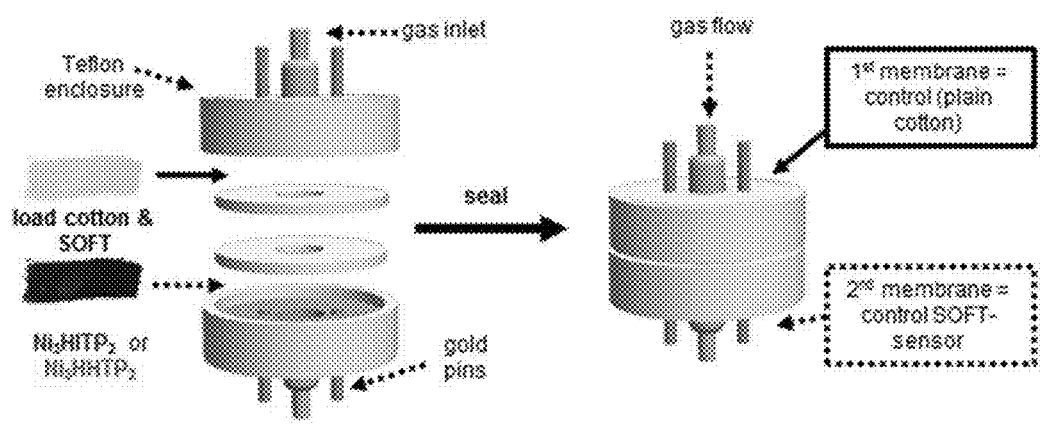

FIG. 39 shows an experimental setup for control experiments for breakthrough study. A single SOFT-device was placed in the second sample holder, with a swatch of non-conductive plain cotton (the same textile used in the device fabrication) in the first sample holder, such that the gas stream must pass through the plain cotton to reach the SOFT-sensor.

Figure 40:
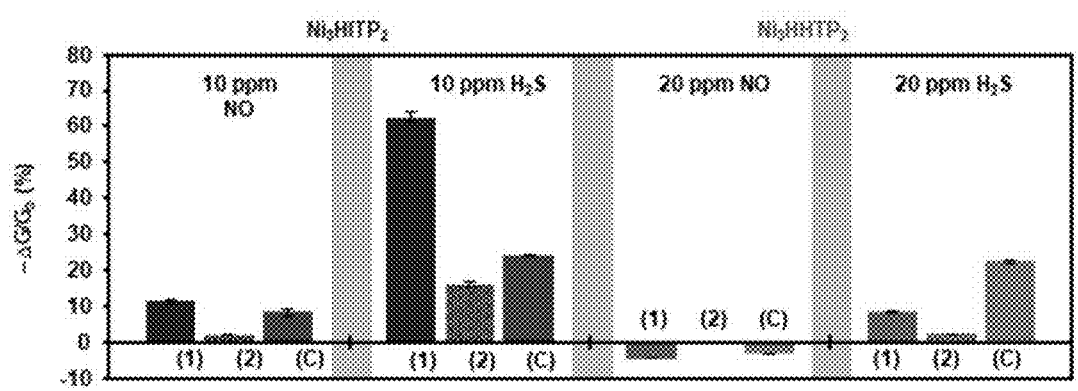

FIG. 40 summarizes values of sensor response ($-\Delta G/G_o$) at 10 minutes for breakthrough experiments compared to control (C).

Figure 41:
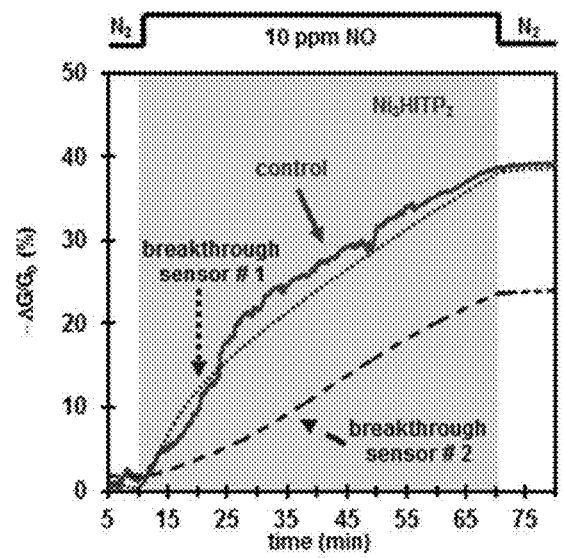
Figure 41:
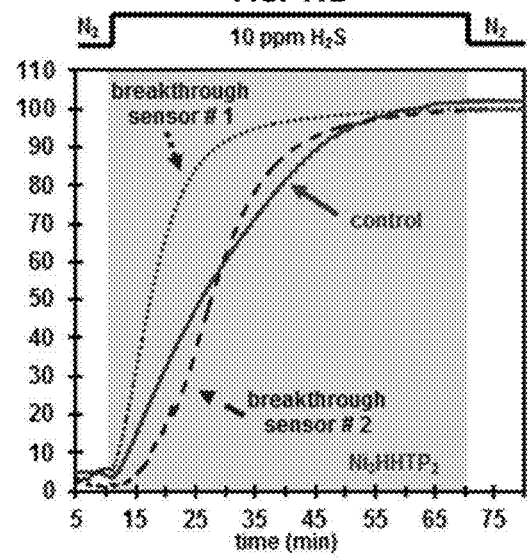
Figure 41:
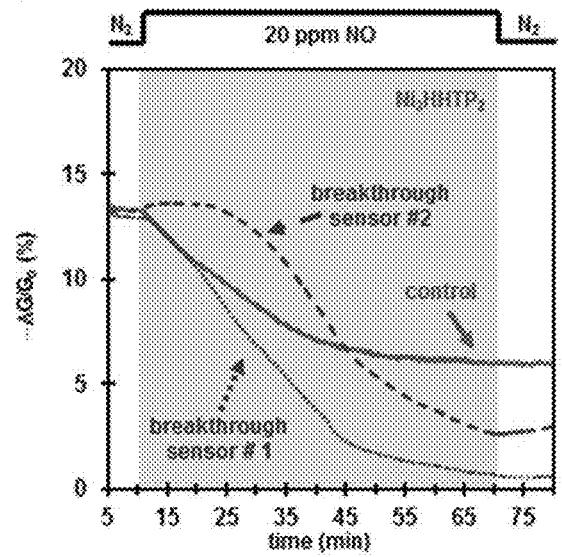
Figure 41:
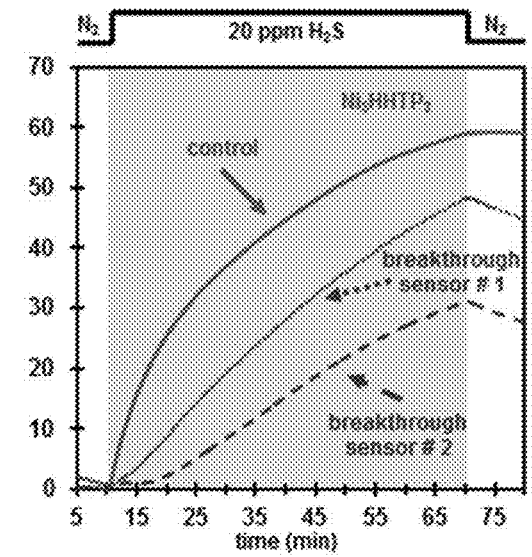

FIG. 41 shows control experiments for breakthrough studies using the experimental setup from FIG. 39. Control devices are shown as solid lines, while dashed lines represent devices in the breakthrough setup. FIG. 41A shows $Ni_3HITP_2$ SOFT-sensor as a control device (solid blue), with only plain cotton first exposed to 10 ppm NO, compared to breakthrough traces for both sensors in the first (dotted line), and second (thick dashed line) positions. FIG. 41B shows $Ni_3HITP_2$ SOFT-sensor as a control device (solid blue), with only plain cotton first exposed to 10 ppm $H_2S$, compared to breakthrough traces. FIG. 41C shows $Ni_3HHTP_2$ SOFT-sensor as a control device (solid red), with only plain cotton first exposed to 20 ppm NO, compared to breakthrough traces. FIG. 41D shows $Ni_3HHTP_2$ SOFT-sensor as a control device (solid red), with only plain cotton first exposed to 20 ppm $H_2S$, compared to breakthrough traces.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Wearable electronics hold promise in enhancing health monitoring, alleviating disability, and tracking environmental pollution. Electronic textiles (e-textiles) have the potential to advance the impact of wearable electronics through breathable and versatile devices and garments capable of electronically-transduced interactions with the local environment. This electronic signal transduction can be harnessed to create smart fabric sensors (SFSs) that report applied pressure, strain, heart rate, or presence of a chemical.

While physical SFSs typically rely on the flexibility and tunability of the fabric platform to enhance device performance, chemical SFSs often employ fiber-integrated stimuli-responsive materials (e.g., conductive polymers, carbon nanotubes, and graphene) that either do not affect or diminish the sensing response when compared to other substrates. A movement toward developing SFS technology based on synergy rather than compromise (i.e., where the sensor performance is enhanced by the textile platform) is a desired step in expanding the scope and practical viability of wearable chemical sensors.

An emerging class of conductive multifunctional nanomaterials based on metal-organic frameworks (MOFs) holds remarkable potential in electronic applications as chemiresistors, supercapacitors, and electrocatalysts. These porous, d-π conjugated, and crystalline frameworks can be prepared through modular bottom-up self-assembly of organic ligands with metallic nodes to generate extended conductive solid-state materials.

Interfacing non-conductive MOFs with fibers and fabrics, polymers, nanoparticles, biomaterials, and chemically-modified supports is well documented. Various methods have been utilized to produce such hybrid systems with enhanced function in selective chemical separation, sequestration, filtration, resistance to biofouling, stabilization of biomolecules, and controlled release of catalysts. Moreover, introduction of lithographic and ink-jet printing techniques can create patterns of surface-attached MOFs with controlled lateral resolution with potential utility in solid-state devices.

Many of these hybrid systems, however, are not conductive. Consequently, such systems are incapable of direct electronic transduction. In fact, introducing continuous conductivity while maintaining the functional integrity of the textile platform requires integration of conductive materials at the fiber level.

Moreover, even though the fabrication of multifunctional conductive nanomaterials have served as productive targets for developing SFSs, their deposition strategies are often limited in continuous fiber-scale integration or require specialized instrumentation. As such, a strategy that maintains the simplicity of bottom-up deposition while achieving conformal fiber-scale integration of conductive sensor materials-such as direct self-assembly from molecular components is highly desirable.

In sum, a need exists for more effective systems and methods for integrating conductive metal-organic frameworks with textiles for numerous applications, including enhanced performance in portable and flexible sensors. Various embodiments of the present disclosure address the aforementioned need.

Figure 1A:
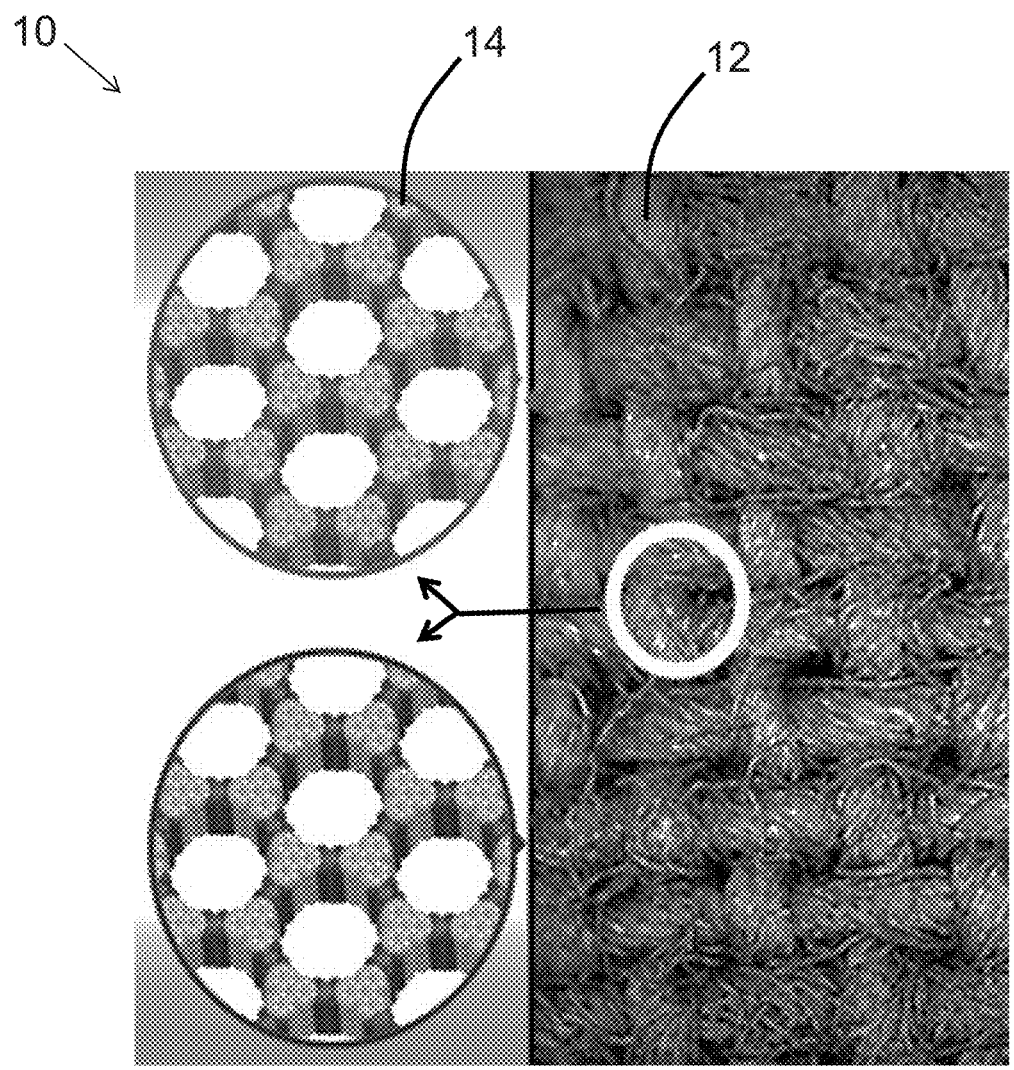
FIG. 1A depicts a conductive textile in accordance with an embodiment of the present disclosure.

In some embodiments, the present disclosure pertains to conductive textiles that include a textile component with a plurality of fibers, and metal-organic frameworks associated with the fibers in the form of a conductive network. In some embodiments illustrated in FIG. 1A, the conductive textiles of the present disclosure are in the form of conductive textile 10, which includes textile component 12 with a plurality of fibers, and metal-organic frameworks 14 associated with the fibers in the form of a conductive network.

Figure 1B:
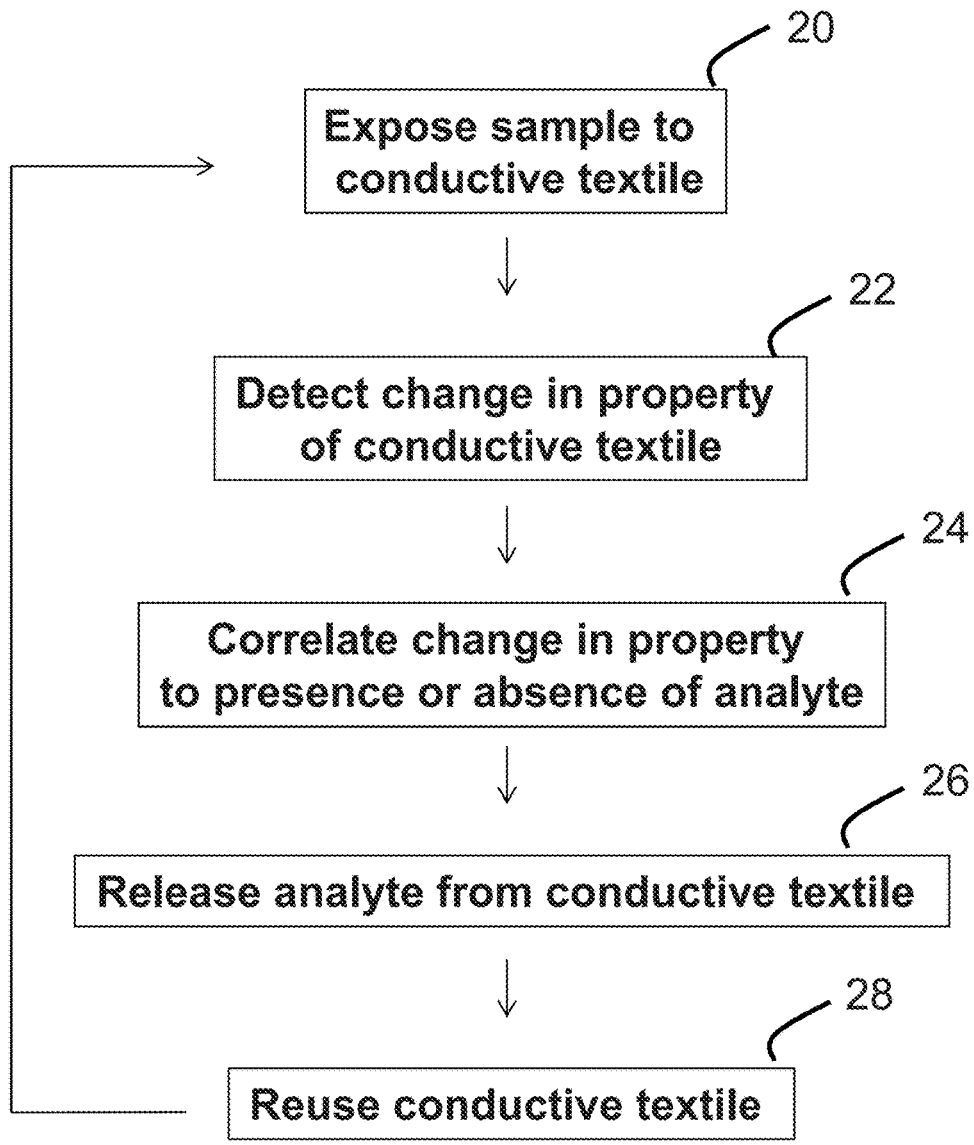
FIG. 1B illustrates a method of sensing an analyte by utilizing the conductive textiles of the present disclosure.

Additional embodiments of the present disclosure pertain to methods of sensing an analyte in a sample by utilizing the conductive textiles of the present disclosure. In some embodiments illustrated in FIG. 1B, the methods of the present disclosure include a step of exposing a sample to a conductive textile of the present disclosure (step 20). Thereafter, the presence or absence of the analyte from the sample is detected by detecting a change in a property of the conductive textile (step 22) and correlating the change in the property to the presence or absence of the analyte (step 24). In some embodiments, the methods of the present disclosure also include a step of releasing the analyte from the conductive textile (step 26). In some embodiments, the methods of the present disclosure also include a step of reusing the conductive textile to sense additional analytes (step 28).

Further embodiments of the present disclosure pertain to methods of making the conductive textiles of the present disclosure by associating metal-organic frameworks with a textile component. In some embodiments, the metal-organic frameworks may self-assemble on a textile component.

As set forth in more detail herein, the methods and conductive textiles of the present disclosure can have numerous embodiments. For instance, the conductive textiles of the present disclosure can include various textile components, metal-organic frameworks, and structures. Moreover, the metal-organic frameworks may be in the form of various types of conductive networks. Furthermore, various methods may be utilized to sense various analytes in various samples by the conductive textiles of the present disclosure. Various methods may also be utilized to make the conductive textiles of the present disclosure.

Conductive Textiles

As set forth in more detail herein, the conductive textiles of the present disclosure can include various textile components and metal-organic frameworks. Moreover, metal-organic frameworks may be associated with textile components in various manners to form various conductive networks. In addition, the conductive textiles may have various advantageous properties.

Textile Components

The conductive textiles of the present disclosure can include various types of textile components. For instance, in some embodiments, the textile components include, without limitation, synthetic textiles, poly-ester based textiles, poly-batting based textiles, natural textiles, cotton-based textiles, wool, fabrics, fabric swatches, cotton, commercial textiles, natural woven cotton fabric, non-woven polyester batting, and combinations thereof. In some embodiments, the textile components include natural textiles, such as cotton. In some embodiments, the textile components include synthetic textiles, such as polyester-based textiles. The use of additional textiles can also be envisioned.

The textile components of the present disclosure can include various structures. For instance, in some embodiments, the fibers of the textile component are in the form an interwoven network (e.g., the interwoven network shown in FIG. 1A for textile component 12). In some embodiments, the fibers of the textile component are in the form of aligned fibers. Additional textile component structures can also be envisioned.

In some embodiments, the textile components of the present disclosure have a porous structure. For instance, in some embodiments, the textile component includes a plurality of mesopores that have diameters ranging from about 2 nm to about 50 nm. In some embodiments the textile component includes a plurality of macropores that have diameters of more than about 50 nm.

Metal-Organic Frameworks

The conductive textiles of the present disclosure can include various types of metal-organic frameworks. In general, metal-organic frameworks include one or more metals and one or more organic ligands coordinated with the one or more metals.

The metal-organic frameworks of the present disclosure can include various types of organic ligands. For instance, in some embodiments, the organic ligands include, without limitation, hexatropic ligands, polydentate functional groups, aromatic ligands, phthalocyanine-based ligands, metallophthalocyaline-based ligands, naphthalocyanine-based ligands, triphenylene-based ligands, triphenylene derivatives, hexahydroxytriphenylene-based organic linkers, hexaiminotriphenlyene-based organic linkers, and combinations thereof.

In some embodiments, the one or more organic ligands include triphenylene-based ligands. In some embodiments, the triphenylene-based ligands include, without limitation, 2,3,5,6,10,11-hexahydroxytriphenylene (HHTP), 2,3,5,6,10,11-hexaiminotriphenylene (HITP), and combinations thereof.

The metal-organic frameworks of the present disclosure can also include various types of metals. For instance, in some embodiments, the metals include, without limitation, transition metals, iron, nickel, copper, cobalt, zinc, manganese, platinum, palladium, gold, bismuth, and combinations thereof.

The metal-organic framework metals may be in various forms. For instance, in some embodiments, more than one type of metal may be used at once within the same metal-organic framework. In some embodiments, the metal-organic framework metals may be in the form of at least one of metal ions, metal clusters, metallic nodes, metal catecholates, metal salts, and combinations thereof.

In more specific embodiments, the one or more metal-organic framework metals include nickel. In some embodiments, the nickel may be in the form of at least one of nickel (II) nodes, $Ni(OAc)_2$, $NiCl_2$, and combinations thereof.

Various organic ligands and metals may be combined to form various metal-organic frameworks. For instance, in some embodiments the metal-organic frameworks of the present disclosure include, without limitation, polyfunctional 2,3,5,6,10,11-hexahydroxytriphenylene (HHTP), 2,3,5,6,10,11-hexaiminotriphenylene (HITP) condensed in a 2:3 ratio with nickel (II) nodes ((Ni3HHTP2 and Ni3HITP2, respectively), and combinations thereof.

The metal-organic frameworks of the present disclosure can include various structures. For instance, in some embodiments, the metal-organic frameworks of the present disclosure have a porous structure. In some embodiments, the metal-organic frameworks of the present disclosure include a plurality of micropores that have diameters of less than about 2 nm.

In some embodiments, the metal-organic frameworks of the present disclosure have a two-dimensional structure. In some embodiments, the metal-organic frameworks of the present disclosure are in the form of a packed network.

In some embodiments, the metal-organic frameworks of the present disclosure are in crystalline form. For instance, in some embodiments, the metal-organic frameworks include a long range crystalline order. In some embodiments, the metal-organic frameworks are in the form of crystallites. In some embodiments, the metal-organic frameworks are in the form of porous and ordered crystalline frameworks. In some embodiments, the metal-organic frameworks are in the form of porous coordination polymers with limited or no crystallinity.

The metal-organic frameworks of the present disclosure may also have various shapes. For instance, in some embodiments, the metal-organic frameworks are in the form of nanorods. In some embodiments, the metal-organic frameworks are in the form of rod-like crystallites. In some embodiments, the metal-organic frameworks can be in the form of sheets or irregular shapes.

The conductive textiles of the present disclosure can have various amounts of metal-organic frameworks. For instance, in some embodiments, the metal-organic frameworks constitute from about 5 wt % to about 50 wt % of the combined mass of the textile component and the metal-organic frameworks. In some embodiments, the metal-organic frameworks constitute from about 10 wt % to about 40 wt % of the combined mass of the textile component and the metal-organic frameworks. In some embodiments, the metal-organic frameworks constitute from about 16 wt % to about 30 wt % of the combined mass of the textile component and the metal-organic frameworks. In some embodiments, the metal-organic frameworks constitute from about 17 wt % to about 37 wt % of the combined mass of the textile component and the metal-organic frameworks.

In some embodiments, the metal-organic frameworks constitute from about 5 wt % to about 25 wt % of the combined mass of the textile component and the metal-organic frameworks. In some embodiments, the metal-organic frameworks constitute from about 5 wt % to about 10 wt % of the combined mass of the textile component and the metal-organic frameworks. In some embodiments, the metal-organic frameworks constitute from about 7 wt % to about 8 wt % of the combined mass of the textile component and the metal-organic frameworks. In some embodiments, the metal-organic frameworks constitute from about 8 wt % to about 18 wt % of the combined mass of the textile component and the metal-organic frameworks. In some embodiments, the metal-organic frameworks constitute from about 10 wt % to about 15 wt % of the combined mass of the textile component and the metal-organic frameworks.

In some embodiments, the metal-organic frameworks have a mass ranging from about 0.5 mg per $cm^2$ of conductive textile to about 10 mg per $cm^2$ of conductive textile. In some embodiments, the metal-organic frameworks have a mass ranging from about 1 mg per $cm^2$ of conductive textile to about 2.5 mg per $cm^2$ of conductive textile.

The metal organic frameworks of the present disclosure can also include various surface areas. For instance, in some embodiments, the metal-organic frameworks constitute a surface area ranging from about 10 $m^2/g$ to about 1,000 $m^2/g$. In some embodiments, the metal-organic frameworks have a surface area ranging from about 50 $m^2/g$ to about 500 $m^2/g$. In some embodiments, the metal-organic frameworks have a surface area ranging from about 300 $m^2/g$ to about 500 $m^2/g$. In some embodiments, the metal-organic frameworks have a surface area ranging from about 400 $m^2/g$ to about 500 $m^2/g$.

Association of Metal-Organic Frameworks with Textile Components

Metal-organic frameworks may be associated with textile components in various manners. For instance, in some embodiments, metal-organic frameworks are coated on a surface of the textile component. In some embodiments, metal-organic frameworks are conformally coated on the fibers of the textile component. In some embodiments, metal-organic frameworks form an even coating on the fibers of the textile component. In some embodiments, metal-organic frameworks are in the form of tightly packed structures (e.g., nanorods, nanosheets, or irregularly-shaped particles) that form an even coating over each fiber of the textile component.

In some embodiments, the metal-organic frameworks are impregnated into the fibers of the textile component. In some embodiments, the metal-organic frameworks are dispersed into the fibers of the textile component.

In some embodiments, the metal-organic frameworks are integrated with the textile component. In some embodiments, the metal-organic frameworks are in ohmic contact with the textile component.

In some embodiments, a plane of the textile component is perpendicular to a plane of the metal-organic frameworks. In some embodiments, a lattice plane of the textile component is perpendicular to a two-dimensional plane of the metal-organic frameworks. In some embodiments, the textile component and the metal-organic frameworks form a long range "honeycombed" order in a slipped parallel packing motif. In some embodiments, the metal-organic framework may be chemically fused to the textile component through covalent or non-covalent chemical interactions. In some embodiments, the metal-organic framework may be chemically fused to the textile component through covalent chemical interactions.

Conductive Networks

The metal-organic frameworks of the present disclosure can form various types of conductive networks when associated with textile components. For instance, in some embodiments, the metal-organic frameworks are in the form of a conductive pathway on the fibers of the textile component. In some embodiments, the metal-organic frameworks are in the form of a conductive pathway across a length of the textile component. In some embodiments, the metal-organic frameworks are in the form of a conductive pathway through the entire volume of the textile component.

The formed conductive networks may have various conductive surface areas. For instance, in some embodiments, the conductive network includes a conductive surface area of at least 1 cm$^2$. In some embodiments, the conductive network includes a conductive surface area ranging from about 1 cm$^2$ to about 100 cm$^2$. In some embodiments, the conductive network includes a conductive surface area ranging from about 1 cm$^2$ to about 25 cm$^2$.

Conductive Textile Properties

The conductive textiles of the present disclosure can have various advantageous properties. For instance, in some embodiments, the conductive textiles of the present disclosure have optimal conductivities. In some embodiments, the conductive textiles of the present disclosure have conductivities ranging from about 0.0001 S/cm to about 2.0 S/cm. In some embodiments, the conductive textiles of the present disclosure have conductivities ranging from about 0.0001 S/cm to about 0.003 S/cm.

In some embodiments, the conductive textiles of the present disclosure display optimal sheet resistance. For instance, in some embodiments, the conductive textiles of the present disclosure have a sheet resistance ranging from about 0.5 M$\Omega$/cm$^2$ to about 20 M$\Omega$/cm$^2$. In some embodiments, the conductive textiles of the present disclosure have a sheet resistance ranging from about 1 M$\Omega$/cm$^2$ to about 10 M$\Omega$/cm$^2$. In some embodiments, the conductive textiles of the present disclosure have a sheet resistance ranging from about 2 M$\Omega$/cm$^2$ to about 10 M$\Omega$/cm$^2$. In some embodiments, the conductive textiles of the present disclosure have a sheet resistance ranging from about 2 M$\Omega$/cm$^2$ to about 8 M$\Omega$/cm$^2$. In some embodiments, the conductive textiles of the present disclosure have a sheet resistance ranging from about 3 M$\Omega$/cm$^2$ to about 8 M$\Omega$/cm$^2$. In some embodiments, the conductive textiles of the present disclosure can have a sheet resistance ranging from about 1 $\Omega$/cm$^2$ to about 1 k$\Omega$/cm$^2$.

In some embodiments, the conductive textiles of the present disclosure have dual porosities that can be advantageous in the simultaneous filtration, pre-concentration, and capture of analytes. For instance, in some embodiments, the textile component includes a plurality of mesopores while the metal-organic frameworks include a plurality of micropores.

The conductive textiles of the present disclosure can also have various surface areas. For instance, in some embodiments, the conductive textiles of the present disclosure have a surface area ranging from about 1 m$^2$/g to about 200 m$^2$/g. In some embodiments, the conductive textiles of the present disclosure have a surface area ranging from about 1 m$^2$/g to about 50 m$^2$/g. In some embodiments, the conductive textiles of the present disclosure have a surface area ranging from about 1 m$^2$/g to about 10 m$^2$/g. In some embodiments, the conductive textiles of the present disclosure have a surface area ranging from about 3 m$^2$/g to about 10 m$^2$/g.

The conductive textiles of the present disclosure can also have various mechanical properties. For instance, in some embodiments, the conductive textiles of the present disclosure may be capable of bending, twisting, and wrapping without a loss of conductivity. In some embodiments, the conductive textiles of the present disclosure can be wearable and portable.

Additional Conductive Textile Components

The conductive textiles of the present disclosure may also be associated with additional components. For instance, in some embodiments, the conductive textiles of the present disclosure also include electrodes. In some embodiments, the electrodes are sewn onto the conductive textile.

In some embodiments, the conductive textiles of the present disclosure also include a porous coating. In some embodiments, the porous coating is associated with the textile component. In some embodiments, the porous coating includes a polymeric coating.

The conductive textiles of the present disclosure can also have various architectures. For instance, in some embodiments, the conductive textiles of the present disclosure are in the form of a single layer. In some embodiments, the conductive textiles of the present disclosure are in the form of a plurality of layers. In some embodiments, the multi-layer conductive textiles may be stacked in order to form various stacked architectures.

In some embodiments, each conductive textile layer within a multi-layered structure may be the same. In other embodiments, the conductive textile layers may be different. For instance, in some embodiments, a textile component associated with metal-organic framework 1 may be stacked with another textile component that is associated with metal-organic framework 2.

The multi-layer conductive textiles of the present disclosure can have numerous applications. For instance, in some embodiments, the multi-layer conductive textiles of the present disclosure may be utilized as a garment for sensing analytes that flow from both the inside and from the outside of the garment.

Methods of Sensing Analytes in a Sample

The conductive textiles of the present disclosure may be utilized to sense various analytes in various samples through various methods. Such methods generally include exposing the sample to the conductive textile. Thereafter, the presence or absence of the analyte from the sample is detected by detecting a change in a property of the conductive textile and correlating the change in the property to the presence or absence of the analyte.

Analytes

The methods of the present disclosure may be utilized to detect various analytes in a sample. For instance, in some embodiments, the analyte includes, without limitation, gases, ketones, alcohols, aromatic compounds, water, neurotransmitters, hormones, proteins, sugars, metal ions, and combinations thereof. In some embodiments, the analytes include ketones, such as acetone or butanone. In some embodiments, the analytes include alcohols, such as methanol or ethanol. In some embodiments, the analytes include aromatic compounds, such as benzene or xylene.

In some embodiments, the analytes to be detected include one or more gases. In some embodiments, the one or more gases include, without limitation, NO, CO, $H_2S$, $NH_3$, $H_2O$, and combinations thereof. In some embodiments, the analyte to be detected includes NO. In some embodiments, the analyte to be detected includes $H_2S$. In some embodiments, the analytes to be detected include NO and $H_2S$.

In some embodiments, the analytes to be detected include water-soluble molecules, such as neurotransmitters and hormones. In some embodiments, the analytes to be detected include metal ions.

Samples

The methods of the present disclosure may be utilized to detect analytes from various samples. For instance, in some embodiments, the sample is in gaseous form. In some embodiments, the sample is in liquid form. In some embodiments, the sample is derived from an environment, such as a gaseous environment. In some embodiments, the sample is a heterogeneous mixture, such a slurry or a soil sample.

Exposure of Sample to Conductive Textiles

Various methods may be utilized to expose samples to conductive textiles. For instance, in some embodiments, the exposure occurs by flowing the sample through the conductive textile. In some embodiments, the exposure occurs by incubating the sample with the conductive textile.

In some embodiments, the exposure of a sample to a conductive textile occurs in an active manner, where an active step is taken to expose samples to the conductive textile (e.g., actively flowing the sample through the conductive textile). In some embodiments, the exposure occurs in a passive manner, such as through the passive incubation of the conductive textile with the sample. In some embodiments, the exposure occurs in a passive manner, such as through the capillary action on a patterned textile.

In some embodiments, the exposure of a sample to a conductive textile results in the association of any analyte in the sample with the conductive textile. Analytes may become associated with conductive textiles in various manners. For instance, in some embodiments, the analytes become reversibly associated with the conductive textile. In some embodiments, the analytes become associated with the metal-organic frameworks of the conductive textile.

The association of analytes with conductive textiles can have various results. For instance, in some embodiments, the association of analytes with conductive textiles results in the filtration, pre-concentration, and capture of the analyte. In some embodiments, the association, filtration, pre-concentration and capture of the analyte occur simultaneously.

Detection of Analytes in a Sample

In some embodiments, the presence or absence of analytes in a sample can detected by detecting a change in a property of the conductive textile and correlating the change to the presence or absence of the analyte. Various changes in conductive textile properties can be correlated to the presence or absence of analytes.

For instance, in some embodiments, the change in the property of the conductive textile includes a change in normalized conductance over time ($\Delta G/Go$). In some embodiments, the change in the property of the conductive textile includes an increase in normalized conductance over time. In some embodiments, the change in the property of the conductive textile includes a decrease in normalized conductance over time.

In some embodiments, the change in the property of the conductive textile includes a change in resistance over time. In some embodiments, the change in the property of the conductive textile includes an increase in resistance over time. In some embodiments, the change in the property of the conductive textile includes a decrease in resistance over time. In some embodiments, the change in the property of the conductive textile includes a change in conductance, current, or potential.

Various methods may be utilized to correlate the change in the property of the conductive textile to the presence or absence of analytes. For instance, in some embodiments, the correlation occurs manually. In some embodiments, the correlation occurs automatically. In some embodiments, the correlation includes a comparison of the change in the property of the conductive textile when exposed to a sample to changes in the properties of the conductive textile when exposed to known analytes. The comparison can then be used to determine whether or not an analyte is present or absent from a sample.

The methods of the present disclosure may be utilized to detect the presence or absence of analytes in a sample at various analyte concentrations. For instance, in some embodiments, the analytes are detected at concentrations of less than about 100 ppm. In some embodiments, the analytes are detected at concentrations of less than about 80 ppm. In some embodiments, the analytes are detected at concentrations of less than about 1 ppm.

In some embodiments, the analytes are detected at concentrations ranging from about 0.1 ppm to about 100 ppm. In some embodiments, the analytes are detected at concentrations ranging from about 0.1 ppm to about 80 ppm. In some embodiments, the analytes are detected at concentrations ranging from about 0.1 ppm to about 1 ppm. In some embodiments, the analytes are detected at concentrations ranging from about 0.1 ppm to about 2 ppm. In some embodiments the analytes are detected at concentrations ranging from about 0.1 ppm to about 0.6 ppm. In some embodiments the analytes are detected at concentrations ranging from about 0.16 ppm to about 0.23 ppm.

In some embodiments, the methods of the present disclosure may be utilized to detect a single analyte. In some embodiments, the methods of the present disclosure may be utilized to detect a plurality of different analytes (e.g., NO and $H_2S$ gases). In some embodiments, the plurality of different analytes are differentiated through principle component analysis (PCA).

In some embodiments, analyte detection occurs in a qualitative manner. In some embodiments, analyte detection occurs in a quantitative manner. For instance, in some embodiments, the concentration of analytes in a sample can be determined.

Analyte detection may occur under various conditions. For instance, in some embodiments, the analytes are detected under a constant voltage. In some embodiments, the analytes are detected under an alternating voltage or a voltage sweep. In some embodiments, the analytes are detected under a pulsed voltage. In some embodiments, the analytes are detected under no applied voltage. In some embodiments, analyte detection occurs in real-time.

In some embodiments, analyte detection occurs in an aqueous environment. In some embodiments, analyte detection occurs in the presence of water. In some embodiments, analyte detection occurs in a humid environment. In some embodiments, the humid environment has a relative humidity of 10% or higher. In some embodiments, the humid environment has a relative humidity of 15% or higher. In some embodiments, the humid environment has a relative humidity of 18% or higher. In some embodiments, the humid environment has a relative humidity of 20% or higher.

Release of Analytes from Conductive Textile

In some embodiments, the methods of the present disclosure also include a step of releasing the analyte from the conductive textile. Various methods may be utilized to release analytes from conductive textiles.

For instance, in some embodiments, the releasing occurs by washing the conductive textile. In some embodiments, the washing includes exposing the conductive textile to water.

In some embodiments, the releasing occurs by heating the conductive textile. In some embodiments, the releasing occurs without any heating steps.

In additional embodiments, the methods of the present disclosure also include a step of reusing the conductive textile after the release of the analytes. For instance, in some embodiments, the conductive textiles may reused to sense additional analytes.

Methods of Making Conductive Textiles

Additional embodiments of the present disclosure pertain to methods of making the conductive textiles of the present disclosure. Such methods generally include associating metal-organic frameworks with a textile component.

Various methods may be utilized to associate metal-organic frameworks with a textile component. For instance, in some embodiments, the association includes associating one or more metals and one or more organic ligands with the textile component such that the metal-organic frameworks self-assemble during the association. In some embodiments, the association includes associating pre-formed metal-organic frameworks with the textile component.

Association of metal-organic frameworks with textile components can occur by various processes. For instance, in some embodiments, such processes include, without limitation, vapor deposition, solution-phase self-assembly, sonication, stirring, heating, mixing, solvothermal growth, liquid-phase epitaxy, spray-coating, film casting, post-synthetic attachment, electrochemical deposition, atomic layer deposition, direct precipitation, and combinations thereof. In some embodiments, the association occurs by vapor deposition. In some embodiments, the association occurs by solution-phase self-assembly.

In some embodiments, the association occurs in a patterned manner. For instance, in some embodiments, the association occurs by depositing a protective coating on a surface of the textile component, associating the metal-organic frameworks with the textile component, and removing the protective coating to form a pattern of metal-organic frameworks on the textile component.

In some embodiments, the conductive textiles of the present disclosure can be fabricated in a scalable manner. In some embodiments, the properties of the formed conductive textiles can be controlled by selecting desired metal-organic frameworks, organic ligands and metals during the fabrication process. In some embodiments, the tunable properties can include, without limitation, conductivity, chemiresistive properties, and combinations thereof.

In more specific embodiments, the self-assembly of metal-organic framework precursors (e.g., organic ligands and metals) on textile components (e.g., cotton) produces a conformal, porous coating of functional nanomaterials. Typically, vapor deposition methods are desirable to coat textile components with metal-organic frameworks at the fiber level.

Applications and Advantages

The present disclosure can have various advantages. For instance, in some embodiments, the conductive textiles of the present disclosure have at least the following valuable features: i) they exhibit enhanced porosity by combining mesoporosity of the textile component and microporosity of the metal-organic frameworks; ii) they are capable of simultaneously detecting, capturing, pre-concentrating, and filtering gases; iii) they are flexible, washable (e.g., in water and acetone), and stable to heat; iv) they retain their functional integrity, conductivity, and gas sensing capability in the presence of humidity (e.g., at least 5000 ppm $H_2O$); v) they show ligand specific differences in metal-organic framework design, which can be useful attributes for controlling the unique chemiresistive response of these materials towards analytes; and vi) they are capable of detecting analytes at very low concentrations (e.g., 0.16 ppm for NO and 0.23 ppm for $H_2S$).

In some embodiments, the conductive textiles of the present disclosure exhibit dynamic ranges of sensor response that are orders of magnitude higher than comparable devices (e.g., MOF-based chemiresistive sensors and textile chemiresistors). In addition, because the conductive textiles of the present disclosure can be electrically responsive and electrochemically active, they can have unique functions in chemical capture and release through electrical modulation.

As such, the conductive textiles of the present disclosure can be utilized in various manners and for various purposes. For instance, in some embodiments, the conductive textiles of the present disclosure are utilized as a component of a functional device. In some embodiments, the functional device includes, without limitation, chemiresistive sensors, chemiresistors, electronically-triggered resistive heaters, filtration devices, and combinations thereof. In some embodiments, the conductive textiles of the present disclosure can be utilized as chemiresistive sensors.

In some embodiments, the conductive textiles of the present disclosure can have broad applications in sensing that range from real-time detection of gases, liquid-soluble molecules, and biologics in wearable systems, to electronically accessible adsorbent layers in protective equipment such as gas masks. In some embodiments, the conductive textiles of the present disclosure can advance functional materials design, MOF-based electronics, and methods for integrating electrically conductive stimuli-responsive materials into solid-state devices. In some embodiments, the conductive textiles of the present disclosure can be utilized in the design of wearable electronics with enhanced capabilities in chemical detection, personal protection, and gas sequestration.

In some embodiments, the dual porosity of the conductive textiles of the present disclosure can allow for the simultaneous detection and sequestrations of toxic materials. In some embodiments, the conductive textiles of the present disclosure can passively interact with a local environment of the user or actively detect and respond to desired stimuli in a flexible, porous platform.

In some embodiments, the structural and functional tunability afforded by the diversity of available ligands and nodes can impart rationally designed functionality into the assembled metal-organic framework at the monomer stage. Integration of conductive MOFs into textile components to create conductive textiles that synergistically integrate the desirable features of conductive MOFs—electronic response to stimuli and high surface area—with the porosity and flexibility of the textile component can greatly enhance the functional utility of conductive textiles of the present disclosure.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Self-Organized Frameworks on Textiles (SOFT): Conductive Fabrics for Simultaneous Sensing, Capture, and Filtration of Gases This Example describes a facile and rapid approach for fabricating multifunctional e-textiles by integrating conductive two-dimensional (2D) metal-organic frameworks (MOFs) into fabrics through direct solution-phase self-assembly from simple molecular building blocks. These e-textiles display reliable conductivity, enhanced porosity, flexibility, and stability to washing. The functional utility of these integrated systems is demonstrated in the context of chemiresistive gas sensing, uptake, and filtration. The SOFT-devices detect and differentiate important gaseous analytes (NO, $H_2S$, and $H_2O$) at ppm levels, and maintain their chemiresistive function in the presence of humidity (5000 ppm, 18% RH). With sub-ppm theoretical limits of detection (LOD for NO=0.16 ppm, and for $H_2S$=0.23 ppm), these constitute the best textile-supported $H_2S$ and NO detectors reported, and the best MOF-based chemiresistive sensors for these analytes. In addition to sensing, these devices are capable of capturing and filtering analytes.

The MOF-based e-textiles reported herein display at least seven unique characteristics for functional materials design: i) They are the first example of using conductive MOFs as functional components in e-textiles. ii) They exhibit enhanced porosity by combining mesoporosity of the textile and microporosity of the conductive MOF; iii) They represent the first demonstration of simultaneous detection, capture, pre-concentration, and filtration of gases in MOF-based chemiresistive device architectures; iv) They are flexible, washable (in water and acetone), and stable to heat; v) They retain their functional integrity, conductivity, and gas sensing capability in the presence of humidity (at least 5000 ppm $H_2O$); vi) These systems show that ligand specific differences in MOF design can be useful attributes for controlling the unique chemiresistive response of these materials towards analytes; vii) In terms of magnitude of chemiresistive response, SOFT-devices constitute the best SFS NO and $H_2S$ detectors reported and the best MOF-based chemiresistive NO and $H_2S$ sensors with theoretical limits of detection (LOD) of 0.16 ppm for NO and 0.23 ppm for $H_2S$.

Figure 2:
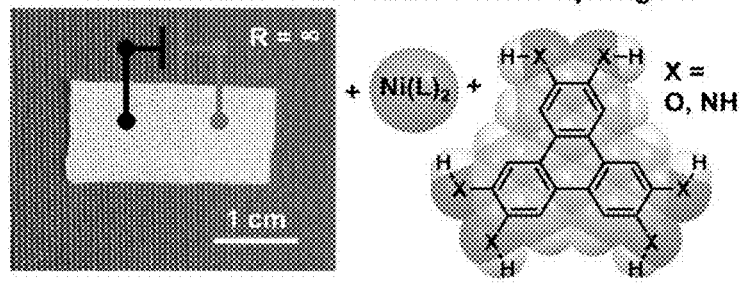
FIG. 2 illustrates the fabrication of metal-organic framework (MOF) devices and sheet resistance of self-organized frameworks on textiles (SOFT)-sensor devices.
Figure 2:
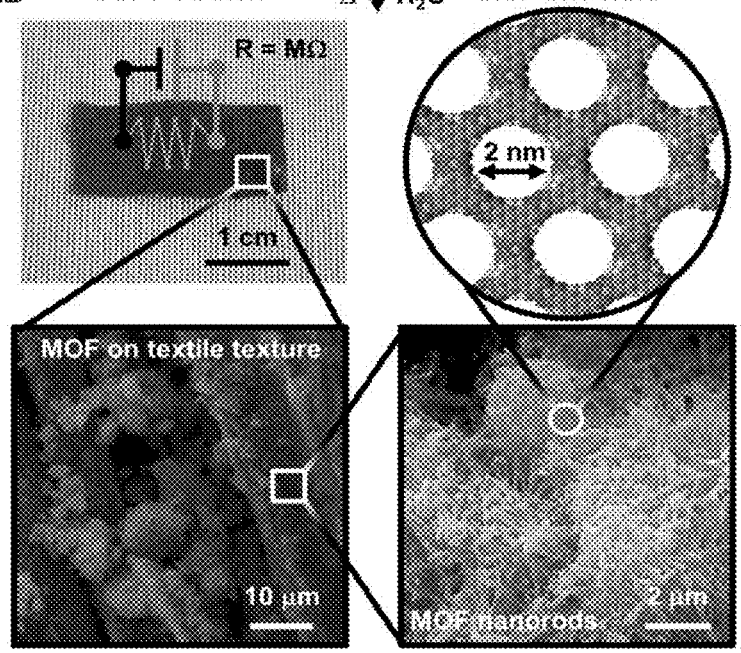

As illustrated in FIGS. 2A-B, this Example describes a one-step fabrication of flexible, textile-supported devices based on conductive MOFs. The direct self-assembly of 2,3,5,6,10,11-hexahydroxy (HHTP) or amino-substituted (HITP) triphenylene-based organic ligands with metallic nickel (II) nodes from solution onto natural (cotton) and synthetic (polyester) fabrics produces textiles that are conformally-coated with conductive MOF ($Ni_3HHTP_2$ or $Ni_3HITP_2$) crystallites at the fiber-level (FIG. 2C). To the best of Applicants' knowledge, this Example constitutes the first use of direct self-assembly to deposit conductive MOFs on textiles.

In this Example, Applicants chose two MOFs with high bulk electrical conductivities (0.01-2.0 S/cm): metal catecholate and imino cross-linked frameworks $Ni_3HHTP_2$ and $Ni_3HITP_2$, respectively. The reactive starting materials readily assemble into conductive d-π conjugated scaffolds in solvothermal reaction conditions (FIG. 2B). This Example demonstrates that the method of direct assembly can be generalized to achieve the integration of conductive MOFs into textiles with unique SOFT-device architecture.

Example 1.1. Fabrication of Devices

Applicants chose textiles for the immobilization of functional MOF-based materials because fabrics are chemically modifiable (as shown by dyeing processes), physically tunable (roughness and thickness), chemically diverse (natural and synthetic), often low-cost and renewable, and compatible with straightforward integration directly into the existing infrastructure of cloth garments, coverings, and commercial goods. To prepare SOFT-devices, commercial textiles were cut into swatches (1×2 cm). Applicants focused on natural woven cotton fabric (0.243 mm thick) in this Example due to the precedent for cotton serving as an effective platform for e-textiles.

To display the generality of the method, Applicants also tested synthetic non-woven polyester batting (0.643 mm thick, compressed), and found these devices to perform indistinguishably from the cotton-based SOFT-devices (see Examples 1.25 and 1.31).

To achieve the assembly of MOFs on fabrics, Applicants added solid molecular precursors (organic ligand and metallic node) directly to a vial containing the fabric swatch (one swatch per vial), and added water such that all reagents and textiles were fully dampened (0.033M with respect to triphenylene ligand). For $Ni_3HITP_2$, ammonium hydroxide (6 eq with respect to HITP) was also added to the reaction vessel. The mixtures were subjected to sonication (5 minutes) and stirred overnight at 80° C. Applicants allowed the resulting SOFT swatches to cool in the reaction mixture, then isolated, washed thoroughly with water (1×2 mL) and acetone (1×2 mL), and drip dried the devices in air (18 h).

SOFT-devices included an average of 7-8% MOF (by weight), corresponding to 4-6 mg of MOF per $cm^3$ of textile (see Example 1.17). Textile-supported MOF constituted 16-30% of the total mass of MOF prepared, taking into account both the SOFT-device and the precipitated MOF powder isolated from the reaction solution. The characterization of bulk MOF powder samples matched reported analysis (See Examples 1.17-1.23).

Example 1.2. Characterization of Devices

To characterize the successful integration of MOFs into textiles, bulk MOF (isolated from the SOFT-device reaction solution) was compared to MOF incorporated into devices using powder x-ray diffraction (PXRD: Example 1.21), scanning electron microscopy (SEM: Example 1.22), and energy-dispersive x-ray spectroscopy (EDS: Example 1.23). Key PXRD peaks corresponding to Bravais planes oriented perpendicular to the 2D plane of the nanomaterial were present for both bulk and SOFT-samples, suggesting long range "honeycombed" order in a slipped parallel packing motif, as expected. The PXRD traces for the MOF-coated fabrics, however, were convoluted by the fabric substrate—which alone presents a series of sharp peaks and broad amorphous regions—and while suggestive of MOF presence, were not conclusive alone. Identity and morphology of the MOFs was confirmed by EDS and SEM (FIG. 2C and Examples 1.22 and 1.23).

Electron micrographs of the MOF-coated fabrics indicated tightly packed MOF-nanorods forming a continuous coating over each fiber. Cross sections of the SOFT-devices indicated conformal coating of the textile by the MOF. If the swatches remained fully submerged in the reaction solution throughout assembly, the conformity of the MOF assembly was uniform throughout the swatch. Swatches that stuck to the sides of the vial, or remained partially submerged were considered non-functional devices, even if the submerged portion displayed conductivity. The elemental composition of the MOF-nanorods matched bulk MOF (See Example 1.23).

Thermal gravimetric analysis (TGA) of SOFT-devices showed both devices to be stable up to 350° C. under nitrogen (See Example 1.20). The crystallization of MOF coating did not compromise the thermal stability of the cotton substrate, which is similarly stable up to 350° C. under nitrogen (See Example 1.20). A mass loss around 100° C. corresponding to the loss of trapped or bound water is commonly observed in porous materials. A loss of only 1% mass was observed for both devices in this range, suggesting that devices were fully dry after the process of washing and drip drying. These results suggest that conductivity results from the MOF itself, not from trapped water.

Example 1.3. Enhanced Porosity

Applicants used Brunauer-Emmett-Teller (BET) measurements to gain insight into the porosity of the SOFT-devices as compared to their MOF and cotton constituents. For $Ni_3HHTP_2$, the BET surface area for the bulk MOF was found to equal 421 $m^2/g$ in argon (77 K), in agreement with reported values (425 $m^2/g$). Integration of MOFs into SOFT-devices increased the BET surface area from 0.3 $m^2/g$ for bare cotton to 3.6 $m^2/g$ for SOFT-devices, an order of magnitude increase in porosity (See Example 1.24). If all MOF pore openings remained unblocked, and full internal surface area of the MOFs on textiles was available, the BET surface area would be equal to approximately 50 $m^2/g$. The nature of the templation likely caused a certain percentage of MOF surface to be unavailable (the surface that templates on the fiber), leading to a deviation from the theoretical maximum surface area. $Ni_3HITP_2$ exhibited similar trends, with a surface area of 340 $m^2/g$ for pure MOF and a surface area equal to 6.8 $m^2/g$ for the SOFT-device (argon: 77 K).

Example 1.4. Functional Performance and Yield

Conductive MOF-coated textiles were classified as functional in this study if they exhibited measurable resistance when probed with a multimeter over a 1 cm distance once fully dried. The crystallization of conformal MOF coatings was found to be a desired feature for the electrical and chemiresistive performance. Control experiments that involved soaking fabric swatches in solutions containing individual starting materials, or repeatedly dip-coating swatches (see Example 1.28) in suspensions of pre-synthesized MOFs in varied solvents did not generate a conductive pathway, suggesting that direct crystallization is desired for SOFT-fabrication.

As a further control, Applicants soaked swatches of fabric substrate in solutions containing both starting materials—as Applicants would to produce SOFT-devices—but prevented the large-scale crystallization of MOF by limiting the reaction time and keeping the samples at room temperature (5 minutes soaking with 1 minute sonication: see Example 1.21 for XRD, Example 1.22 for SEM, and Example 1.23 for EDX). This method did not produce a conductive pathway in fabric swatches, implying that crystallization of MOF is important for SOFT fabrication.

Direct solution-phase crystallization of MOFs was capable of generating a large surface area of conductivity, up to 25 $cm^2$ of conductive surface (measured diagonally across a 5×5 cm swatch, largest area tested) for $Ni_3HHTP_2$ (see Example 1.32). This fabrication method yielded functional swatches with moderate sheet resistance ($Ni_3HHTP_2$: 2.8±0.5 $M\Omega/cm^2$, $Ni_3HITP_2$: 5.6±2 $M\Omega/cm^2$, FIG. 2C) and high yields of functional devices. For each device, Applicants performed a minimum of n=10 fabrication trials, yielding 94% functional devices for $Ni_3HHTP_2$ on cotton (n=30), 87% for $Ni_3HHTP_2$ on batting (n=13), and 96% for $Ni_3HITP_2$ on cotton (n=23). The small number of non-functional devices either failed to display conductivity, or did not have a uniform distribution of MOF across the swatch.

Two-point conductivity for cotton SOFT-sensors was calculated to be $1.6 \times 10^{-4}$ S/cm for $Ni_3HHTP_2$ and $2.6 \times 10^{-3}$ S/cm for $Ni_3HITP_2$. The devices were semiconductive within their usable temperature range (room temperature to ~80° C., see Example 1.32), as evidenced by their linear increase in conductivity with increasing temperature. Gold-coated pins exhibited Ohmic contacts with the SOFT-sensors in the range from –2.0 V to 2.0 V at 0.1 V intervals (see Example 1.32).

Example 1.5. Mechanical Stability

Figure 3:
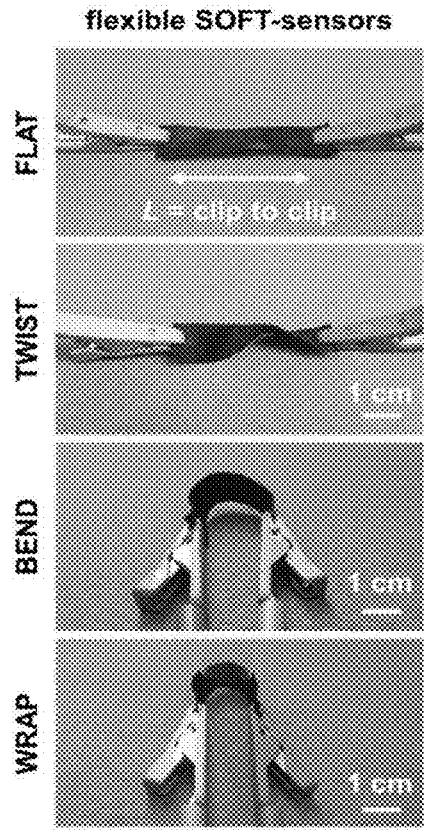
FIG. 3 shows selected mechanical and electronic properties of SOFT-sensors.
Figure 3:
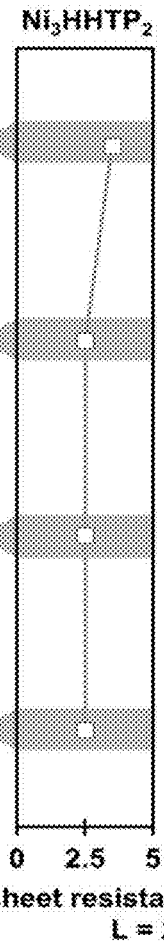
Figure 3:
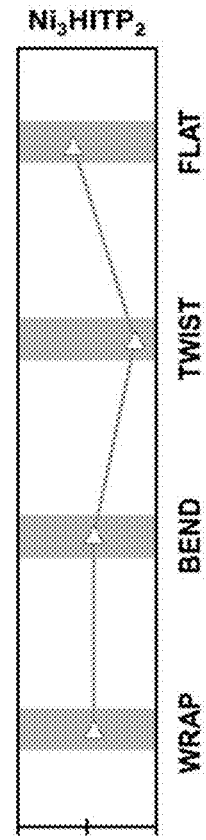

The SOFT-devices retained the physical properties of the textile, and were capable of being bent, twisted, and wrapped around curved surfaces without a significant perturbation or loss of conductivity (FIG. 3A). Gentle handling (i.e., installing into custom enclosures, bending) did not cause measurable mass loss of the MOF. Repeated deformation did not impact performance: devices bent or folded up to and beyond 10 cycles (typical handling for multiple sensing experiments) retained consistent conductivity.

The direct bottom-up integration process allows for the coverage of large areas of fabric in different aspect ratios. Squares of material up to (25 $cm^2$) displayed conductivity throughout the SOFT-device, including along the diagonal (~5.5 cm). The swatches were cut along the grain, and consequently could be stretched along the diagonal bias. For the large SOFT swatch, stretching deformation did not impact the resistance greatly: a swatch stretched from 4 cm to 5 cm (25% increase) showed a resistance change of 0.06-0.05 $M\Omega/cm^2$, respectively (see Example 1.32). The SOFT-devices were stable to washing with water or with organic solvent (acetone), and resistant to dis-assembly through mechanical handling.

When cut and punctured (e.g., sewing), SOFT-devices lost up to 20% of their mass via fraying of the fabric and some MOF shedding, but still retained their conductivity, with no significant change in sheet resistance or chemiresistive performance. Most mass lost was attributable to fraying of the fabric, as the mass of the MOF included only 7-8% of the full mass of the device. Fraying occurred primarily during cutting: when the devices were prepared as large swatches (4.5-25 $cm^2$), and then cut into small sections for testing of device properties (i.e., sensing capabilities).

Example 1.6. Directed Patterning of Conductive Areas within Devices

This strategy for the incorporation of conductive nanomaterials into e-textiles through self-assembly makes it possible to fabricate unique device architectures that would be otherwise difficult to achieve. The sensor fabrication was tolerant of an assortment of pre-patterned architectures: MOF assembly proceeded on top of and between existing electrodes, including sewn-in conductive threads and painted silver electrodes. Generating patterns of the MOFs on fabrics was accomplished by masking specific areas of the fabric with a hydrophobic barrier (e.g., petroleum jelly). Loading a syringe with petroleum jelly enabled manual patterning of this hydrophobic barrier directly onto the surface of the fabric with reasonable control (±0.5 cm).

Gentle heating (40-50° C.) melted the jelly into the bulk of the textile, and masked the patterned area from MOF assembly in aqueous solution. Isolation of the swatch from the reaction mixture and washing with water, acetone, and with petroleum ether removed any residual petroleum jelly yielding a clean, patterned SOFT-device (Example 1.29). This approach enabled the preparation of a range of device architectures, including arrays of SOFT-devices mounted on a single swatch, equipped with pre-patterned (or sewn) electrodes.

Example 1.7. Assessment of SOFT-Devices as Chemiresistive Sensors

Applicants demonstrate the multifunctional utility of SOFT devices in the context of chemiresistive sensing of toxic gases, as well as capture, filtration, and pre-concentration of gaseous analytes. The sensing performance of the SOFT devices was tested in the configuration of a chemiresistor against toxic gaseous analytes with low permissible exposure limits (PELs): $H_2S$ (PEL=10 ppm) and NO (PEL=25 ppm). As target analytes, $H_2S$ and NO are also relevant for breath analysis, as their relative concentrations in exhalate have implications in endogenous processes related to disease. Furthermore, $H_2S$ and NO are common toxic emissions from human industry, and considered dangerous pollutants. NO, produced primarily in vehicle exhaust, is a reactive compound that contributes to the formation of ozone and smog. $H_2S$ is a corrosive poison released from refineries and animal farms that is acutely dangerous to aquatic life. As such, development of materials and devices capable of maximizing the real-time detection, uptake, and/or controlled release of NO and $H_2S$ is broadly important in human health and safety, environmental remediation, and health monitoring. As controls, Applicants tested the response of the SOFT devices to water and a range of organic vapors (Example 1.31).

Example 1.8. General Procedure for Chemiresistive Measurements

Figure 4:
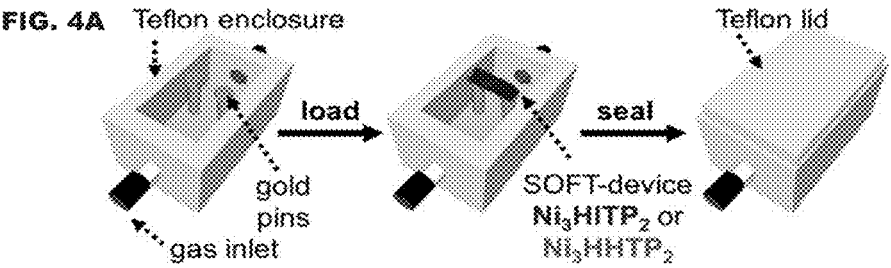
FIG. 4 shows chemiresistive device performance for SOFT-sensors.
Figure 4:
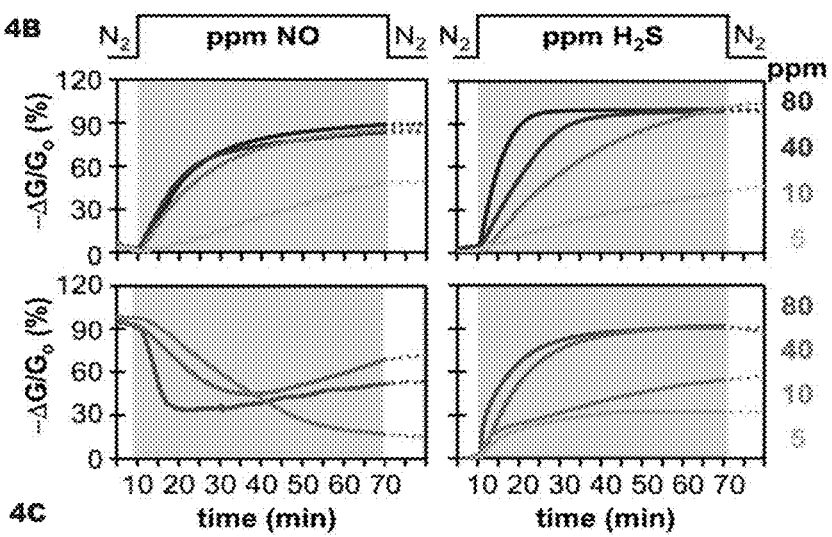
Figure 4:
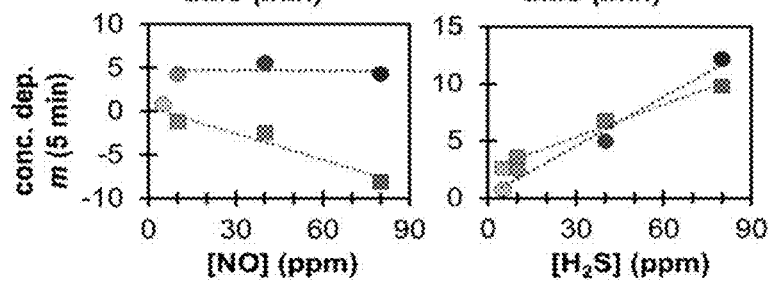

SOFT swatches were placed into custom Teflon enclosure equipped with spring-loaded gold pins (serving as electrodes and immobilizing textile swatches) and gas inlet and outlet ports (FIG. 4A) and sealed tightly for leak-free gas flow. Constant voltage was applied across the electrodes using a portable potentiostat (1.0 V). The current was monitored across the exposure (through saturation) and recovery (10 minute) cycles of analyte dosing. Gaseous analytes were delivered from custom-ordered tanks containing each analyte at 1% concentration balanced with $N_2$, were further diluted in dry nitrogen ($N_2$), and regulated using a system of dual mass flow controllers.

Example 1.9. Characterization of the Sensitivity and Dynamic Range of SOFT-Sensors in $N_2$ SOFT devices exhibited dosimetric responses to NO and $H_2S$—detailed in FIGS. 4B and 4C, and Example 1.31—that were contingent upon MOF identity. Percent response is shown in terms of normalized conductance ($-\Delta G/G_o$, see Example 1.31 for equation), and compared for SOFT-sensors (1.5×0.5 cm). While MOFs employing the HHTP organic ligand have been previously used to sense these analytes, the study of the chemiresistive responses of HITP-based MOFs to these gases has not been previously examined. Representative saturation traces for NO and $H_2S$ are shown in FIG. 4B. For NO, SOFT-device response decreased with analyte exposure for $Ni_3HHTP_2$ (saturation=−49±10%, n=3), and increased for $Ni_3HITP_2$ (saturation=81±6%, n=3), demonstrating the importance of the identity of the heteroatom in the framework crosslinker on sensing ability.

When exposed to $H_2S$, an increase in resistance was observed for both $Ni_3HHTP_2$ (saturation=98±9%, n=3) and for $Ni_3HITP_2$ (saturation=97±2%, n=3). The density of MOF crystallites in the SOFT-sensors, coupled to the intrinsic porosity of the fabric substrate, likely contributed to enhancing the response sensitivity toward the analyte as compared to previous reports.

These dosimetric responses were highly reproducible, as evidenced by repeated saturation studies (see Example 1.31). For both $Ni_3HHTP_2$ and $Ni_3HITP_2$, exposure to $H_2S$ demonstrated >10% variance between batches (80 ppm, n=3, see Example 1.31).

The SOFT-sensors were capable of differentiating certain analyte concentrations semi-quantitatively in the first 5 minutes of exposure (FIG. 4C). Plotting the slope of the device trace over the first 5 minutes of exposure versus the concentration of analyte (5-80 ppm range) provided a linear response for $Ni_3HHTP_2$ towards decreasing concentrations of NO, and for both devices towards $H_2S$ (summarized in FIG. 4C). For $Ni_3HITP_2$ SOFT-devices exposed to NO, concentrations as low as 10 ppm saturated SOFT-devices at the same rate as higher concentrations.

Example 1.10. Detection Limits in $N_2$

The responses of $Ni_3HITP_2$ SOFT-devices exposed to NO suggested a low theoretical limit of detection (LOD). Applicants determined the theoretical LODs for each analyte/SOFT-device pair (for full details on calculation, see Example 1.31) by exploiting the maximum percent response (within 1 hour of exposure) versus concentration of analyte. The theoretical LOD of $Ni_3HITP_2$ and $Ni_3HHTP_2$ towards NO (0.1-80 ppm) were 0.16 ppm and 1.4 ppm, and towards $H_2S$ (1-80 ppm) were 0.52 and 0.23 ppm, respectively. For NO, this constitutes one of the best MOF-based sensors for NO. Furthermore, this system is capable of detecting and differentiating NO from $H_2S$ with optimal LODs.

Figure 5:
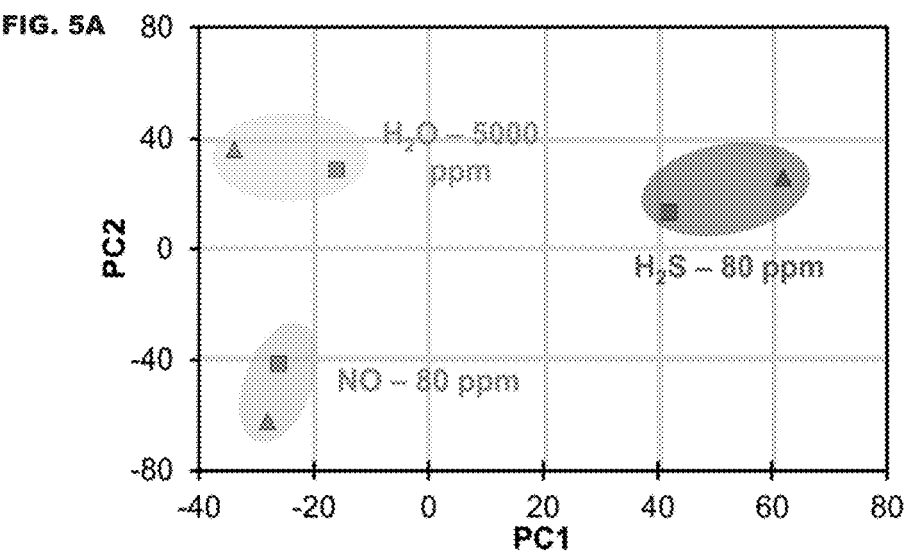
FIG. 5 shows the performance of SOFT-devices in competition with water.
Figure 5:
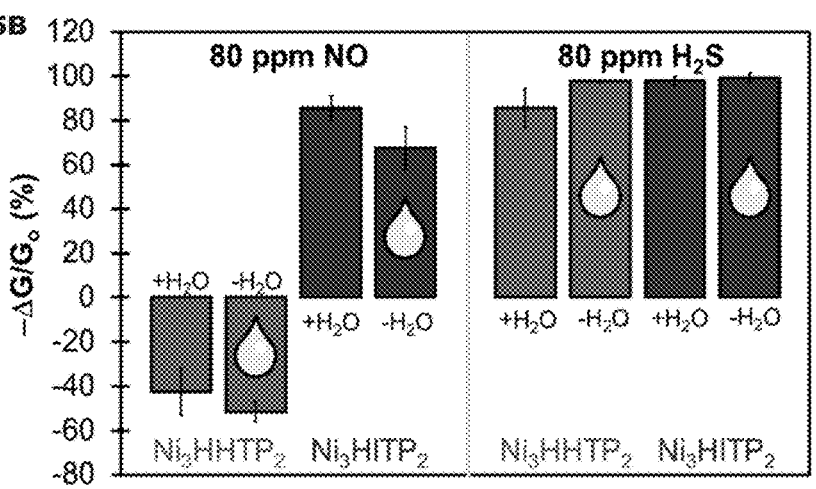

Example 1.11. Chemiresistive Responses of SOFT-Sensors in the Presence of Water The capacity to differentiate the signal corresponding to $H_2O$ from relevant analyte signal is desired for practical applicability. Dosing devices with concentrations of $H_2O$ vapor much higher than the concentrations of analytes (at least 5000 ppm, ~18% relative humidity) caused a decrease in response for $Ni_3HITP_2$ (−8±2%) and an increase for $Ni_3HHTP_2$ (26±1%). Principle component analysis (PCA) enabled the straightforward differentiation of sensor response towards $H_2O$ from sensor response towards NO and $H_2S$ (both at 80 ppm diluted in dry $N_2$) for arrays featuring $Ni_3HHTP_2$ and $Ni_3HITP_2$ SOFT-sensors at saturation (FIG. 5A).

Applicants also tested the ability for the SOFT-devices to detect and differentiate NO and $H_2S$ in a humid environment (18% relative humidity, 5000 ppm). Mixing a humid vapor stream delivered by gas generator with the diluted gaseous stream delivered by mass flow controller upstream of the sensing apparatus produced a humidified analyte stream with controlled concentrations of gas (80 ppm) and water vapor (5000 ppm). Allowing the devices to equilibrate in the presence of $H_2O$, then dosing with analyte produced signal indistinguishable (within error) from dosing in dry $N_2$ (FIG. 5B, Example 1.31).

Many chemiresistors are sensitive or unstable to the presence of water. However, in one example, a related MOF-based chemiresistor isoreticular to those used in Applicants' SOFT-sensors ($Cu_3HITP_2$) was shown to detect $NH_3$ in humidity levels up to 60% RH. This work is the first example of using $Ni_3HITP_2$ and $Ni_3HHTP_2$ to detect NO and $H_2S$ in the presence of humidity, and Applicants' results appear consistent with the promising precedent for related systems. Due to limitations of the gas delivery apparatus (see Example 1.31 for details), sensing of analytes in environments with higher humidity was not examined.

Example 1.12. Influence of Applied Voltage on Device Performance

The chemiresistive performance of devices was not affected by applied voltage. SOFT-devices performed indistinguishably at 1.0 V versus 0.1 V applied voltage (see Example 1.32). Since the measurements of current resulted in reliably and conveniently measurable numbers (~0.5-1.0 µA for $Ni_3HHTP_2$ and 0.1-1.0 mA for $Ni_3HITP_2$) when 1.0 V was applied, chemiresistive sensing experiments were performed at an applied voltage of 1.0 V. Devices maintained their Ohmic character in the range of −2.0 V to 2.0 V while saturated with gaseous analytes (see Example 1.32).

Example 1.13. Device Recovery and Long-Term Stability

Despite exhibiting dosimetric responses toward NO and $H_2S$, the SOFT-devices were fully recoverable post-saturation by washing. A simple wash step with water (suspending devices in deionized $H_2O$ for 5 minutes), followed by complete drying in air (12 h) fully restored the function of the devices within error (see Example 1.32). Heating the swatches was less effective: after exposure to $H_2S$, gentle heating of the swatch in air (70° C., 1 h) partially restored the performance of the sensors to >60% recovery for $Ni_3HHTP_2$ and >70% for $Ni_3HITP_2$ (see Example 1.32).

The nature of the observed recovery by washing suggests that the host guest interaction of metal to analyte is consistent with a Lewis acid binding site at the metal center. It is possible that axial water ligands bound to the metal center (shown to be present in an isoreticular MOF crystal structure) are displaced by more favorable binding with incoming analyte molecules upon analyte dosing. Displacement of adsorbed oxygen on the surface is also plausible. The electron donation provided by the bidentate chelation of catecholate or imino moieties to the metal center is known to increase the lability of the interaction between axial ligands and the metal center in octahedral Ni(II) complexes. Without being bound by theory, Applicants hypothesize that soaking of the analyte-saturated device in water can release the bound analyte through ligand displacement in water and restore the sensing ability of the SOFT-device.

SOFT-devices also displayed very good shelf lives. After standing exposed to ambient air for over a month (50 days), the resistance of the devices increased by 32% (average sheet resistance L=5 cm, fresh=0.81 $M\Omega/cm^2$, aged=1.1 $M\Omega/cm^2$). However, the chemiresistive sensing performances of the devices did not diminish with time, in spite of the increase in resistance (see Example 1.31).

Example 1.14. Summarized Fundamental Insight and Performance Advances from Chemiresistive Devices The sensing results summarized in FIGS. 4-5 highlight the novelty in the performances of these devices, and shed light on fundamental advances in understanding the charge transport properties and host/guest interactions of conductive MOFs. Important differences in the direction of the chemiresistive response were observed for $Ni_3HHTP_2$ and $Ni_3HITP_2$ in response to NO: an important observation in elucidating ligand-specific differences in the fundamental sensing mechanisms for charge perturbation in structurally similar MOFs. Without being bound by theory, Applicants propose that the chemiresistive responses for devices equilibrated in dry and humid $N_2$ suggest that $Ni_3HHTP_2$ behaves as a p-type semiconductor, while $Ni_3HITP_2$ could be a mixed-type (p/n) semiconductor. However, the charge transport mechanisms of these materials are highly complex, and ligand-specific differences in MOF structure, host-guest interactions, and charge transfer kinetics may exist. It is possible that the ligand-specific responses Applicants observe are consequences of these differences.

In terms of performance, the magnitude of device responses greatly exceeds the best previously reported results for this class of materials. Moreover, the direction of device response allows for facile differentiation of analytes, and finally, the capacity for the devices to detect analytes in the presence of $H_2O$ is highly desirable, since many chemiresistive devices are either sensitive to $H_2O$, or sensitive to pre-treatment conditions in the presence of $H_2O$.

Example 1.14. Analyte Breakthrough in Flow-Through SOFT-Devices

The intrinsic porosity of cloth is one of the notable advantages to utilizing fabric as a substrate in e-textiles. The capacity for chemical adsorption of gases hierarchically within the fabric and the integrated porous material offers an opportunity for pre-concentration of analytes, and/or simultaneous filtering and detection of gases. Related flexible systems, such as mixed matrix membranes (MMMs) or hybrid MOF/polymer composites, are effective functional components in gas sequestration and separations. These systems, however, have not yet been developed into effective, electrically-accessible sensors that detect capture and breakthrough. Since porous MOF-based membranes are widely known as functional systems capable of gas separation and sequestration, Applicants' SOFT-devices are optimal candidates for integration into an electronic sensor with filtration properties.

Figure 6:
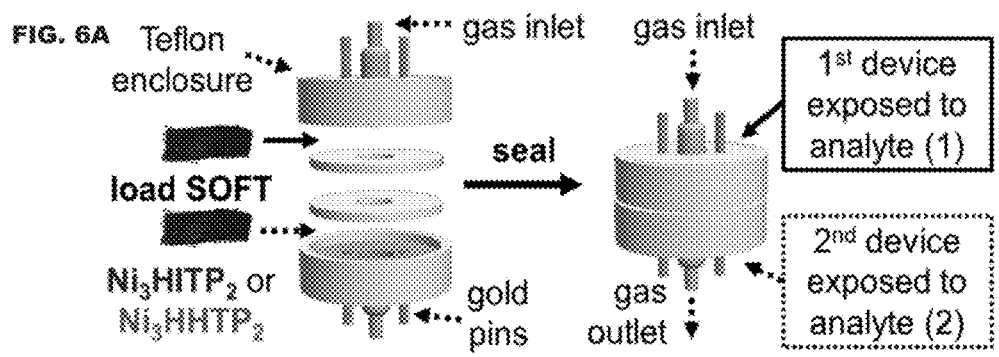
FIG. 6 shows breakthrough studies for simultaneous detection and capture of analytes.
Figure 6:
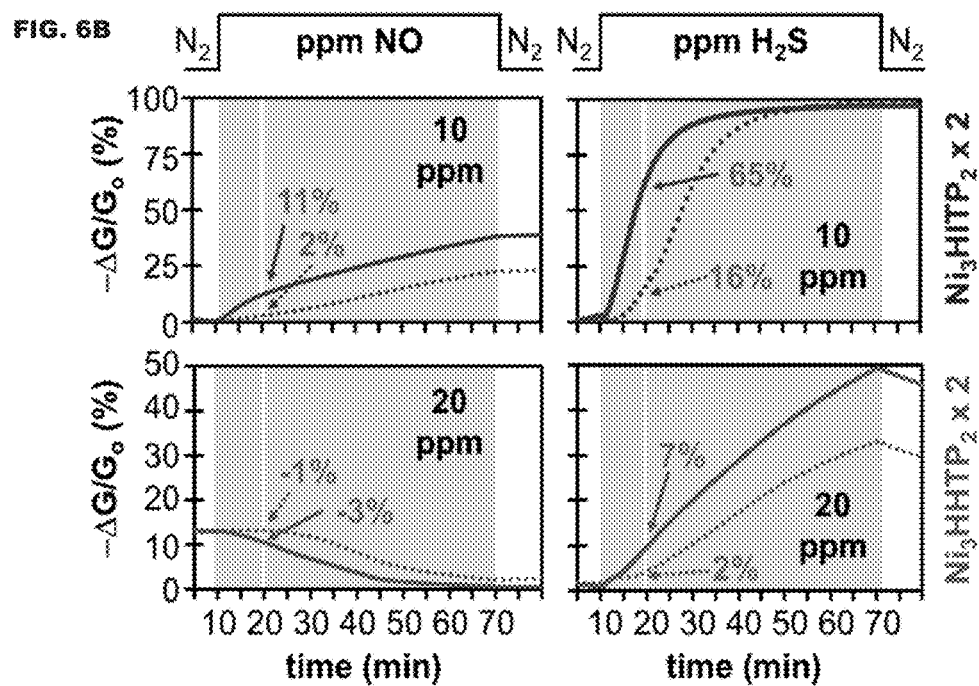

Applicants performed breakthrough studies employing two SOFT-sensors layered in a custom enclosure, shown in FIG. 6A. This experiment demonstrated potential for quantitative real-time detection and filtration of NO and $H_2S$ (FIG. 6B, Example 1.34) using SOFT-devices. The experiment was prepared such that the pressurized gas stream (gas flow=~0.5 L/min) must pass through a first SOFT-sensor, followed by free space (~0.20 $cm^3$), then a second SOFT-sensor (FIG. 6A). The chemiresistive response for each sensor was monitored continuously, and the devices were allowed to equilibrate in $N_2$ until a stable baseline current was observed. Devices were monitored for 10 minutes in dry $N_2$, then dosed with analyte for a span of 60 minutes before recovering in $N_2$.

To ensure that any capture of analyte was specific to the SOFT-device, and not to the cotton, Applicants performed experiments in some embodiments the first SOFT-device was replaced by unmodified cotton fabric. In these control experiments, breakthrough of analytes to the second membrane (SOFT-device) was not significantly attenuated upon dosing (see Example 1.34).

For breakthrough systems with two identical sensors (i.e., $Ni_3HHTP_2/Ni_3HHTP_2$ or $Ni_3HITP_2/Ni_3HITP_2$), analyte breakthrough showed attenuated response between the first and second sensor. For the sake of quantitative comparison, breakthrough responses at 10 minutes of analyte exposure were considered, and full representative traces shown in FIG. 6B. At 10 minutes of exposure to NO (10 ppm), $Ni_3HITP_2/Ni_3HITP_2$ increased in response by 11% for the first sensor, and only 2% for the second, corresponding to uptake of 0.4 mmol NO (~12.9 mmol NO/mg $Ni_3HITP_2$) before breakthrough (accounting for the volume of exposed SOFT-device). For $Ni_3HHTP_2/Ni_3HHTP_2$, 10 minutes of exposure to NO (20 ppm) caused a decrease in resistance of −3% for the first sensor and −1% for the second, equivalent to uptake of 0.8 mmol NO (~22.9 mmol NO/mg $Ni_3HHTP_2$). With exposure to $H_2S$ (10 ppm), $Ni_3HITP_2/Ni_3HITP_2$ devices increased in the response measured by the first sensor by 65%, and 16% for the second, corresponding to an estimated uptake of 0.4 mmol $H_2S$ before breakthrough, equivalent to ~12.3 mmol $H_2S$/mg $Ni_3HITP_2$. For $Ni_3HHTP_2/Ni_3HHTP_2$ exposed to $H_2S$ (20 ppm), an increase in response of 7% for the first sensor and 2% for the second was recorded after 10 minutes of exposure: an estimated uptake of 0.7 mmol $H_2S$ before breakthrough (~23.8 mmol $H_2S$/mg $Ni_3HHTP_2$).

The results shown in FIG. 6B reflect a remarkable capacity for SOFT-devices to simultaneously detect and capture analytes below their permissible exposure limits. The practical implications of such results are highly promising with respect to applications of SOFT-sensors in novel portable filtering and sensing technology. A gas mask that employed one or more layers of SOFT-sensor would allow for a warning to be transduced before user exposure to toxins, with a pre-determined breakthrough rate based on analyte concentration.

Example 1.15. Conclusion

This Example describes the first example of flexible, textile-supported chemiresistive sensors employing conductive metal-organic frameworks (MOFs) as functional materials. The use of direct assembly produces robust e-textiles over large areas, and their preparation from direct assembly of monomers to produce conformal coatings of conductive material at the fiber level is efficient, straightforward, and requires no specialized equipment. The SOFT-device arrays represent a novel class of smart fabric sensors that are mechanically robust, and capable of simultaneous, quantitative detection uptake, and differentiation of hazardous gases.

The SOFT-devices reported herein serve as the first example of e-textiles employing MOFs as the functional component, and possess at least three unique performance characteristics of broad potential utility in gas detection and capture. First, $Ni_3HITP_2$ and $Ni_3HHTP_2$ SOFT-devices serve as the first single-platform e-textile sensor capable of detecting both NO (LOD=0.16 and 1.4 ppm, respectively, 0.1-80 ppm) and $H_2S$ (LOD=0.52 and 0.23 ppm, respectively, 1-80 ppm), and constitute the best MOF-based chemiresistors for NO and $H_2S$ detection. Second, these devices retain their performance in 18% humidity, and are fully recoverable and washable. Third, a single SOFT-device effectively sequesters NO or $H_2S$ in simultaneous uptake and detection step, providing predictable rates of breakthrough based on analyte concentration.

While these systems are robust, they may lose mass upon handling that involves cutting or puncturing of the fabric due to fraying or MOF shedding. This limitation could be overcome by the introduction of a porous polymeric coating, which would add long term stability to the device, but still be permeable enough to allow perfusion of gaseous analytes and/or water to the SOFT swatch.

The behavior of SOFT-devices provides fundamental insight on properties of this class of conductive MOFs, including mechanistic details of analyte interaction and change transport. The dosimetric responses of SOFT-devices to analytes are entirely recoverable by washing, which suggests metal-analyte binding interactions that are consistent with labile Lewis acid site coordination. The direction of the dosimetric responses implies that $Ni_3HITP_2$ is a mixed semiconductor, while $Ni_3HHTP_2$ may be primarily p-type in nature.

Example 1.16. General Methods

Chemicals were purchased from Sigma Aldrich or TCI and used as received. Powder X-ray diffraction (PXRD) data was gathered using a Bruker D8 diffractometer. Spectra are presented with the background subtracted and corrected for K-α. Scanning Electron Microscopy (SEM) and Energy Dispersive X-ray Spectroscopy (EDS) were performed using a Hitachi TM3000 SEM equipped for X-ray microanalysis with a Bruker Edax light element Si(Li) detector. Applicants obtained Thermal Gravimetric Analysis (TGA) traces using a TA instruments TGA Q50 with platinum pans. Self-Organized Frameworks on Textiles (SOFT) swatches were prepared using cotton and batting substrates purchased at Jo-Ann Fabrics.

Example 1.17. Templated and General Synthesis of Compounds

A general reaction scheme for the synthesis hexaaminotriphenylene. Is illustrated in Scheme 1.

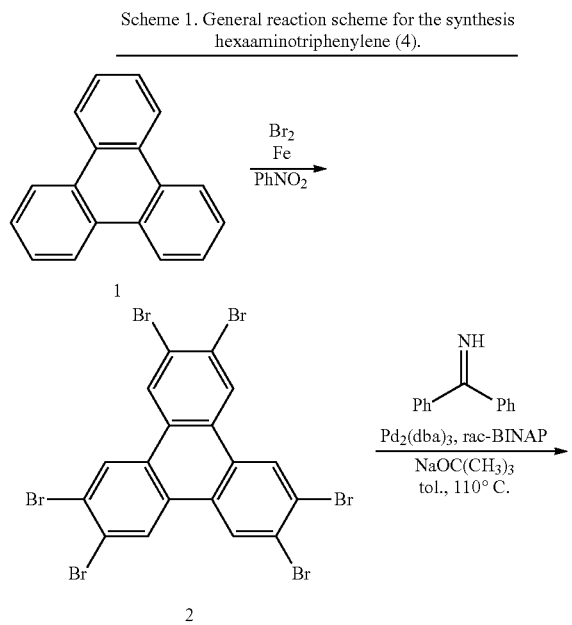

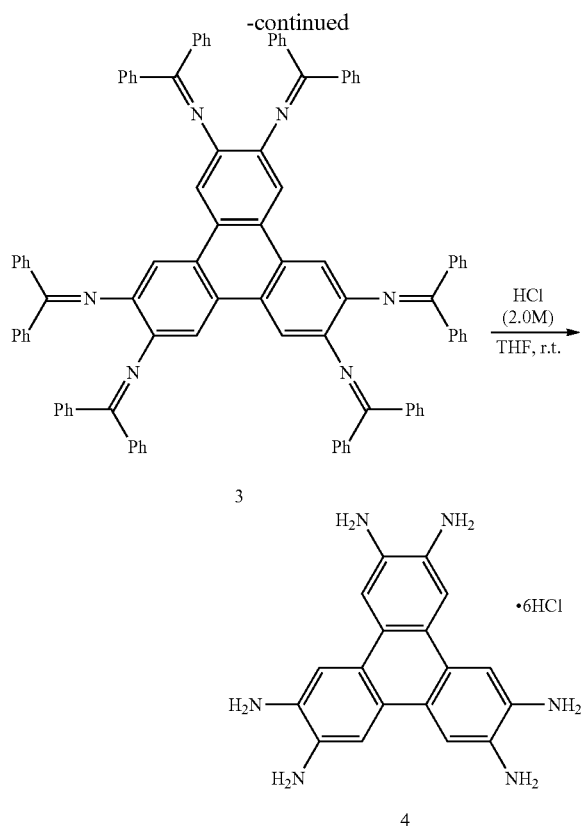

3

4 ·6HCl sure and purified by column chromatography (eluent 1:8 ethyl acetate:hexanes). The brightly colored orange product 3 (1.83 g, yield=98%) was isolated and dried under reduced pressure. This solid was most easily transferred by dissolving in a carrier solvent first. Characterization matched reported analysis.

To prepare compound 4, compound 3 (0.330 mmol, 430 mg) was dissolved in tetrahydrofuran (16.5 mL) and 2.0 M hydrochloric acid (1.98 mmol, 1.0 mL) was added. Upon addition of acid, an immediate color change was observed (orange to red) and a precipitate began to form. The mixture was stirred at room temperature for 30 minutes, then the fine white powder precipitate filtered over a very small diameter fritted funnel (~1 cm diameter: this procedure minimizes the loss of product through the filter). The white solid was washed with tetrahydrofuran (2 mL), and dried under reduced pressure, affording 4 (105 mg, yield=59%). Characterization matched reported analysis.

Scheme 2 illustrates the general reaction scheme for the synthesis hexahydroxytriphenylene.

Scheme 2. General reaction scheme for the synthesis hexahydroxytriphenylene (7).

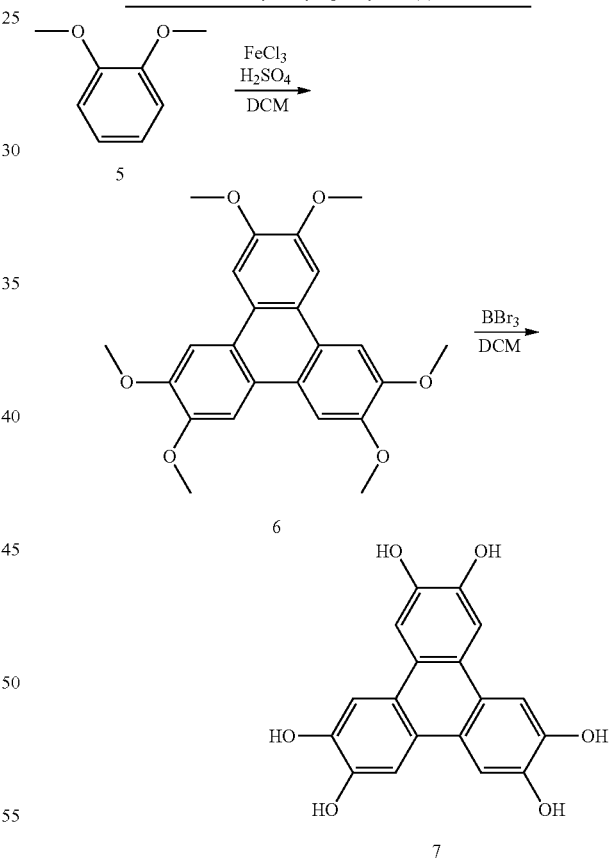

For synthesis of compound 2, a solution of 4.95 mmol triphenylene (1, 1.13 g) in nitrobenzene (40 mL) was prepared in a round-bottomed flask. Catalytic iron shavings (1.78 mmol, 100 mg) were added, and the reaction flask was equipped with a dropping funnel. Liquid bromine (42.6 mmol, 2.2 mL) was added dropwise over 10 minutes. The resulting solution was left to stand for 16 hours, then refluxed at 205° C. for 2 hours. The reaction solution was allowed to cool to room temperature, at which point diethyl ether was added (150 mL), and the resulting solid precipitate was filtered and rinsed with diethyl ether (2×30 mL). The solid was taken up in dichlorobenzene (60 mL), heated to reflux, then allowed to cool to room temperature then chilled (0° C.). The white solid was filtered, rinsed with diethyl ether (2×30 mL), then dried under reduced pressure at 52° C. The resulting off-white solid product 2 (3.18 g, yield=92%) was used without further purification. Characterization matched reported analysis.

For synthesis of compound 3, to a flame-dried Schlenk flask sparged with nitrogen was added tris(dibenzylidenacetone)dipalladium(0) (0.343 mmol, 314 mg) and racemic-BINAP (0.686 mmol, 427 mg). Degassed toluene (35 mL) was added to the vessel, and the solution subjected to four freeze-pump-thaw cycles, finally filling the vessel with nitrogen. The vessel was heated to 110° C. for 30 minutes with stirring, then allowed to return to room temperature. Under positive pressure of nitrogen, 2 (1.43 mmol, 1.0 g), benzophenone imine (11.1 mmol, 1.9 mL), and sodium tert-butoxide (11.1 mmol, 1.1 g) were added to the reaction vessel. The solution was stirred at 110° C. overnight under nitrogen, then allowed to cool to room temperature. The reaction was diluted with dichloromethane (20 mL), then filtered over a pad of Celite, rinsing with dichloromethane (20 mL). The filtrate was concentrated under reduced pres- To prepare compound 6, 36.2 mmol of veratrole (5, 4.6 mL) was dissolved in dichloromethane (25 mL). In a separate flask, 108.6 mmol of iron (III) chloride (17.6 g) was suspended in dichloromethane (50 mL), and concentrated sulfuric acid (0.25 mL) was added dropwise at 0° C. The solution containing dissolved veratrole was added dropwise to the iron (III) chloride solution at 0° C. over 15 minutes. The resulting solution was allowed to slowly return to room temperature over 3 hours with stirring. At this stage, methanol was added very slowly to quench the reaction (75 mL). The first portion (25 mL) of methanol was added milliliter at a time (dropwise), until the reaction was transformed from a thick, tarry black slurry to a smooth opaque yellow suspension. Once the methanol had been fully added, the reaction was stirred for 30 minutes then filtered. The white solid was washed thoroughly with methanol (5×50 mL), then dried under reduced pressure at 52° C., affording pure compound 6 (4.93 g, yield=89%). Characterization matched reported analysis.

To synthesize compound 7, compound 6 (4.9 mmol, 2.0 g) was dissolved in dichloromethane (15 mL), and 34.3 mmol boron tribromide (3.3 mL) was added dropwise at 0° C. The reaction solution was allowed to return to room temperature with stirring, and stirred at room temperature overnight. The reaction was quenched with slow addition of water (20 mL) to which brine was added (15 mL), then extracted with ethyl acetate (6×100 mL). Combined organic layers were washed with water (1×200 mL), dried over magnesium sulfate, and concentrated under reduced pressure to afford pure compound 7 as a gray solid (1.55 g, yield=97%). Characterization matched reported analysis.

The general synthetic scheme for metal-organic frameworks $Ni_3HHTP_2$ and $Ni_3HITP_2$ is illustrated in Scheme 3.

Scheme 3 General synthetic scheme for metal-organic frameworks $Ni_3HHTP_2$ and $Ni_3HITP_2$. Proposed structure assumes the metal to be in the +2 oxidation state and the total electrical neutrality of the resulting framework. The redox state of triphenylene is based on the redox activity of functionalized triphenylenes in analogous molecular complexes.

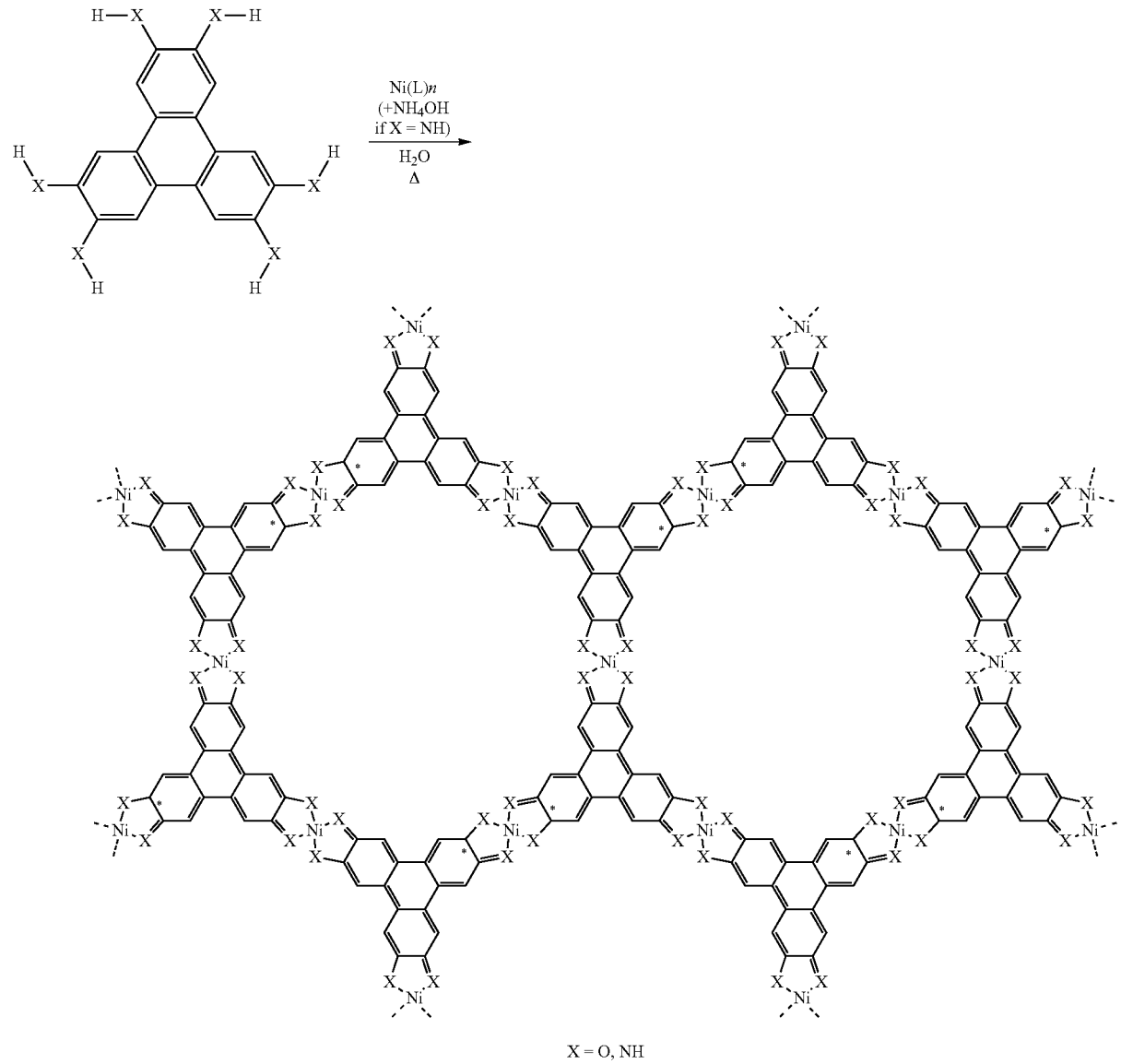

X = O, NH

Example 1.18. Templated Synthesis of $Ni_3HHTP_2$ MOF on Textiles

To prepare SOFT-sensors, 0.111 mmol hexahydroxytriphenylene (36 mg) and 0.222 mmol nickel (II) acetate (55 mg) were added to a 20 mL scintillation vial. A single fabric swatch, either cotton or batting, was added with the solids (1.5×3 cm). Deionized water (3.2 mL) was added such that the swatch was fully dampened. The vial was capped and the reaction mixture subjected to sonication (5 min), then heated with stirring (solution at 85° C.) overnight. The resulting solution was allowed to cool, and the fabric swatch isolated from the vial, then submerged in DI water (5 mL, 5 min) to wash. The washed fabrics were rinsed with a small amount (1-2 mL) of acetone to activate the MOFs and remove any residual starting materials and bi-products. The resulting activated textile swatch was drip-dried in air for a minimum of 6 hours. The remaining solid in the flask was isolated via filtration, washed with water (2×5 mL) and acetone (1×5 mL), and dried under reduced pressure. This solid was compared to bulk MOF for characterization purposes.

Figure 7:
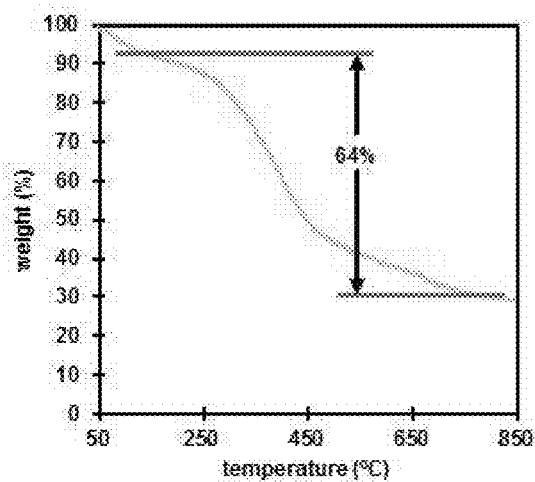
FIG. 7 shows various thermal gravimetric analysis (TGA) curves.
Figure 7:
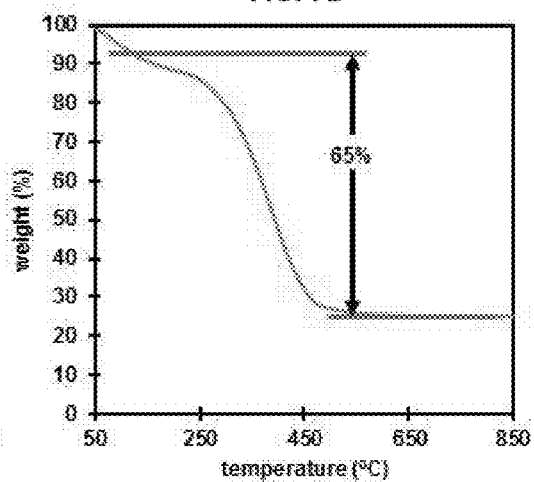
Figure 8:
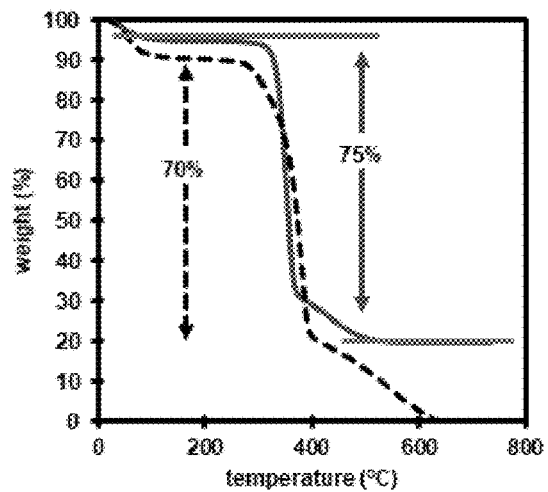
FIG. 8 shows additional TGA curves.
Figure 8:
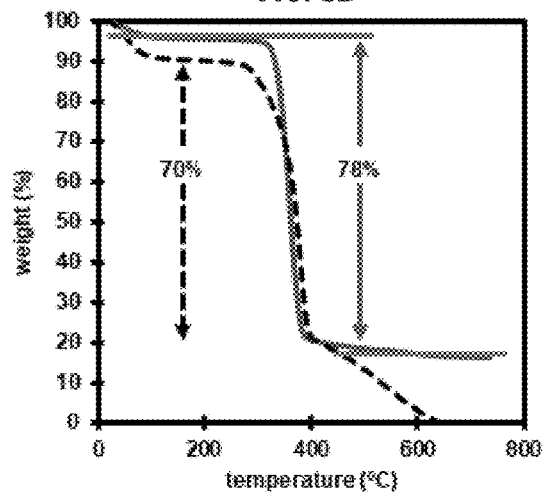
Figure 9:
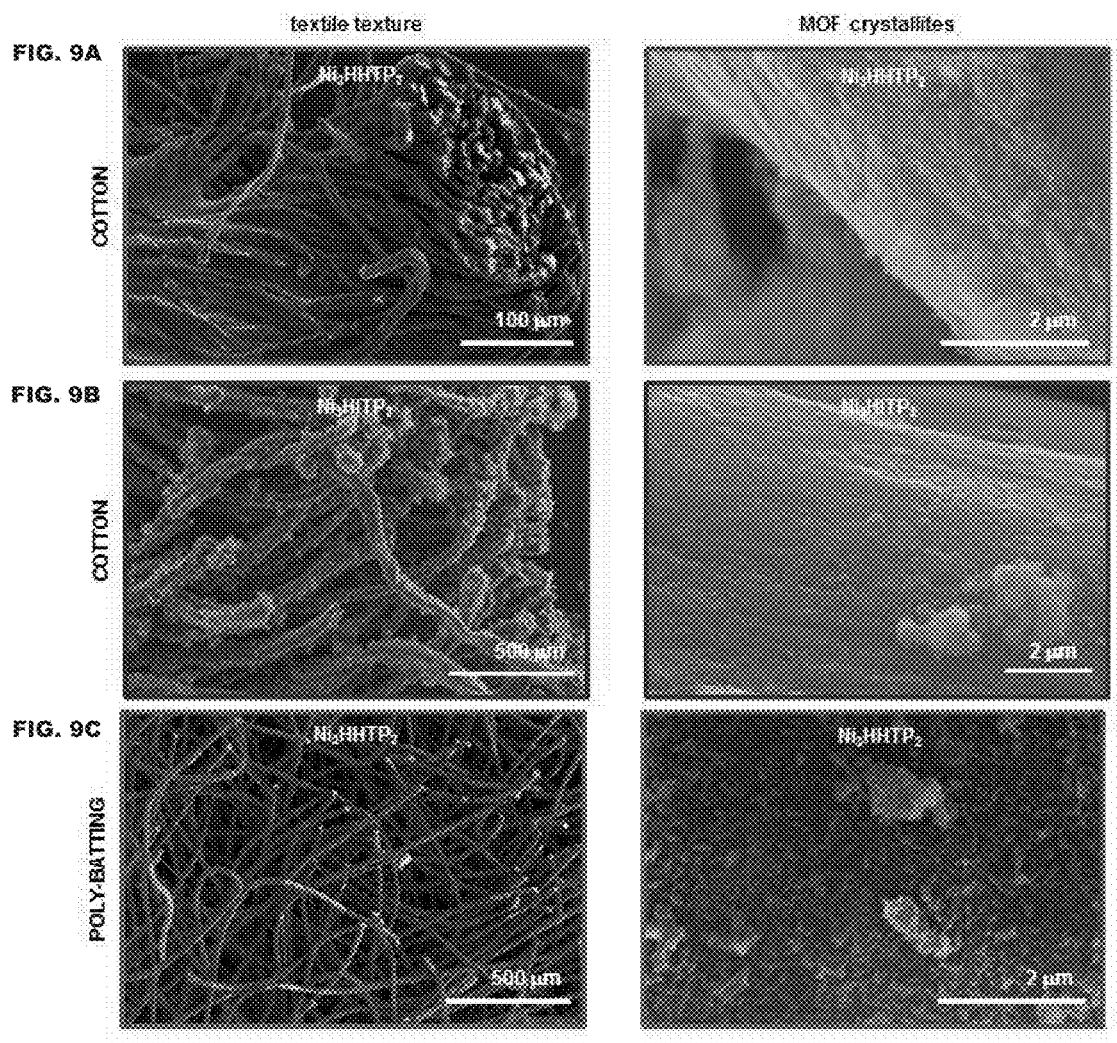
FIG. 9 shows sequentially magnified (increasing left to right) cross-sectional scanning electron micrographs of $Ni_3HHTP_2$ assembled on cotton textile (FIG. 9A), $Ni_3HITP_2$ assembled on cotton (FIG. 9B), and $Ni_3HHTP_2$ assembled on poly-batting (FIG. 9C), illustrating perfusion of crystallites through the material.

Analogous conditions were used to synthesize MOFs in solution for characterization, although the synthesis of pure MOF omitted the added fabric. Reaction mixtures were filtered, solids rinsed with water and acetone, and dried thoroughly under vacuum. Characterization matched reported analyses for TGA (FIG. 7), PXRD (FIG. 8), and EDS (FIG. 9).

TABLE 1

Mass of $Ni_3HHTP_2$ assembled per unit surface area for SOFT-sensors.

| $Ni_3HHTP_2$ Trial # | Fabric surface area (cm$^2$) | Fabric mass (mg) | SOFT-sensor mass (mg) | Mass MOF @ SOFT-sensor (mg) | mg/cm$^2$ |
|---|---|---|---|---|---|
| 1 | 4.5 | 59.4 | 69.4 | 10 | 2.2 |
| 2 | 4.5 | 52.6 | 52.6 | 7.1 | 1.6 |
| 3 | 16 | 149 | 178.1 | 29.1 | 1.8 |

$Ni_3HHTP_2$: Average mass MOF/square cm: 1.9 ± 0.3 mg/cm$^2$

Example 1.19. Templated Synthesis of $Ni_3HITP_2$ MOF on Textiles

To prepare SOFT-sensors, 0.067 mmol hexaiminotriphenylene (36 mg) was dissolved in deionized water (1.0 mL) in a 20 mL scintillation vial. A solution of 0.134 mmol $NiCl_2.6H_2O$ (32 mg), concentrated ammonium hydroxide (0.1 mL), and a single cotton fabric swatch (1.5×3 cm) in deionized water (2.2 mL) was prepared separately, then added all at once to the HITP solution. The vial was capped and the reaction mixture subjected to sonication (5 min), then heated with stirring (solution at 85° C.) overnight. The resulting solution was allowed to cool, and the fabric swatch isolated from the vial, then submerged in DI water (5 mL, 5 min) to wash. The washed fabrics were rinsed with a small amount of acetone (1-2 mL) to activate the MOFs and remove any residual starting materials and bi-products. The resulting activated textile swatch was drip-dried in air for a minimum of 6 hours. The remaining solid in the flask was isolated via filtration, washed with water (2×5 mL) and acetone (1×5 mL), and dried under reduced pressure. This solid was compared to bulk MOF for characterization purposes.

Figure 10:
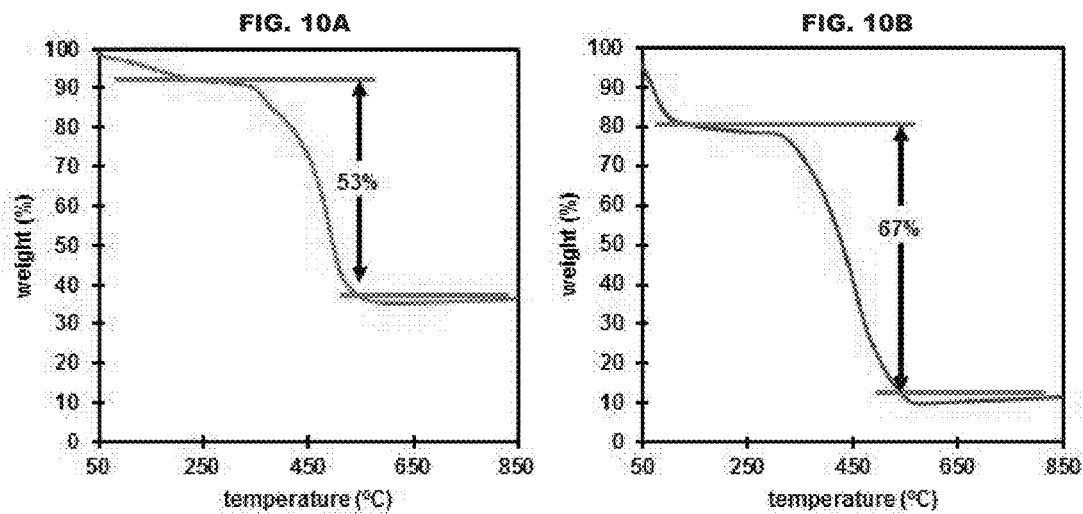
FIG. 10 shows additional TGA curves.
Figure 11:
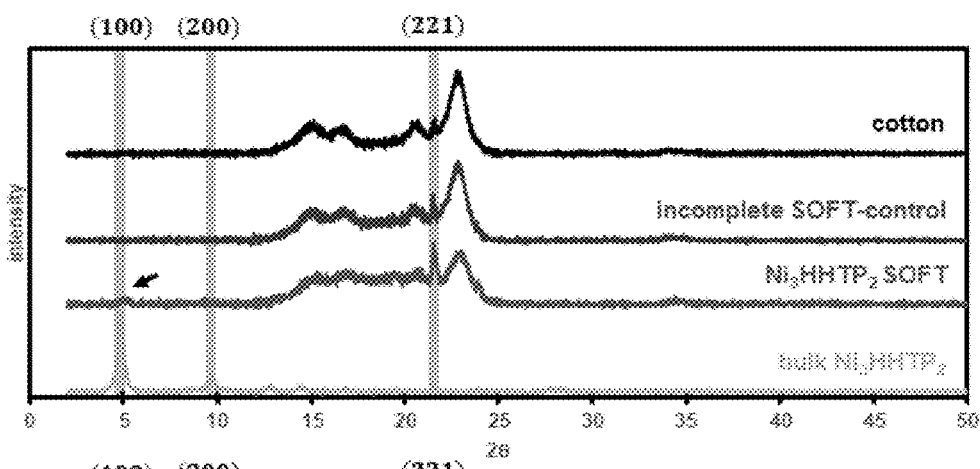
FIG. 11 shows crystallographic information for $Ni_3HHTP_2$ devices, substrates, controls, and bulk. Relevant Bragg planes are highlighted in gray.
Figure 11:
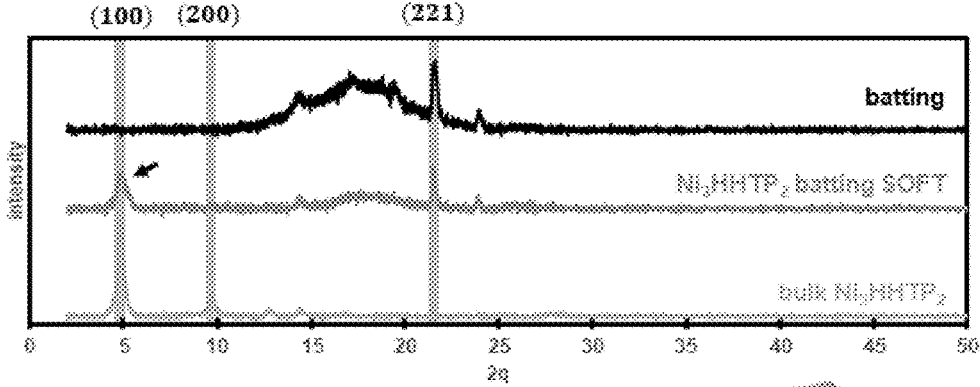
Figure 11:
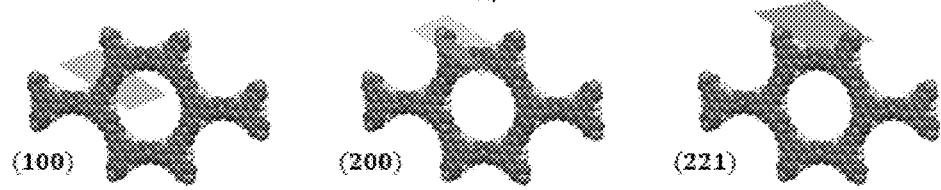
Figure 12:
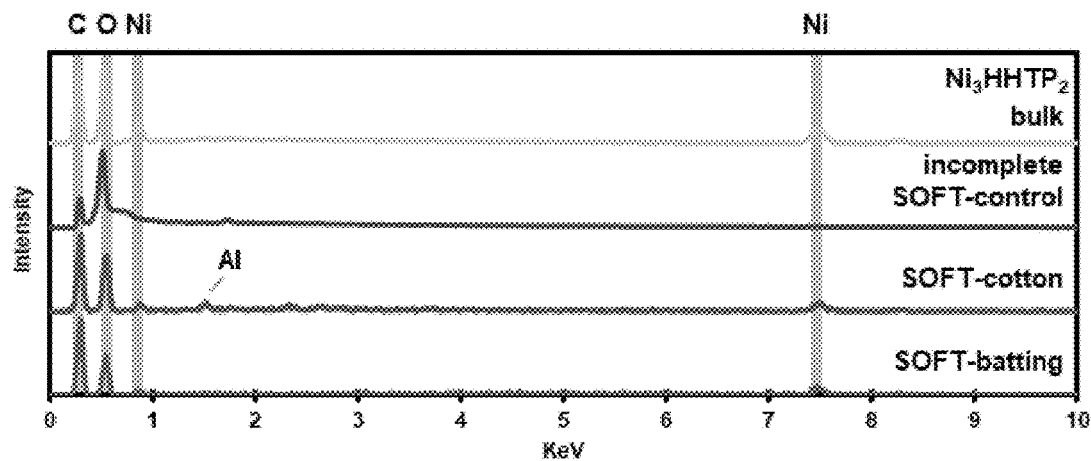
FIG. 12 shows energy dispersive spectroscopy of (top to bottom) bulk $Ni_3HHTP_2$ MOF (yellow), incomplete cotton SOFT-device saturated with starting materials (brown), $Ni_3HHTP_2$ assembled on cotton (red), and $Ni_3HHTP_2$ MOF assembled on poly-batting (green), normalized to the highest peak, with all peaks labeled. Aluminum is present in the cotton/MOF trace, which is attributed to trace elements from the weaving process. Lack of resolution for the trace elements in the control sample reflects the lack of widespread MOF assembly, but the presence of peaks corresponding to nickel confirm the presence of the components.
Figure 13:
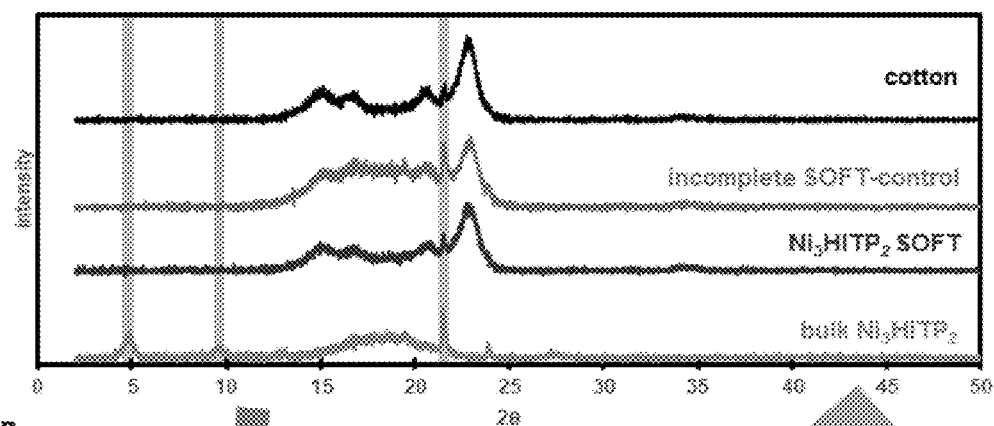
FIG. 13 shows crystallographic information for $Ni_3HITP_2$ devices, substrates, controls, and bulk.
Figure 13:
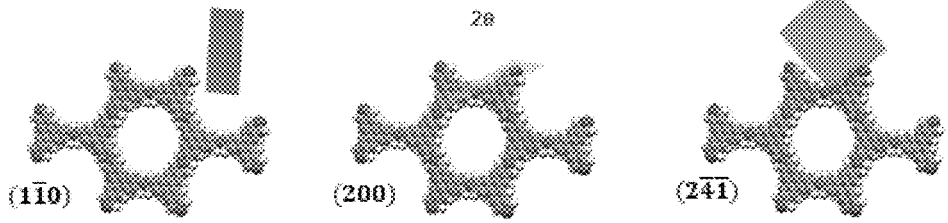
Figure 14:
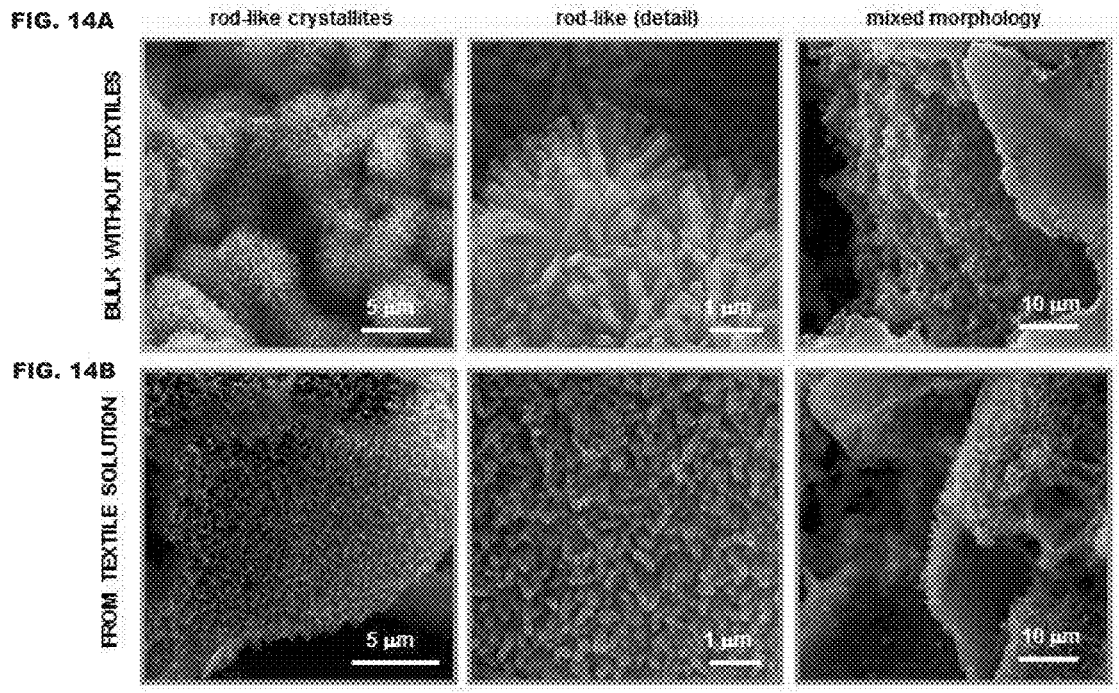
FIG. 14 shows various scanning electron micrographs (SEMs).
Figure 15:
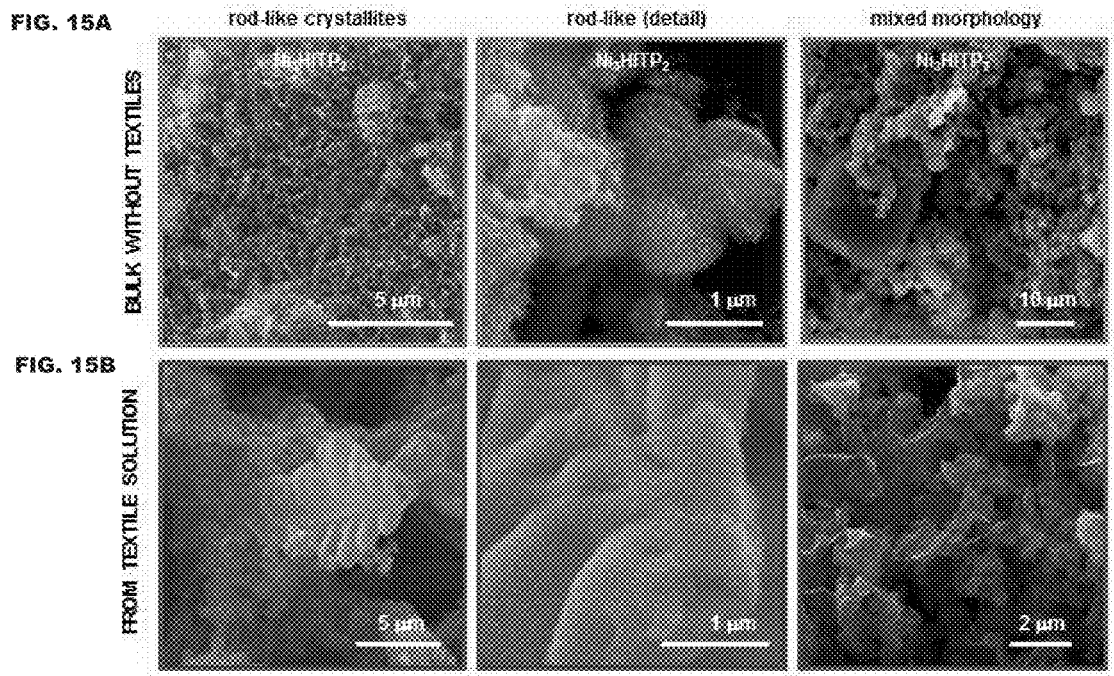
FIG. 15 shows additional SEMs.
Figure 17:
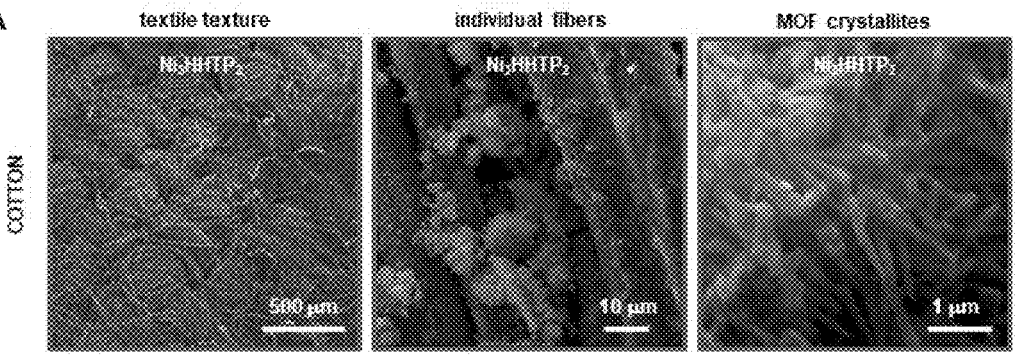
FIG. 17 shows sequentially magnified (increasing left to right) scanning electron micrographs of $Ni_3HHTP_2$ MOF assembled on cotton textile (FIG. 17A), $Ni_3HITP_2$ assembled on cotton (FIG. 17B), and $Ni_3HHTP_2$ assembled on poly-batting (FIG. 17C).
Figure 17:
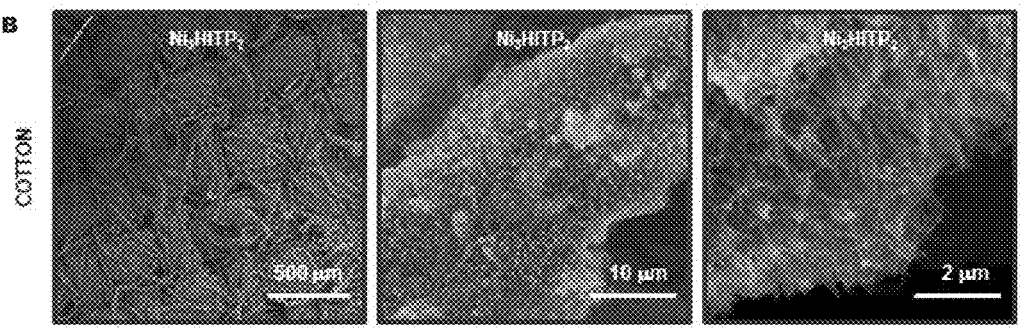
Figure 17:
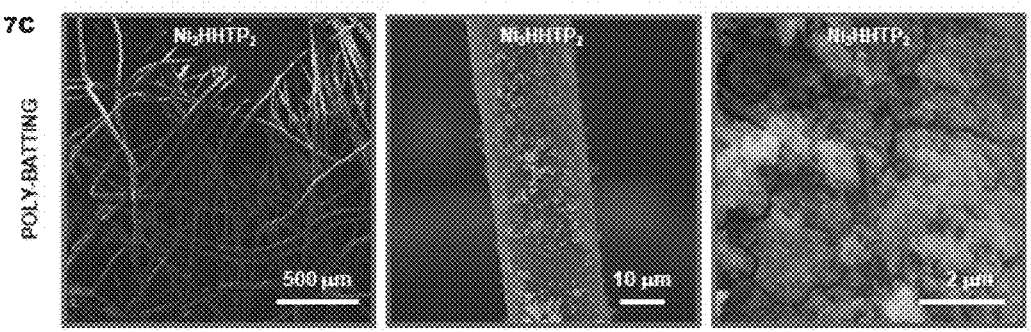
Figure 18:
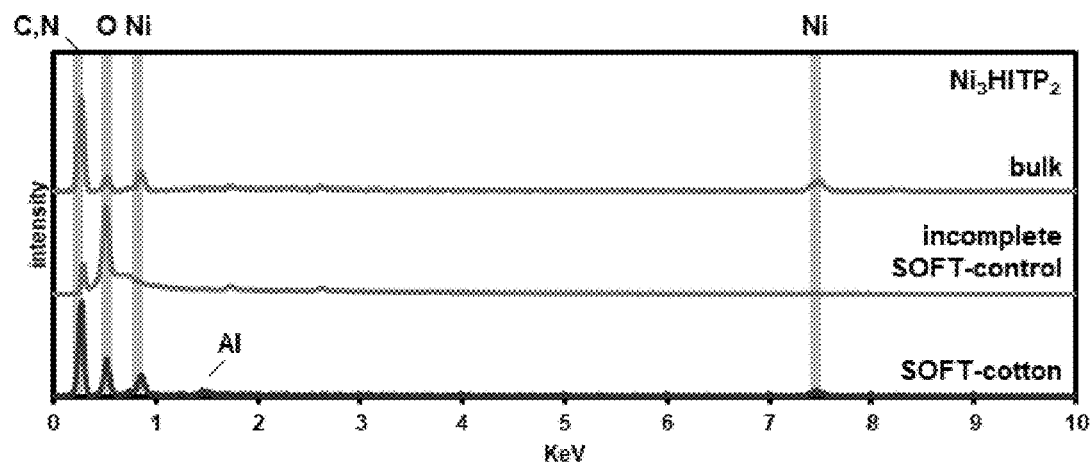
FIG. 18 shows energy dispersive spectroscopy of (top to bottom) bulk $Ni_3HITP_2$ MOF (pink), incomplete cotton SOFT-device saturated with starting materials (grey), and $Ni_3HITP_2$ assembled on cotton (blue), normalized to the highest peak, with all peaks labeled. The presence of aluminum in the cotton/MOF trace is attributed to trace elements from the weaving process. Lack of resolution for the trace elements in the control sample reflects the lack of widespread MOF assembly, but the presence of peaks corresponding to nitrogen and nickel confirm the presence of the components.

To prepare bulk MOF, 0.111 mmol hexaaminotriphenylene (3, 60 mg) was dissolved in deionized water (30 mL). A solution of 0.167 mmol $NiCl_2.6H_2O$ (40 mg) and concentrated ammonium hydroxide (1.8 mL) in deionized water (30 mL) was prepared separately, and added all at once to the triphenylene containing solution. This mixture was gently stirred (3 hours) at 65° C. The resulting mixture was allowed to cool, and then filtered; the solids were rinsed with water and acetone, and dried thoroughly under vacuum. Characterization matched reported analyses for TGA (FIG. 10), PXRD (FIG. 11), and EDS (FIG. 12).

TABLE 2

Mass of $Ni_3HHTP_2$ assembled per unit surface area for SOFT-sensors.

| $Ni_3HITP_2$ Trial # | Fabric surface area (cm$^2$) | Fabric mass (mg) | SOFT-sensor mass (mg) | Mass MOF @ SOFT-sensor (mg) | mg/cm$^2$ |
|---|---|---|---|---|---|
| 1 | 4.5 | 56.3 | 63.4 | 7.1 | 1.6 |
| 2 | 4.5 | 42.9 | 48.4 | 5.5 | 1.2 |
| 3 | 4.5 | 43.1 | 47.3 | 4.2 | 0.9 |

$Ni_3HITP_2$: Average mass MOF/square cm: 1.2 ± 0.3 mg/cm$^2$

Example 1.20. Thermal Gravimetric Analysis of MOFs

Thermal gravimetric analysis was performed using a TA Instruments TGA Q150 with a 40° C./min ramp from room temperature to 900° C.

Example 1.21. Powder X-Ray Diffraction

Powder X-Ray Diffraction (PXRD) was performed using a Bruker D8 Diffractometer. Homogenized, flat powder samples were analyzed in a 25 mm diameter zero diffraction PMMA sample holders plates (8.5 mm height, Bruker) equipped with zero diffraction silicon crystal plates (24.6 mm×1.0 mm, MTI Corp., ~5 mg sample size). Textiles, control experiments, and textile impregnated with MOF were mounted onto the same sample holders in swatches (2×1 cm). A very small amount of petroleum jelly was used on the underside of the fabric sample to immobilize the swatches.

The sample details are summarized herein: Cotton or Batting Substrate: fabric controls, no treatment; Bulk MOF: $Ni_3HHTP_2$ or $Ni_3HITP_2$ prepared using the method detailed in Example 1.17; SOFT-devices: and $Ni_3HHTP_2$ assembled on cotton or batting using the method detailed in Example 1.18, or $Ni_3HITP_2$ assembled on cotton using the method described in Example 1.19. As a control, Applicants prepared cotton samples saturated with starting material MOF-precursors, but did not allow the MOF to fully crystallize. Applicants followed the procedure for direct self-assembly of MOFs on textiles described in Examples 1.18-1.19, except Applicants sonicated these samples for only 1 minute, and did not heat the reaction vial (reaction performed at ambient temperature). Applicants removed the swatches from the reaction quickly (5 min) to ensure that crystallization did not occur. The resulting swatches were non-conductive.

Example 1.22. Scanning Electron Microscopy

Scanning electron microscopy of bulk MOFs and MOFs assembled on textiles was obtained using a using a Hitachi TM3000 SEM with a 15.0 kV beam. Images are shown in FIGS. 9 and 14-17.

Example 1.23. Energy Dispersive X-Ray Spectroscopy of MOFs

Energy dispersive X-Ray spectroscopy was collected using SDD X-ray microanalysis system with Octane Pro 10 sq. mm detector and TEAM software.

Example 1.24. Brunauer-Emmett-Teller Isotherms

Figure 19:
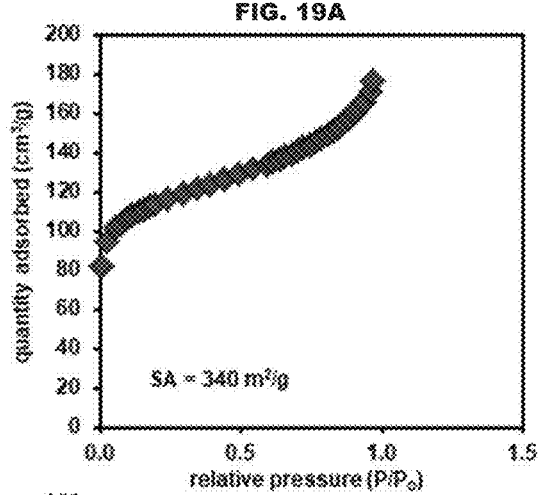
FIG. 19 shows isotherms and BET surface areas (SA) with argon at 77 K for bulk $Ni_3HITP_2$ MOF (purple) (FIG. 19A), $Ni_3HITP_2$ assembled on cotton (blue) (FIG. 19B), bulk $Ni_3HHTP_2$ MOF (orange) (FIG. 19C), and $Ni_3HHTP_2$ assembled on cotton (red) with argon (FIG. 19D). SA unaltered cotton=0.3 $m^2/g$. Degas=120° C., 24 h (all samples).
Figure 19:
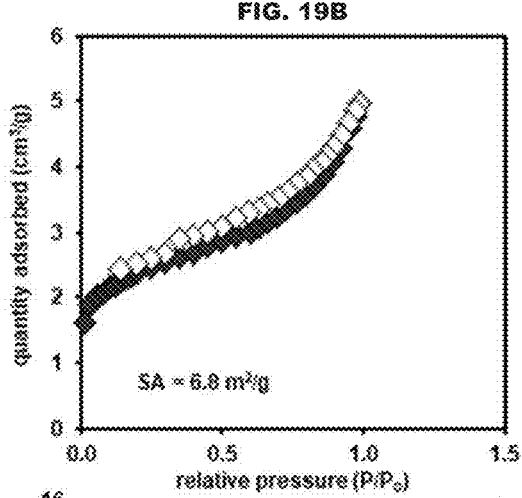
Figure 19:
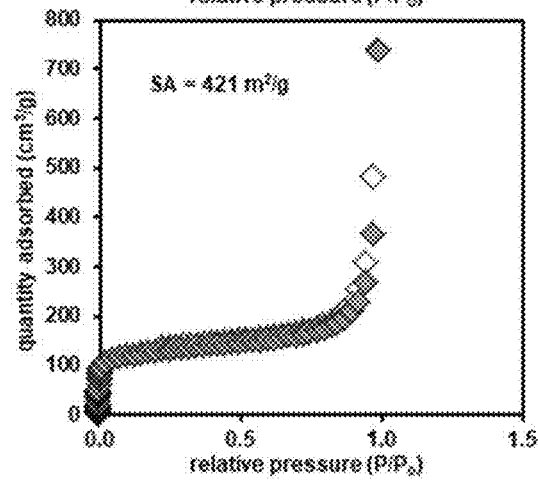
Figure 19:
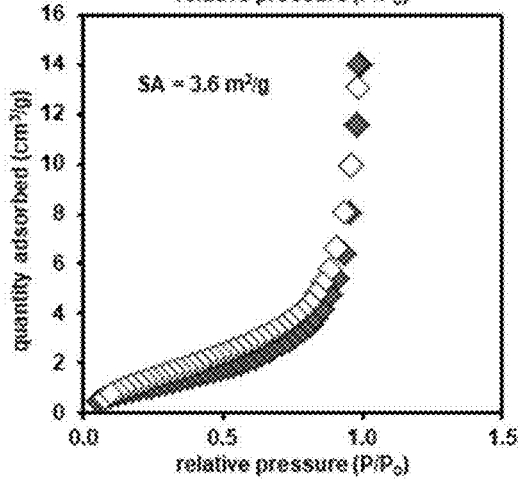
Figure 20:
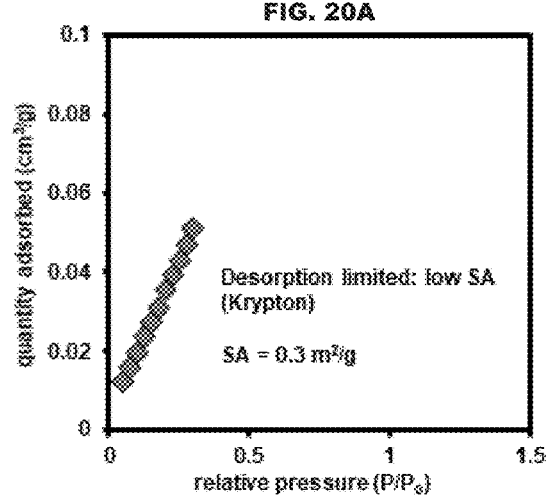
FIG. 20 shows additional isotherms and BET surface areas.

Brunauer-Emmett-Teller Isotherms are shown in FIGS. 19-20.

Example 1.25. Measurement of Sheet Conductance of SOFT-Sensors

A 2-point probe method was employed to collect sheet conductance σ (S/cm) measurements of SOFT-sensors according to Equation 1.

$$\sigma = \frac{I}{V} \times \frac{L}{WT} \quad \text{Equation 1}$$

Herein, I (A) is the current, V (V) represents voltage, L (cm) corresponds to the distance between probes, and W and T (cm) account for the width and thickness of the SOFT-sensor, respectively.

Using this method, Applicants calculated sheet conductance for cotton SOFT-sensors. Conductance for sensors employing $Ni_3HHTP_2$ equals $(1.6 \times 10^{-4}) \pm (2.2 \times 10^{-6})$ S/cm. Conductance for sensors employing $Ni_3HITP_2$ equals $(2.6 \times 10^{-3}) \pm (3.5 \times 10^{-4})$ S/cm.

Example 1.26. Semiconductive Behavior of SOFT-Devices

To generate the plots shown in FIG. 21, Applicants loaded SOFT-device samples (equipped with leads) onto a hot plate heating element open to air. The leads were connected to a potentiostat (PalmSense), and a 1.0 V bias applied. The hot plate was gradually heated in a stepwise fashion, and allowed to stabilize at each temperature point (3 minutes). The ensuing current was monitored, and averaged over ten seconds.

Thermal band gap was calculated using the data shown in FIG. 21 and Equation 2. The natural log of current I (Amperes) was plotted against the reciprocal temperature in Kelvin. Linear regression of the data points supplied a best fit equation.

$$m = \frac{-E_g}{2 \times k_B} \quad \text{Equation 2}$$

Herein, m represents slope of least squares, $k_B$ is Boltzmann constant, and $E_g$ corresponds to thermal band gap. The thermal band gap was calculated to equal 0.63 eV for $Ni_3HITP_2$, and 0.64 eV for $Ni_3HHTP_2$.

Example 1.27. Current/Voltage Plots

Data for current/voltage plots were collected using portable EmSTAT potentiostats. The plots are shown in FIG. 22.

Example 1.28. Scalability, Flexibility, and Robustness of Devices

Figure 23:
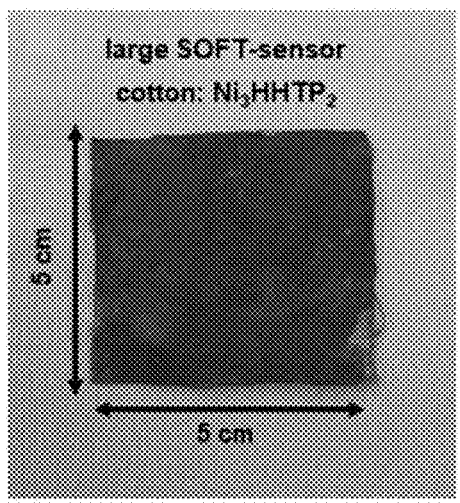
FIG. 23 demonstrates the scalability of SOFT-sensor fabrication.
Figure 23:
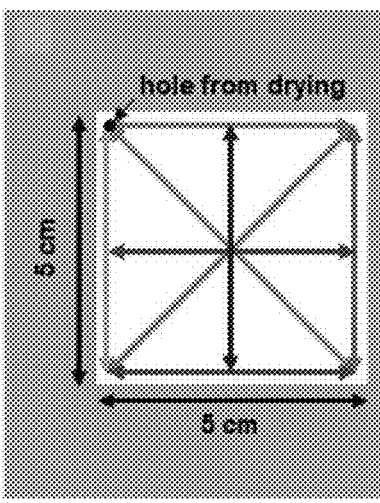

Results related to the scalability, flexibility and robustness of devices are summarized in FIG. 23 and Tables 3-5.

TABLE 3

Mass of $Ni_3HHTP_2$ assembled into textile platform versus isolated in bulk from reaction solution and percent uptake of MOF.

| $Ni_3HHTP_2$ Trial # | mass MOF @ SOFT-sensor (mg) | mass bulk MOF (mg) | total MOF mass (mg) | percent MOF loaded onto fabric |
|---|---|---|---|---|
| 1 | 6.7 | 30.0 | 36.7 | 18% |
| 2 | 5.1 | 41.7 | 46.8 | 11% |
| 3 | 4.4 | 39.4 | 43.8 | 10% |

$Ni_3HHTP_2$: Average % MOF loaded on textile: 13 ± 5%

TABLE 4

Mass of $Ni_3HITP_2$ assembled into textile platform versus isolated in bulk from reaction solution and percent uptake of MOF.

| $Ni_3HITP_2$ Trial # | mass MOF @ SOFT-sensor (mg) | mass bulk MOF (mg) | total MOF mass (mg) | percent MOF loaded onto fabric |
|---|---|---|---|---|
| 1 | 4.2 | 22.5 | 26.7 | 16% |
| 2 | 5.5 | 11.0 | 16.5 | 33% |
| 3 | 7.1 | 16.0 | 23.1 | 31% |

$Ni_3HITP_2$: Average % MOF loaded on textile: 27 ± 10%

TABLE 5

Resistance measurements for dipcoating fabric swatches into suspensions of bulk MOF particulates. An 11 mg mixture (similar to the final solution concentration for preparing SOFT-devices: 16 mg MOF/1.5 mL solvent) of bulk MOF suspended in solvent was prepared and sonicated for homogeneity (2 minutes). Swatches of cotton (1.5 × 1 cm) were dipcoated into these suspensions, rinsed with acetone, dried fully, and their resistance tested. These steps were repeated until the entire suspension had been taken up by the swatch (marked 'end' in the table). Applicants were unable to generate a conductive pathway using this method, as shown below.

| | Resistance of Dipcoated Swatch | | | |
|---|---|---|---|---|
| | $Ni_3HHTP_2$ suspended in: | | $Ni_3HITP_2$ suspended in: | |
| Trial # | acetone | distilled water | acetone | distilled water |
| 1-21 | ∞ | ∞ | ∞ | ∞ |
| 22 | ∞ | ∞ | ∞ (end) | ∞ |
| 23 | ∞ | ∞ | | ∞ |
| 24 | ∞ (end) | ∞ | | ∞ |
| 25 | | ∞ | | ∞ |
| 26 | | ∞ (end) | | ∞ (end) |

Example 1.29. Scalability, Flexibility, and Robustness of Devices

Results related to the scalability, flexibility and robustness of devices are summarized in FIG. 23 and Tables 3-5.

Figure 24:
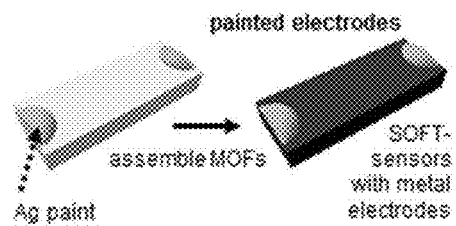
FIG. 24 shows pre-fabrication of electrodes for functional SOFT-sensors.
Figure 24:
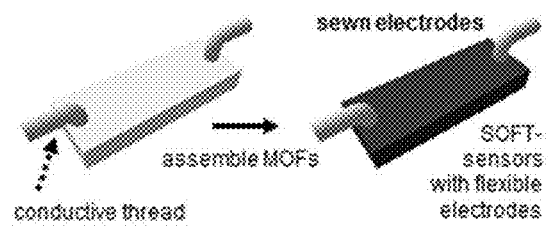
Figure 25:
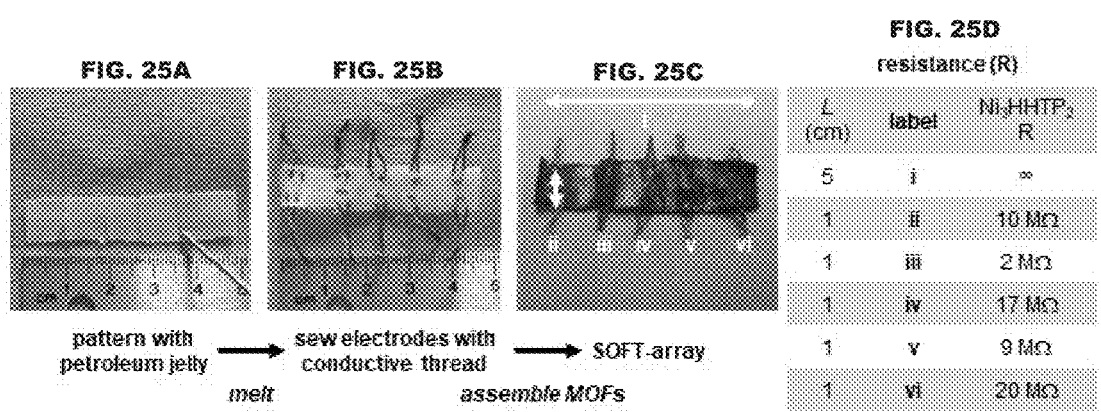
FIG. 25 shows custom design of SOFT-sensors through patterning treatment and electrode pre-fabrication.

Example 1.30. Custom Design of Devices Through Patterning and Pre-Fabrication Results related to the custom design of devices through patterning and pre-fabrication are summarized in FIGS. 24-25.

Example 1.31. Chemiresistive Sensing

For chemiresistive sensing measurements, a custom Teflon enclosure equipped with inlet and outlet ports was fabricated, and equipped with 10 spring-loaded gold pins, which served to immobilize the SOFT-swatches and make electrical contacts with external wires (5 swatches per enclosure). A PalmSense EmStatMUX potentiostat with a 16-channel multiplexer was connected to the enclosure wires through a breadboard, and the data collected using PSTrace 5 software. Unless otherwise specified, sensing experiments were performed under a constant applied voltage of 1.0 V. In all sensing experiments, swatches were allowed to equilibrate with applied voltage under a carrier gas stream of 4.0 L/min until a stable baseline level was achieved (30 minutes, minimum). Experiments employing SOFT-devices based on $Ni_3HHTP_2$ were conducted separately from experiments employing SOFT $Ni_3HITP_2$, as a consequence of their differences in initial current range ($Ni_3HHTP_2$: 0.1-0.3 µA, $Ni_3HITP_2$: 50-100 µA) under applied voltage of 1.0 V. Data was normalized and processed using Microsoft Excel. The chamber inlet was connected to a gas or vapor delivery system for controlled-concentration gas sensing measurements.

For the gas delivery system, A Sierra Micro-Trak and a Smart-Trak mass flow controller were used in combination to deliver controlled concentrations of gases from custom-ordered premixied tanks (1% CO, $NH_3$, $H_2S$, or NO balanced in $N_2$) equipped with two-stage stainless steel regulators. Gas streams from the tanks were further diluted with dry $N_2$ for delivery of controlled concentrations of gases ranging from 1-80 ppm. Typical overall flow rates equaled 0.4-4.0 L/min.

For vapor delivery systems, a Kintek FlexStream gas generator was used to produce vapors of analyte (ethanol, methanol, acetone, butanone, benzene, or water) diluted in dry $N_2$ to the desired concentration (500-5000 ppm). The generator was calibrated for each vapor by heating the internal permeation tube (50-90° C.), loading a vial of the desired solvent, and supplying a dilution stream at a set flow rate (total=4 L/min). Solvent mass loss over a minimum of 12 hours enabled determination of vapor concentration with respect to flow rate.

For combined gas/vapor delivery to produce a humidified stream of $N_2$, the gas generator permeation tube was heated to 90° C. using the embedded oven with temperature control, and loaded with a vial of deionized water. Using Equation 3, Applicants calculated deliverable concentration of water vapor, where MW=molecular weight of solvent (18.01 g/mol), m=solvent mass loss during calibration (1.9596 g), t=calibration time (1169.3 minutes), and f=flow rate of dry $N_2$ through the tube (mL/min) 90° C.

$$\text{ppm} = \frac{(m \times 10^{-9})}{t} \times \frac{22.41}{(f \times MW)} \qquad \text{Equation 3}$$

By varying the flow rate parameter, Applicants were able to maximize the deliverable ppm. Since the gas generator requires minimum flow rates>400 mL/min (lower flow rate=higher concentration), Applicants were able to deliver a maximum of 5000 ppm (span flow rate=417 mL/min) reliably. Heating the permeation tube containing water above 90° C. would have led to solvent boiling, which could damage the equipment. Consequently, 5000 ppm was the maximum deliverable humidity for the vapor delivery system used in this study. Total span gas flow through the oven was set to equal 417 mL/min. Zero dilution flow was not used for the humidified stream.

The resulting vapor stream was mixed with the gas stream delivered by the mass flow system using a Y-connection. The dilution stream of dry nitrogen usually employed for the dilution of tank gases was not used for this experiment, with the humid nitrogen from the gas generator serving as the dilution vapor. The dilution vapor (5000 ppm water) was mixed with the controlled stream from the mass flow controllers (3.6 mL/min) to deliver a humidified stream of a single gaseous analyte at 80 ppm.

For data Processing, Raw current data (collected under constant applied voltage) was normalized in Microsoft Excel and converted to normalized conductance according to Equation 4, in some embodiments $I_o$=initial current and I=current at various points during measurement.

$$\frac{I_o - I}{I_o} \times 100 = -\frac{\Delta G}{G_o} \qquad \text{Equation 4}$$

Statistical analysis was carried out using Excel add-in software called "AnalyzeIt."

Example 1.31A. Carrier Gas Dilution Stream=100% $N_2$

For SOFT-sensors dosed with $NH_3$, Applicants observe a slow decrease in resistance (saturation=−83±20%) for $Ni_3HHTP_2$, but no appreciable response for $Ni_3HITP_2$. These observations are consistent with results previously reported for $Ni_3HITP_2$, but different from other previously reported results for $Ni_3HHTP_2$.

Figure 26:
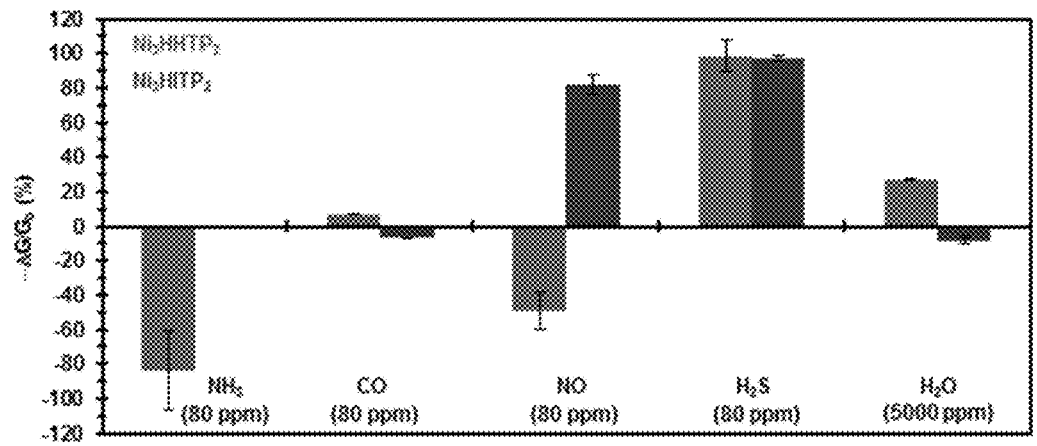
FIG. 26 shows a comprehensive saturation summary of sensing performance for $Ni_3HHTP_2$ and $Ni_3HITP_2$ SOFT-sensors (red and blue, respectively). Each average represents three devices exposed to 80 ppm analyte until saturated (1 hour total exposure), except for water (2 devices, 5000 ppm analyte). Error bars represent the standard deviation from the average (n=3).
Figure 27:
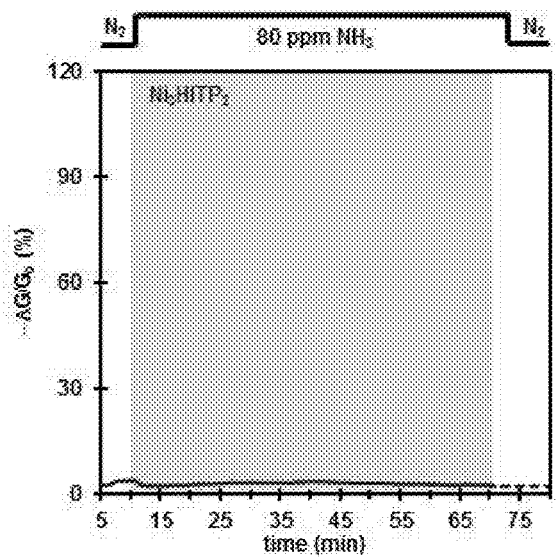
FIG. 27 shows representative saturation traces for $Ni_3HHTP_2$ (FIG. 27A) and $Ni_3HITP_2$ SOFT-sensors (FIG. 27B) exposed to $NH_3$ (80, 40, and 10 ppm), and $Ni_3HHTP_2$ (FIG. 27C) and $Ni_3HITP_2$ (FIG. 27D) SOFT-sensors exposed to CO (80 ppm). Changes in sensor response over time are attributable to electrical drift for CO exposures.
Figure 27:
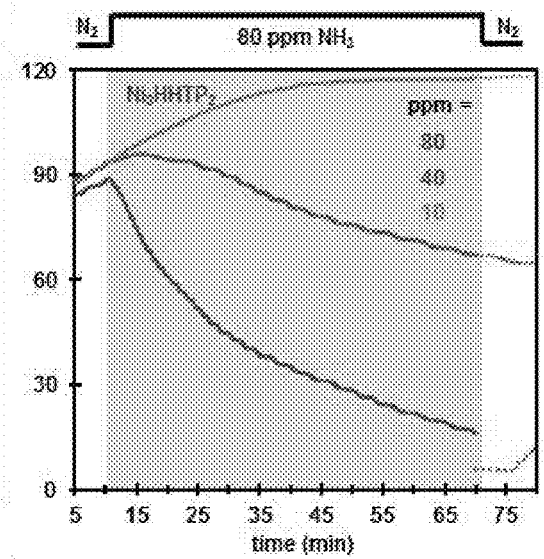
Figure 27:
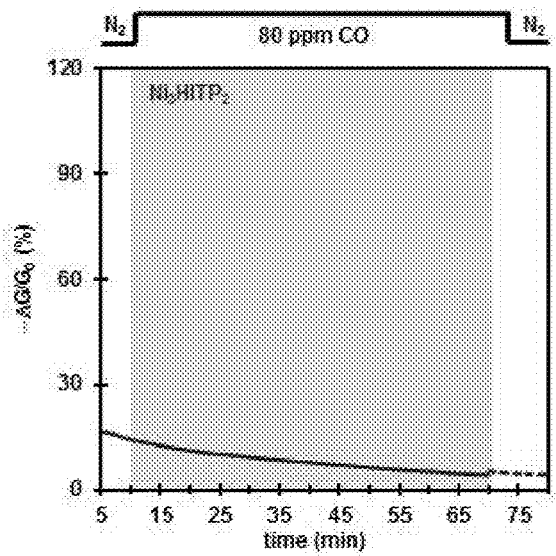
Figure 27:
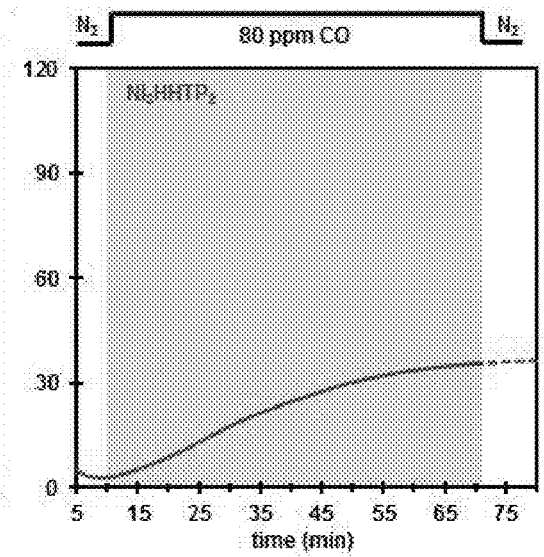
Figure 28:
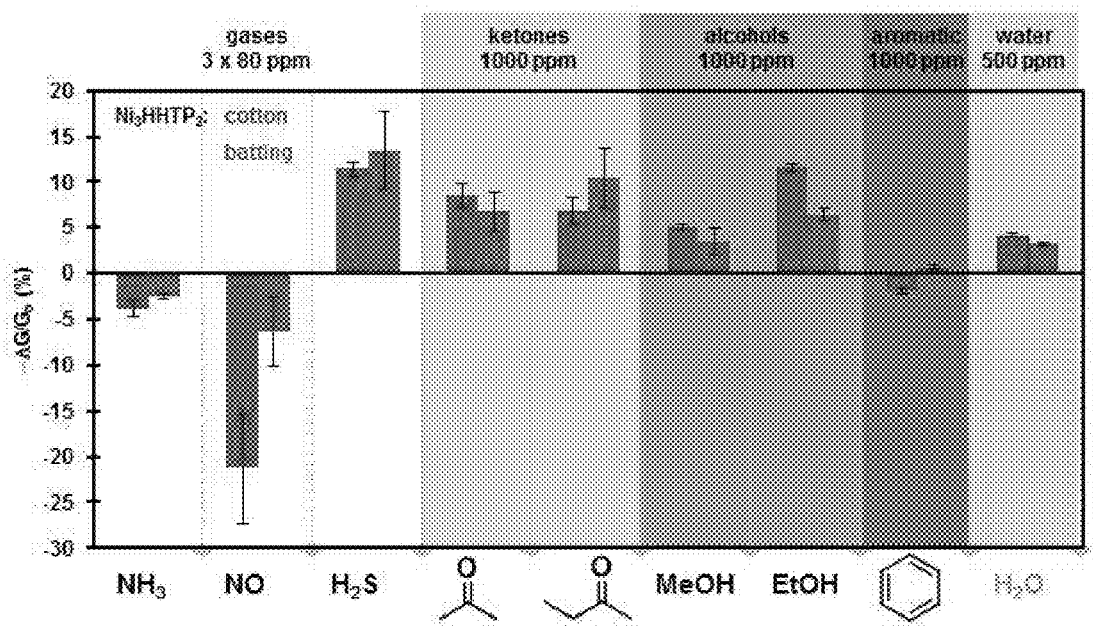
FIG. 28 shows a comprehensive summary of stepwise baseline, exposure, and recovery sensing performance for $Ni_3HHTP_2$ SOFT-sensors. Each average represents two devices. Each device was subjected to a baseline (10 minutes), dose with analyte (5 minute), recover (10 minutes) cycle, and the averages represent three exposures to analyte. Error bars represent the standard deviation between measurements, propagated. Representative traces for vapors are shown in FIG. 29.
Figure 29:
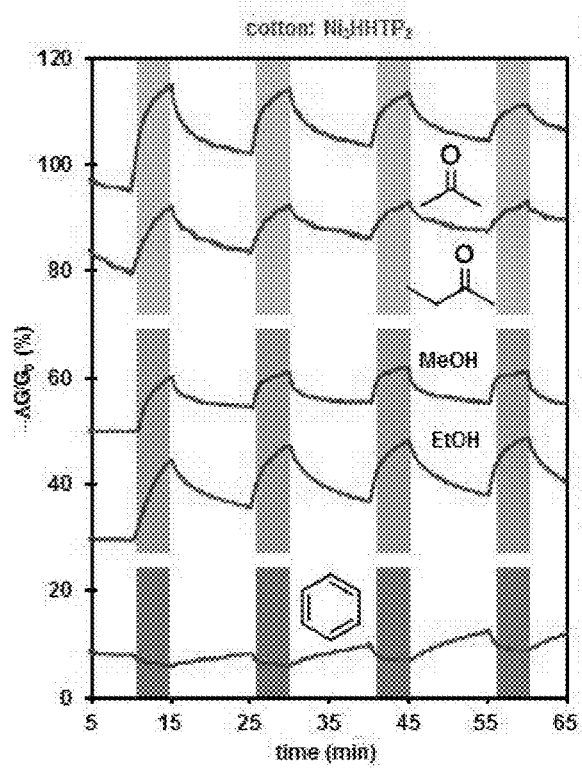
FIG. 29 shows representative stepwise baseline, exposure, and recovery sensing traces for $Ni_3HHTP_2$ SOFT-devices. Each device was subjected to a baseline (10 minutes), dose with analyte (5 minute, shown in gray), and recover (10 minutes) cycle. Analytes shown here are (from top to bottom) ketones (acetone, butanone), alcohols (methanol, ethanol), and organics (benzene). Representative sensing traces (4×1000 ppm analyte) for $Ni_3HHTP_2$ on cotton (red) (FIG. 29A) and $Ni_3HHTP_2$ on batting (green) (FIG. 29B) are also shown.
Figure 29:
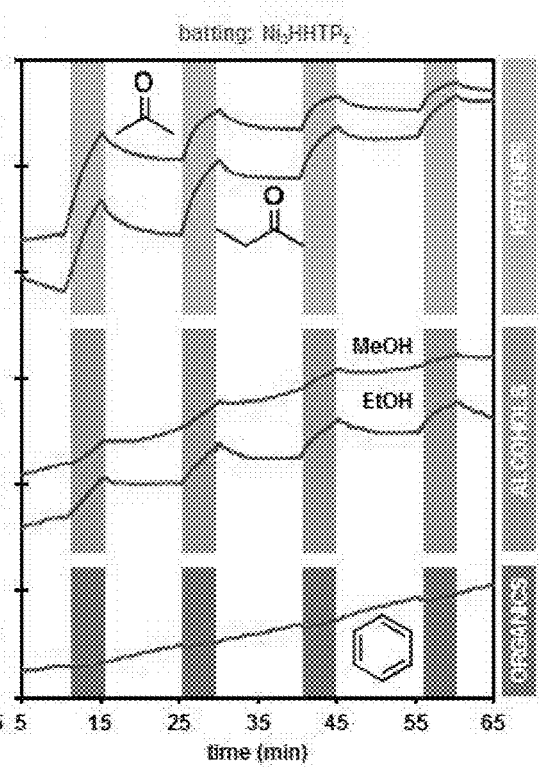
Figure 30:
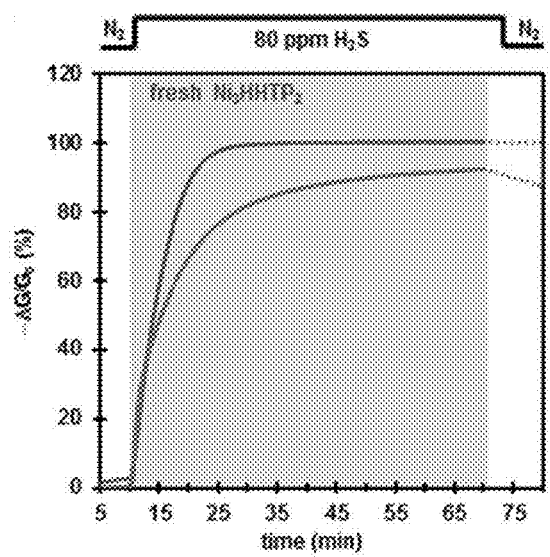
FIG. 30 shows representative sensing traces of a single batch of $Ni_3HHTP_2$ SOFT-sensor exposed to analytes. The traces represent the sensors exposed to $H_2S$ (80 ppm) when fresh (FIG. 30A), and after 50 days on the shelf (atmospheric air) (FIG. 30B). All traces in FIGS. 30A-B represent the first exposure to $H_2S$. The sensors exposed to NO (80 ppm) when fresh (FIG. 30C), and after 50 days on the shelf (atmospheric air) (FIG. 30D) also represent the first exposure to NO.
Figure 30:
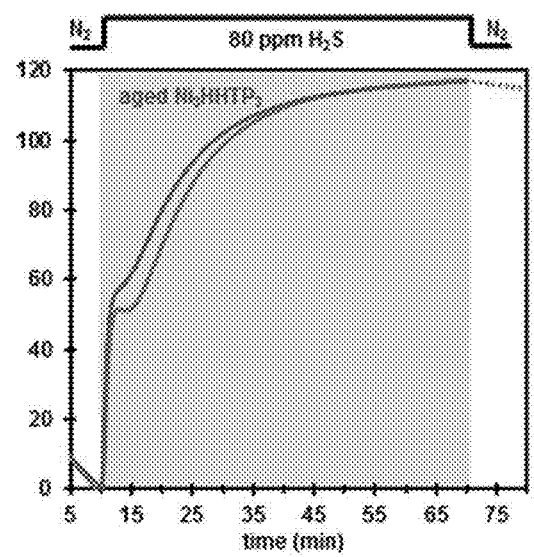
Figure 30:
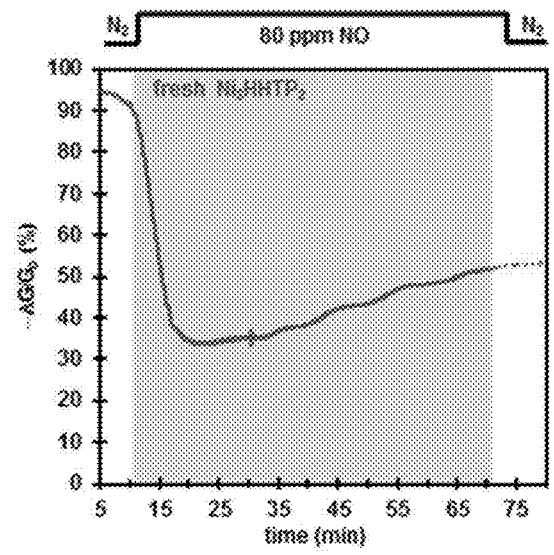
Figure 30:
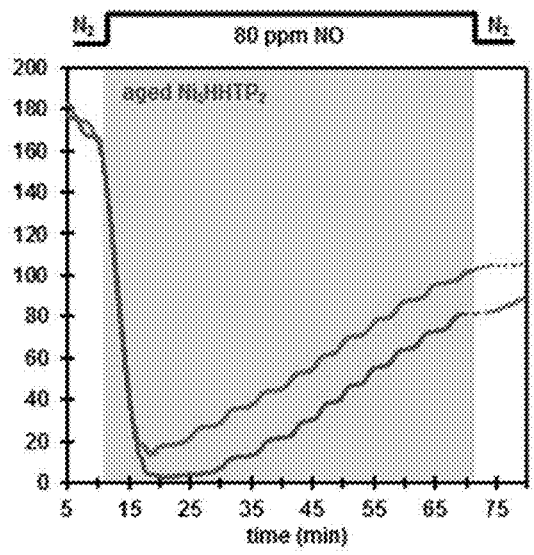

When dosed with $NH_3$ (80 ppm, 5 minutes) in previously reported work, sensors employing $Ni_3HHTP_2$ as the functional material did not produce a chemiresistive response when assembled on graphitic electrodes supported by polymer films. The difference between SOFT-devices and previously reported devices is likely attributed to the gradual nature of the response of $Ni_3HHTP_2$ to $NH_3$: at low, rapid doses, it would be indistinguishable from drift. Furthermore, the nature of the sensor architecture detailed in the previous reports differs fundamentally from the architecture and MOF density of SOFT-sensors. SOFT-sensors do not respond chemiresistively to CO when equilibrated in $N_2$, as shown in FIGS. 26-27. Additional results are shown in FIGS. 28-30.

Example 1.31B. Performance in Humidity, and Water Saturation Studies

Figure 31:
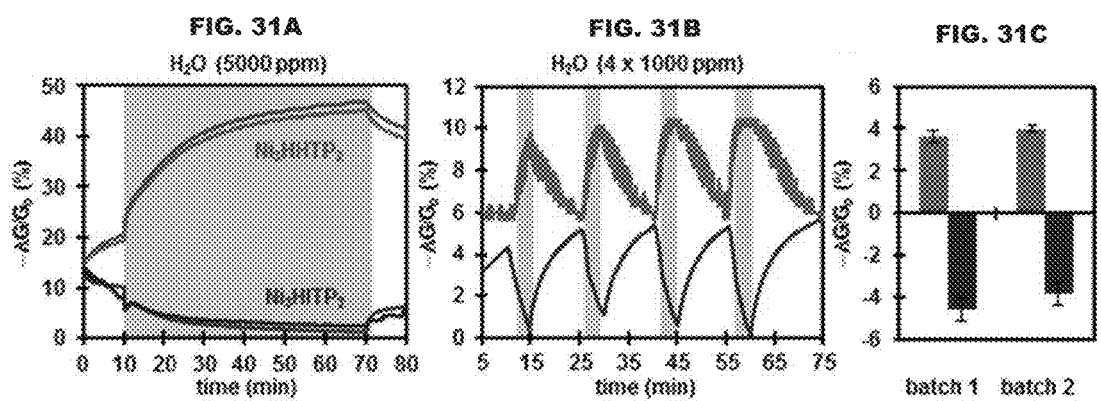
FIG. 31 shows the chemiresistive response of SOFT-devices exposed to water vapor.

Results relating to the performance of the SOFT-sensors in humid and aqueous conditions are summarized in FIGS. 31-32.

Example 1.31C. Limits of Detection

The theoretical limits of detection (LOD) were calculated using the following protocol. First, the root mean squared (rms) value—representing the noise-based deviation in $-\Delta G/G_o$—was calculated using the baseline trace before exposure to analyte. Applicants took 300 consecutive points (N=300) and fit the data to a polynomial ($5^{th}$ order). Applicants then calculated $V_{x_2}$ from Equation 5, where $y_i$=measured $-\Delta G/G_o$ and y is the value calculated from the extracted polynomial fit.

$$V_{x_2}=\Sigma(y-y_i)^2 \quad \text{Equation S5}$$

Applicants plotted concentration of analyte versus largest measured $-\Delta G/G_o$ and isolated the range of values in some embodiments this relationship was linear (FIG. 33). Linear regression provided an equation of best-fit (slope=m). With the values, Applicants extrapolated the theoretical LOD from Equations 6 and 7.

$$rms = \sqrt{\frac{V_{x^2}}{N}} \quad \text{Equation 6}$$

$$LOD = 3 \times \frac{rms}{m} \quad \text{Equation 7}$$

Using this method, Applicants calculated the LOD for each device/analyte pair, as shown in Table 6.

TABLE 6

Theoretical limits of detection calculated for each SOFT-device/analyte pair.

| SOFT-device | LOD NO | LOD H$_2$S |
|---|---|---|
| Ni$_3$HITP$_2$ | 160 ppb | 520 ppb |
| Ni$_3$HHTP$_2$ | 1.4 ppm | 230 ppb |

Example 1.32. Current/Voltage Plots with Analyte

Current/voltage plots with analytes are shown in FIGS. 34-35.

Example 1.33. Washing and Recovery Studies

Results related to washing and recovery studies are summarized in FIGS. 36-38.

Example 1.33. Breakthrough Experiments

Results related to breakthrough experiments are summarized in Table 7 and FIGS. 39-41.

TABLE 7

Breakthrough values for SOFT-devices as calculated at 10 minutes of exposure.

| devices | analyte | ppm | first membrane $-\Delta G/G_o$ | second membrane $-\Delta G/G_o$ | total volume analyte uptake (M) | mmoles analyte/g MOF (mmol/g) |
|---|---|---|---|---|---|---|
| Ni$_3$HHTP$_2 \times 2$ | H$_2$S | 20 | 7 | 2 | $16 \times 10^{-5}$ | 23.8 |
| Ni$_3$HHTP$_2 \times 2$ | NO | 20 | −3 | −1 | $15 \times 10^{-5}$ | 22.9 |
| Ni$_3$HITP$_2 \times 2$ | H$_2$S | 10 | 65 | 16 | $8 \times 10^{-5}$ | 12.3 |
| Ni$_3$HITP$_2 \times 2$ | NO | 10 | 11 | 2 | $9 \times 10^{-5}$ | 12.9 |

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of sensing an analyte in a sample, said method comprising:
    exposing the sample to a conductive textile,
        wherein the conductive textile comprises:
            a textile component comprising a plurality of fibers and a plurality of pores, and
            metal-organic frameworks associated with the fibers of the textile component,
                wherein the metal-organic frameworks comprise one or more metals and one or more organic ligands coordinated with the one or more metals, and
                wherein the metal-organic frameworks are in the form of a conductive network comprising a two-dimensional crystalline lattice; and
    detecting the presence or absence of the analyte from the sample, wherein the detecting comprises:
        detecting a change in a property of the conductive textile, and
        correlating the change in the property to the presence or absence of the analyte.

2. The method of claim 1, wherein the change in the property of the conductive textile comprises a change in normalized conductance over time ($\Delta G/Go$).

3. The method of claim 1, wherein the sample is derived from a gaseous environment.

4. The method of claim 1, wherein the analyte is selected from the group consisting of gases, ketones, alcohols, aromatic compounds, water, neurotransmitters, hormones, proteins, sugars, metal ions, NO, CO, H$_2$S, NH$_3$, H$_2$O, and combinations thereof.

5. The method of claim 1, wherein the analyte comprises one or more gases selected from the group consisting of NO, CO, H$_2$S, NH$_3$, H$_2$O, and combinations thereof.

6. The method of claim 1, wherein the exposing comprises flowing the sample through the conductive textile.

7. The method of claim 1, wherein the exposing comprises incubating the sample with the conductive textile.

8. The method of claim 1, wherein the exposing results in the reversible association of any analyte in the sample with the conductive textile.

9. The method of claim 8, wherein the association also results in filtration, pre-concentration, and capture of the analyte by the conductive textile.

10. The method of claim 1, wherein the analytes are detected at concentrations of less than about 100 ppm.

11. The method of claim 1, wherein the detecting comprises detecting a plurality of analytes.

12. The method of claim 1, wherein the detecting occurs in a humid environment, and wherein the humid environment has a relative humidity of 15% or higher.

13. The method of claim 1, further comprising a step of releasing the analyte from the conductive textile.

14. The method of claim 13, wherein the releasing occurs by washing the conductive textile.

* * * * *